US011017765B2

(12) United States Patent
Solomon et al.

(10) Patent No.: US 11,017,765 B2
(45) Date of Patent: *May 25, 2021

(54) INTELLIGENT ASSISTANT WITH INTENT-BASED INFORMATION RESOLUTION

(71) Applicant: Microsoft Technology Licensing, LLC, Redmond, WA (US)

(72) Inventors: Oz Solomon, Maple (CA); Christopher Brian Quirk, Seattle, WA (US); Han Yee Mimi Fung, Bellevue, WA (US); Keith Coleman Herold, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/700,308

(22) Filed: Dec. 2, 2019

(65) Prior Publication Data

US 2020/0104653 A1 Apr. 2, 2020

Related U.S. Application Data

(63) Continuation of application No. 15/657,031, filed on Jul. 21, 2017, now Pat. No. 10,496,905.

(Continued)

(51) Int. Cl.
*G10L 15/18* (2013.01)
*G06K 9/72* (2006.01)
(Continued)

(52) U.S. Cl.
CPC ........ *G10L 15/1822* (2013.01); *A61B 5/0205* (2013.01); *A61B 5/0507* (2013.01);
(Continued)

(58) Field of Classification Search
USPC ............................................... 704/7–10, 257
See application file for complete search history.

(56) References Cited

U.S. PATENT DOCUMENTS 7,783,486 B2  8/2010 Sturges et al.
8,885,882 B1  11/2014 Reale et al.
(Continued)

FOREIGN PATENT DOCUMENTS

CN  102760434 A  10/2012
CN  103209030 A   7/2013
(Continued)

OTHER PUBLICATIONS

"Non Final Office Action Issued in U.S. Appl. No. 15/832,656", dated Jan. 6, 2020, 9 Pages.
(Continued)

*Primary Examiner* — Leonard Saint Cyr
(74) *Attorney, Agent, or Firm* — Alleman Hall Creasman & Tuttle LLP

(57) ABSTRACT

A method for use with a computing device is provided. The method may include executing one or more programs of an intelligent digital assistant system at a processor and presenting a user interface to a user. At the processor, the method may include receiving natural language user input from the user, parsing the user input at an intent handler to determine an intent template with slots, populating the slots in the intent template with information from user input, and performing resolution on the intent template to partially resolve unresolved information. If a slot with missing slot information exists in the partially resolved intent template, a loop may be executed at the processor to fill the slots. The method may include, at the processor, determining that all required information is available and resolved and generat- (Continued)

ing a rule based upon the intent template with all required information being available and resolved.

18 Claims, 25 Drawing Sheets

Related U.S. Application Data

(60) Provisional application No. 62/482,165, filed on Apr. 5, 2017, provisional application No. 62/459,020, filed on Feb. 14, 2017.

(51) Int. Cl.

| | | |
|---|---|---|
| G06K 9/00 | (2006.01) | |
| G06T 7/70 | (2017.01) | |
| G06K 9/62 | (2006.01) | |
| G06F 3/16 | (2006.01) | |
| G06N 20/00 | (2019.01) | |
| G06T 7/292 | (2017.01) | |
| H04W 4/33 | (2018.01) | |
| H04W 4/029 | (2018.01) | |
| A61B 5/11 | (2006.01) | |
| A61B 5/117 | (2016.01) | |
| A61B 5/00 | (2006.01) | |
| G01S 5/28 | (2006.01) | |
| G06F 1/3206 | (2019.01) | |
| G06F 1/3231 | (2019.01) | |
| G06F 1/324 | (2019.01) | |
| G06F 3/01 | (2006.01) | |
| G06F 3/03 | (2006.01) | |
| G06F 21/32 | (2013.01) | |
| G10L 17/04 | (2013.01) | |
| G10L 17/08 | (2013.01) | |
| H04L 12/58 | (2006.01) | |
| H04L 29/08 | (2006.01) | |
| H04N 5/232 | (2006.01) | |
| H04N 7/18 | (2006.01) | |
| H04N 21/422 | (2011.01) | |
| H04N 21/442 | (2011.01) | |
| G07C 9/28 | (2020.01) | |
| G06F 40/35 | (2020.01) | |
| G06F 40/211 | (2020.01) | |
| G06T 7/73 | (2017.01) | |
| G06T 7/246 | (2017.01) | |
| G01S 5/18 | (2006.01) | |
| G06T 7/60 | (2017.01) | |
| G10L 15/22 | (2006.01) | |
| G10L 15/28 | (2013.01) | |
| H04R 1/40 | (2006.01) | |
| H04R 3/00 | (2006.01) | |
| H04N 5/33 | (2006.01) | |
| G10L 15/02 | (2006.01) | |
| G06N 5/02 | (2006.01) | |
| G06N 5/04 | (2006.01) | |
| G10L 15/06 | (2013.01) | |
| G10L 15/24 | (2013.01) | |
| G10L 15/26 | (2006.01) | |
| G10L 15/19 | (2013.01) | |
| G10L 15/08 | (2006.01) | |
| G10L 15/32 | (2013.01) | |
| G10L 25/51 | (2013.01) | |
| H04L 29/06 | (2006.01) | |
| A61B 5/0205 | (2006.01) | |
| A61B 5/0507 | (2021.01) | |
| G06F 21/35 | (2013.01) | |
| G08B 13/14 | (2006.01) | |
| G06F 3/0482 | (2013.01) | |
| G06F 3/0484 | (2013.01) | |
| H04N 21/231 | (2011.01) | |
| G06F 3/0488 | (2013.01) | |
| G06F 16/70 | (2019.01) | |
| A61B 5/05 | (2021.01) | |
| G01S 5/16 | (2006.01) | |
| G01S 13/86 | (2006.01) | |
| G06N 3/04 | (2006.01) | |
| G08B 29/18 | (2006.01) | |
| G10L 17/00 | (2013.01) | |
| G07C 9/32 | (2020.01) | |
| H04N 5/247 | (2006.01) | |
| G01S 13/38 | (2006.01) | |
| G01S 13/88 | (2006.01) | |

(52) U.S. Cl.
CPC ............ *A61B 5/117* (2013.01); *A61B 5/1113* (2013.01); *A61B 5/7475* (2013.01); *G01S 5/18* (2013.01); *G01S 5/28* (2013.01); *G06F 1/324* (2013.01); *G06F 1/3206* (2013.01); *G06F 1/3231* (2013.01); *G06F 3/011* (2013.01); *G06F 3/017* (2013.01); *G06F 3/0304* (2013.01); *G06F 3/0482* (2013.01); *G06F 3/04842* (2013.01); *G06F 3/167* (2013.01); *G06F 21/32* (2013.01); *G06F 21/35* (2013.01); *G06F 40/211* (2020.01); *G06F 40/35* (2020.01); *G06K 9/00* (2013.01); *G06K 9/00214* (2013.01); *G06K 9/00255* (2013.01); *G06K 9/00261* (2013.01); *G06K 9/00288* (2013.01); *G06K 9/00295* (2013.01); *G06K 9/00342* (2013.01); *G06K 9/00362* (2013.01); *G06K 9/00711* (2013.01); *G06K 9/00771* (2013.01); *G06K 9/00973* (2013.01); *G06K 9/6254* (2013.01); *G06K 9/6255* (2013.01); *G06K 9/6289* (2013.01); *G06K 9/6296* (2013.01); *G06K 9/726* (2013.01); *G06N 5/025* (2013.01); *G06N 5/047* (2013.01); *G06N 20/00* (2019.01); *G06T 7/248* (2017.01); *G06T 7/292* (2017.01); *G06T 7/60* (2013.01); *G06T 7/70* (2017.01); *G06T 7/74* (2017.01); *G07C 9/28* (2020.01); *G08B 13/1427* (2013.01); *G10L 15/02* (2013.01); *G10L 15/063* (2013.01); *G10L 15/08* (2013.01); *G10L 15/18* (2013.01); *G10L 15/1815* (2013.01); *G10L 15/19* (2013.01); *G10L 15/22* (2013.01); *G10L 15/24* (2013.01); *G10L 15/26* (2013.01); *G10L 15/28* (2013.01); *G10L 15/32* (2013.01); *G10L 17/04* (2013.01); *G10L 17/08* (2013.01); *G10L 25/51* (2013.01); *H04L 51/02* (2013.01); *H04L 63/102* (2013.01); *H04L 67/12* (2013.01); *H04L 67/22* (2013.01); *H04N 5/23219* (2013.01); *H04N 5/332* (2013.01); *H04N 7/181* (2013.01); *H04N 7/188* (2013.01); *H04N 21/231* (2013.01); *H04N 21/42203* (2013.01); *H04N 21/44218* (2013.01); *H04N 21/44222* (2013.01); *H04R 1/406* (2013.01); *H04R 3/005* (2013.01); *H04W 4/029* (2018.02); *H04W 4/33* (2018.02); *A61B 5/05* (2013.01); *A61B 5/1118* (2013.01); *G01S 5/16* (2013.01); *G01S 13/38* (2013.01); *G01S 13/867* (2013.01); *G01S 13/888* (2013.01); *G06F 3/0488* (2013.01); *G06F 16/70* (2019.01); *G06F 2203/0381* (2013.01); *G06F 2221/2111*

(2013.01); *G06K 2209/09* (2013.01); *G06N 3/0445* (2013.01); *G06T 2207/10016* (2013.01); *G06T 2207/10024* (2013.01); *G06T 2207/20101* (2013.01); *G06T 2207/30196* (2013.01); *G06T 2207/30201* (2013.01); *G06T 2207/30204* (2013.01); *G06T 2207/30232* (2013.01); *G07C 9/32* (2020.01); *G08B 29/186* (2013.01); *G10L 17/00* (2013.01); *G10L 2015/0635* (2013.01); *G10L 2015/088* (2013.01); *G10L 2015/223* (2013.01); *G10L 2015/225* (2013.01); *G10L 2015/228* (2013.01); *H04N 5/247* (2013.01); *Y02D 10/00* (2018.01)

(56) References Cited

U.S. PATENT DOCUMENTS

| | | | |
|---|---|---|---|
| 9,070,366 | B1 | 6/2015 | Mathias et al. |
| 9,123,330 | B1 | 9/2015 | Sharifi et al. |
| 9,159,116 | B2 | 10/2015 | Plagemann et al. |
| 9,245,497 | B2 | 1/2016 | Pais et al. |
| 9,372,851 | B2 * | 6/2016 | Hazen ............ G06F 40/279 |
| 9,669,296 | B1 | 6/2017 | Hibbert et al. |
| 9,747,896 | B2 | 8/2017 | Kennewick et al. |
| 10,276,149 | B1 | 4/2019 | Liang et al. |
| 10,482,885 | B1 | 11/2019 | Moniz |
| 10,599,390 | B1 | 3/2020 | Brahmbhatt et al. |
| 2006/0067536 | A1 | 3/2006 | Culbert et al. |
| 2008/0015864 | A1 | 1/2008 | Ross et al. |
| 2011/0119060 | A1 | 5/2011 | Aronowitz |
| 2011/0302535 | A1 | 12/2011 | Clerc et al. |
| 2013/0144616 | A1 | 6/2013 | Bangalore et al. |
| 2013/0259456 | A1 | 10/2013 | Viswanathan |
| 2013/0304479 | A1 | 11/2013 | Teller et al. |
| 2014/0100997 | A1 | 4/2014 | Mayerle et al. |
| 2014/0160290 | A1 | 6/2014 | Wu |
| 2015/0032254 | A1 | 1/2015 | Ishiguro |
| 2015/0035976 | A1 | 2/2015 | Mayuzumi |
| 2015/0134547 | A1 | 5/2015 | Oikonomidis |
| 2015/0195666 | A1 | 7/2015 | Massey et al. |
| 2015/0220244 | A1 | 8/2015 | Vats et al. |
| 2015/0278199 | A1 * | 10/2015 | Hazen ............ G06F 40/40 704/9 |
| 2015/0340033 | A1 * | 11/2015 | Di Fabbrizio ...... G10L 15/1815 704/254 |
| 2015/0371639 | A1 | 12/2015 | Foerster et al. |
| 2016/0063989 | A1 | 3/2016 | Deleeuw |
| 2016/0110347 | A1 | 4/2016 | Kennewick et al. |
| 2016/0171289 | A1 | 6/2016 | Lee et al. |
| 2016/0253310 | A1 * | 9/2016 | Hazen ............ G06F 40/253 704/9 |
| 2016/0259623 | A1 | 9/2016 | Sumner et al. |
| 2016/0313868 | A1 | 10/2016 | Weng et al. |
| 2017/0169476 | A1 | 6/2017 | Nomula et al. |
| 2017/0186290 | A1 | 6/2017 | Li et al. |
| 2017/0206900 | A1 | 7/2017 | Lee et al. |
| 2017/0213157 | A1 | 7/2017 | Bugay et al. |
| 2017/0255450 | A1 | 9/2017 | Mullins et al. |
| 2017/0269975 | A1 | 9/2017 | Wood et al. |
| 2017/0286530 | A1 | 10/2017 | Paruchuri et al. |
| 2017/0357637 | A1 | 12/2017 | Nell et al. |
| 2018/0009118 | A1 | 1/2018 | Yamaga et al. |
| 2018/0090143 | A1 | 3/2018 | Saddler et al. |
| 2018/0107930 | A1 | 4/2018 | Aggarwal et al. |
| 2018/0314689 | A1 | 11/2018 | Wang et al. |
| 2018/0333862 | A1 | 11/2018 | Hayashi |
| 2020/0012906 | A1 | 1/2020 | Albadawi et al. |
| 2020/0042839 | A1 | 2/2020 | Herold et al. |

FOREIGN PATENT DOCUMENTS

| | | |
|---|---|---|
| CN | 103262156 A | 8/2013 |
| CN | 104272709 A | 1/2015 |
| CN | 104423537 A | 3/2015 |
| CN | 105070288 A | 11/2015 |
| CN | 105389307 A | 3/2016 |
| CN | 105408891 A | 3/2016 |
| CN | 105611500 A | 5/2016 |
| CN | 106104517 A | 11/2016 |
| CN | 106157952 A | 11/2016 |
| CN | 106164921 A | 11/2016 |
| CN | 106340299 A | 1/2017 |
| WO | 2016043005 A1 | 3/2016 |
| WO | 2016157662 A1 | 10/2016 |

OTHER PUBLICATIONS

"Non Final Office Action Issued in U.S. Appl. No. 15/657,822", dated Feb. 6, 2020, 25 Pages.

"Final Office Action Issued in U.S. Appl. No. 15/646,871", dated Jan. 21, 2020, 23 Pages.

"Final Office Action Issued in U.S. Appl. No. 15/640,251", dated Jan. 30, 2020, 21 Pages.

"Non Final Office Action Issued in U.S. Appl. No. 16/005,470", dated Feb. 24, 2020, 11 Pages.

"Notice of Allowance Issued in U.S. Appl. No. 16/573,677", dated Nov. 6, 2019, 9 Pages.

"Non Final Office Action Issued in U.S. Appl. No. 15/640,113", dated May 14, 2020, 13 Pages.

"Non Final Office Action Issued in U.S. Appl. No. 15/640,201", dated May 27, 2020, 11 Pages.

"Notice of Allowance Issued in U.S. Appl. No. 15/832,656", dated Apr. 22, 2020, 8 Pages.

"Notice of Allowance Issued in U.S. Appl. No. 15/832,672", dated Jun. 2, 2020, 11 Pages.

"Non Final Office Action Issued in U.S. Appl. No. 15/936,076", dated Apr. 15, 2020, 23 Pages.

"Office Action Issued in European Patent Application No. 18707800.1", dated Jun. 4, 2020, 4 Pages.

"Office Action Issued in European Patent Application No. 18708508.9", dated May 28, 2020, 6 Pages.

"Office Action Issued in European Patent Application No. 18706104.9", dated Sep. 21, 2020, 4 Pages.

Sarikaya, Ruhi, "The Technology Behind Personal Digital Assistants: An Overview of the System Architecture and key Components", In Journal of IEEE Signal Processing Magazine, vol. 34, Issue 1, Jan. 11, 2017, pp. 67-81.

"Non Final Office Action Issued in U.S. Appl. No. 15/980,631", dated Sep. 18, 2020, 12 Pages "Notice of Allowance Issued in U.S. Appl. No. 15/640,251", dated Jul. 31, 2020, 11 Pages.

"Non Final Office Action Issued in U.S. Appl. No. 15/646,871", dated Jul. 1, 2020, 24 Pages.

"Final Office Action Issued in U.S. Appl. No. 15/657,822", dated Aug. 7, 2020, 22 Pages.

"Final Office Action Issued in U.S. Appl. No. 16/005,470", dated Sep. 4, 2020, 15 Pages.

"First Office Action and Search Report Issued in Chinese Patent Application No. 201880011578.3", dated Feb. 02, 2021, 12 Pages.

"First Office Action and Search Report Issued in Chinese Patent Application No. 201880011967.6", dated Feb. 2, 2021, 13 Pages.

"First Office Action and Search Report Issued in Chinese Patent Application No. 201880011970.8", dated Feb. 2, 2021, 15 Pages.

"First Office Action and Search Report Issued in Chinese Patent Application No. 201880012028.3", dated Feb. 2, 2021, 13 Pages.

"Non Final Office Action Issued in U.S. Appl. No. 16/599,426", dated Jan. 12, 2021, 10 Pages.

"First Office Action and Search Report Issued in Chinese Patent Application No. 201880011885.1", dated Feb. 01, 2021, 16 Pages.

* cited by examiner

INTELLIGENT ASSISTANT WITH INTENT-BASED INFORMATION RESOLUTION

CROSS REFERENCE TO RELATED APPLICATIONS

This application is a continuation from U.S. patent application Ser. No. 15/657,031 filed Jul. 21, 2017, which claims priority to U.S. Provisional Patent Application No. 62/459,020 filed Feb. 14, 2017, and to U.S. Provisional Patent Application No. 62/482,165 filed Apr. 5, 2017, the entirety of each of which is hereby incorporated herein by reference.

BACKGROUND

Interacting with computing systems via natural interactions, such as one or more of voice recognition, text, gesture recognition, motion detection, gaze detection, intent recognition, brain activity assessment, text, the state of a home automated device, etc., enables natural user interface experiences. As the volume of digital information and the numbers of computing devices increase, managing such natural user interaction interfaces to provide positive user experiences can prove challenging. User input given by way of natural language requires a computing system that can appropriately interpret the information.

SUMMARY

According to one aspect of the present disclosure, a method for use with a computing device is provided that includes executing one or more programs of an intelligent digital assistant system at a processor. The one or more programs may present a user interface to a user. The method may include, at the processor, receiving natural language user input from the user via the user interface and parsing the user input at an intent handler of the system to generate an intent template with slots for information. The method may further include, at the processor, populating the slots in the intent template with collected information from the user input and performing resolution on the intent template to partially resolve unresolved information, thereby resulting in a partially resolved intent template. Furthermore, if, in the partially resolved intent template, a slot with missing slot information that is required by the intent template exists, then the method may include, at the processor, performing the following actions in a loop: identifying a slot with missing slot information specified as required by the intent template; attempting to fill the slot with missing slot information based upon implicit knowledge derived from previously filled slots and other context information available to the system; if information is still missing, presenting a missing information query to the user to fill the slot with the missing slot information; receiving a user response to the missing information query; re-performing resolution based on the partially resolved intent template and the user response; and exiting the loop upon determining that no slot exists with missing and required slot information. The method may further include, at the processor, determining that all required information is available and resolved in the intent template and generating a rule based upon the intent template with all required information being available and resolved.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

Overview

The present disclosure relates generally to systems, methods and logical constructs for providing intelligent assistance to users. In some examples, a variety of sensor data may be utilized to intelligently determine the content and/or timing of messages communicated to users and/or the performance of actions. In some examples, natural language inputs, such as user commands and other utterances, may be received and processed. In some examples, a natural language input may be parsed and analyzed to generate an indication of one or more user intentions associated with the input. In some examples, data from one or more sensors also may be utilized to process the natural language inputs and/or user intentions. Such data may be processed to generate identity, location/position, status/activity, and/or other information related to one or more entities within range of a sensor. Statistical probabilities based on current and past data may be utilized to generate confidence values associated with entity information.

User intentions may be processed to at least partially resolve linguistic, semantic and/or other ambiguities. Using the resulting clarified intention, a commitment for carrying out the intention may be generated and either executed or stored. In determining whether and when to execute a commitment, one or more factors may be examined. In some examples, factors related to the importance of the commitment to a particular user, the receptivity of the user to receiving input, and/or the user's current context may be estimated. Machine learning techniques may be applied to such factors and other data to learn and make predictions from such information.

Following are descriptions of example implementations and use cases of an intelligent digital assistant system for processing natural language inputs. Additional details of various aspects of the system are provided below.

Example Environment

Figure 1:
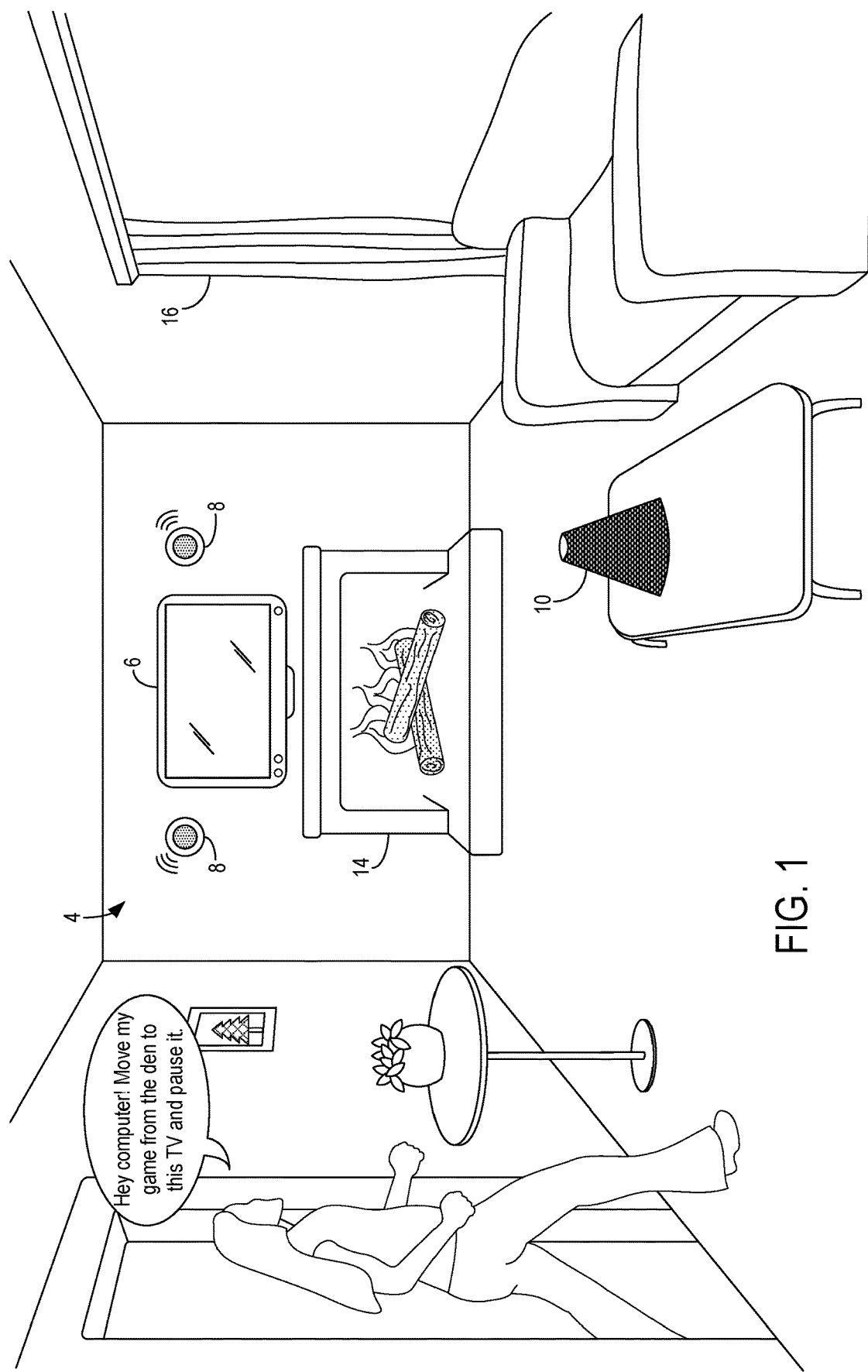
FIG. 1 shows an example environment with an intelligent digital assistant system in the form of an all-in-one computing device according to an example of the present disclosure.

FIG. 1 shows an example of a living room 4 with one example of an intelligent digital assistant system in the form of an all-in-one computing device 10. As described in more detail below, in some examples computing device 10 may be configured to receive and process natural language inputs. A user may utilize the intelligent digital assistant system for myriad functions. For example, the user may provide natural language input to ask the intelligent digital assistant system to perform a variety of tasks, such as transferring an instance of a computer game from one device to another. In another example, such a transfer may be performed programmatically without input from the user. For example, computing device 10 may utilize sensor data, such as audio and/or video data, to detect when the user moves to another room and is looking at or "engaged" with another device. Using this data, computing device 10 may automatically transfer the instance of the computer game to the other device.

The user may ask the system for information about a wide range of topics, such as the weather, personal calendar events, movie show times, etc. In some examples, the intelligent digital assistant system also may be configured to control elements in the living room 4, such as a television 6, speakers 8 of a music system, a gas fireplace 14, or motorized curtains 16.

The intelligent digital assistant system also may be utilized to receive and store messages and/or reminders to be delivered at an appropriate future time. Using data received from sensors, the intelligent digital assistant system may track and/or communicate with one or more users or other entities.

In some examples, the computing device 10 may be operatively connected with one or more other computing devices using a wired connection, or may employ a wireless connection via Wi-Fi, Bluetooth, or any other suitable wireless communication protocol. For example, the computing device 10 may be communicatively coupled to one or more other computing devices via a network. The network may take the form of a local area network (LAN), wide area network (WAN), wired network, wireless network, personal area network, or a combination thereof, and may include the Internet. Additional details regarding components and computing aspects of the computing device 10 are described in more detail below with reference to FIG. 27.

It will be appreciated that the computing device 10 of FIG. 1 is merely one example implementation of the intelligent digital assistant system of the present disclosure. Additional example implementations across two or more devices are illustrated in FIGS. 17-22 and described in more detail below.

Architecture

Figure 2:
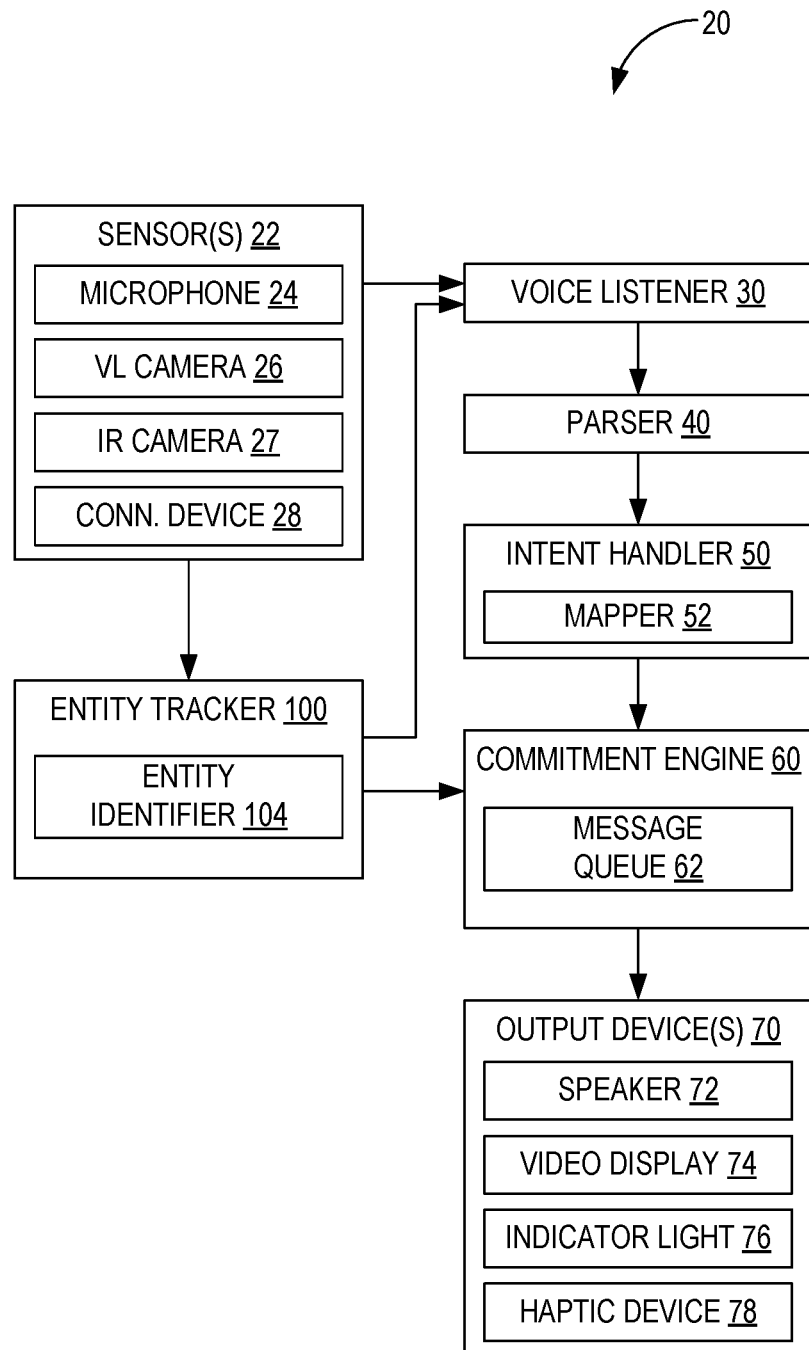
FIG. 2 schematically shows an example logical architecture for implementing an intelligent digital assistant system according to an example of the present disclosure.

FIG. 2 shows an example logical architecture for implementing an intelligent digital assistant system 20 capable of recognizing and responding to natural language inputs according to examples of the present disclosure. As described in more detail below, in various examples the system 20 may be implemented in a single computing device, across two or more devices, in a cloud-supported network, and in combinations of the foregoing.

In this example the intelligent digital assistant system 20 includes at least one sensor 22, an entity tracker 100, a voice listener 30, a parser 40, an intent handler 50, a commitment engine 60, and at least one output device 70. In some examples the sensors 22 may include one or more microphones 24, visible light cameras 26, infrared cameras 27, and connectivity devices 28, such as Wi-Fi or Bluetooth modules. In some examples sensor(s) 22 may comprise stereoscopic and/or depth cameras, head trackers, eye trackers, accelerometers, gyroscopes, gaze detection devices, electric-field sensing componentry, GPS or other location tracking devices, temperature sensors, device state sensors, and/or any other suitable sensor.

The entity tracker 100 is configured to detect entities and their activities, including people, animals, or other living things, as well as non-living objects. Entity tracker 100 includes an entity identifier 104 that is configured to recognize individual users and/or non-living objects. Voice listener 30 receives audio data and utilizes speech recognition functionality to translate spoken utterances into text. Voice listener also may assign confidence value(s) to the translated text, and may perform speaker recognition to determine an identity of the person speaking, as well as assign probabilities to the accuracy of such identifications. Parser 40 analyzes text and confidence values received from voice listener 30 to derive user intentions and generate corresponding machine-executable language.

Intent handler 50 receives the machine-executable language representing user intentions from the parser 40, and resolves missing and ambiguous information to generate commitments. Commitment engine 60 stores commitments from the intent handler 50. At a contextually appropriate time, the commitment engine may deliver one or more messages and/or execute one or more actions that are associated with one or more commitments. Commitment engine 60 may store messages in a message queue 62 or cause one or more output devices 70 to generate output. The output devices 70 may comprise one or more of speaker(s) 72, video display(s) 74, indicator light(s) 76, haptic device (s) 78, and/or other suitable output devices. In other examples, output devices 70 may comprise one or more other devices or systems, such as home lighting, thermostats, media programs, door locks, etc., that may be controlled via actions executed by the commitment engine 60.

In different examples the voice listener 30, parser 40, intent handler 50, commitment engine 60, and/or entity tracker 100 may be embodied in software that is stored in memory and executed by one or more processors of a computing device. Additional details regarding the components and computing aspects of computing devices that may store and execute these modules are described in more detail below with reference to FIG. 27.

Additional descriptions of the components of intelligent digital assistant system 20 will now be provided. In some examples, voice listener 30 may receive audio data from the surrounding environment. In some examples, such as in computing device 10 of FIG. 1, the voice listener 30 may comprise a software module that is embodied in a standalone device that comprises one or more microphones. In other examples, the voice listener 30 software module may be stored in memory of a computing device that is located remotely from the user's environment, such as in a cloud-based service. In some examples, additional data from one or more other sensors may be received and utilized by the voice listener 30 in performing its functions that are described in more detail below.

Figure 3:
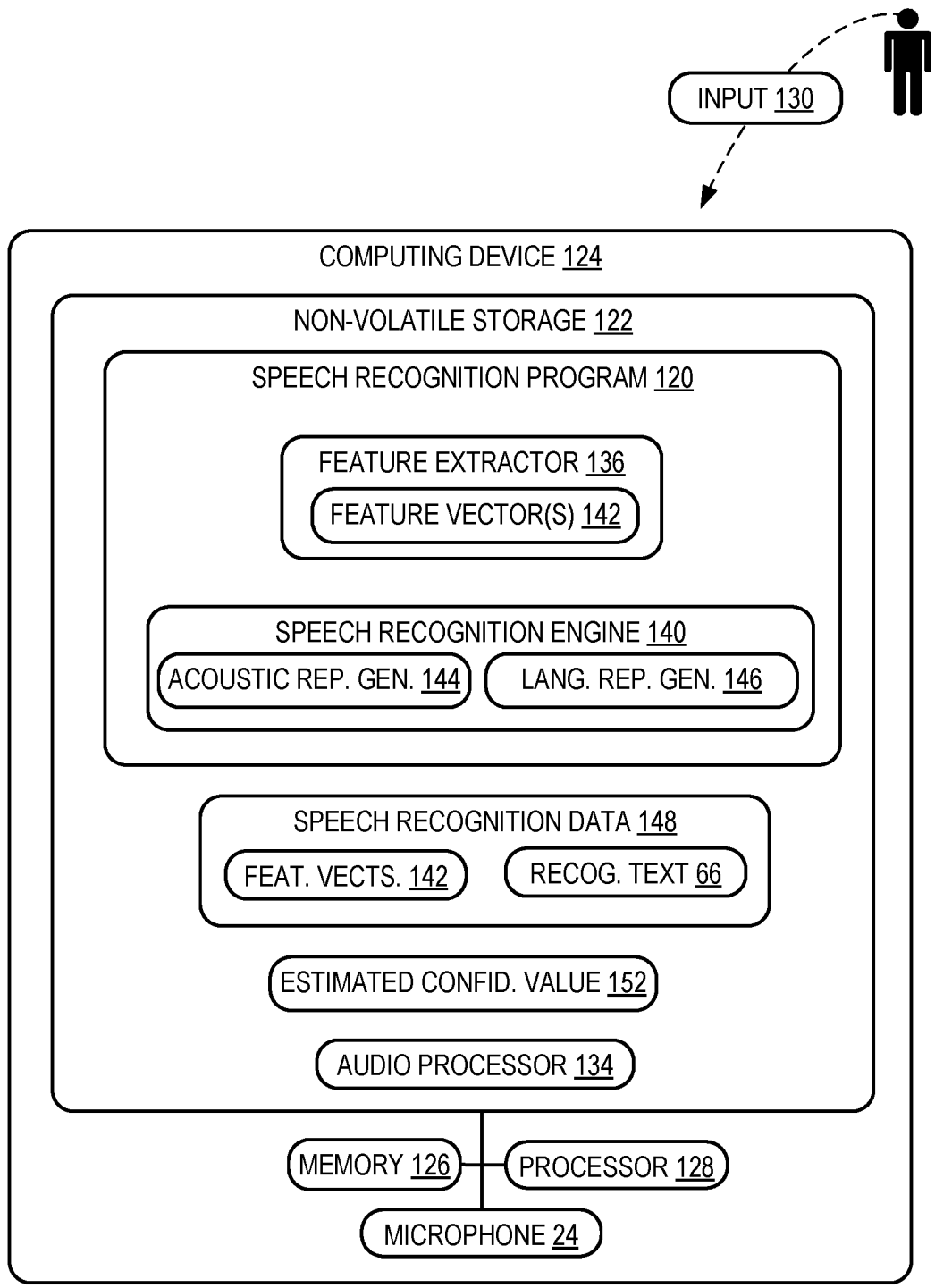
FIG. 3 schematically shows a speech recognition program that may be utilized by a voice listener according to an example of the present disclosure.

The voice listener 30 may comprise speech recognition functionality that translates audio data of spoken utterances into text. As described in more detail below, the voice listener 30 also may assign a confidence value to one or more portions of translated text, such as individual speech components, words, phrases, etc. With reference now to FIG. 3, in some examples the voice listener 30 may comprise a speech recognition program 120 stored in non-volatile storage 122 of a computing device 124. The speech recognition program 120 may be loaded into memory 126 and executed by a processor 128 of computing device 124 to perform one or more of the methods and processes for speech recognition described in more detail below.

Audio input 130 in the form of natural language speech may be captured by microphone 24 and processed by audio processor 134 to create audio data. Audio data from the audio processor 134 may be transformed by feature extractor 136 into data for processing by a speech recognition engine 140 of the speech recognition program 120. In some examples, feature extractor 136 may identify portions of the audio data over a time interval that contain speech for processing. Feature extractor 136 may extract feature vectors 142 from such portions of the data, with a feature vector representing the qualities of a spoken utterance within the time interval of a given portion. A matrix of multiple feature vectors 142 may be provided to the speech recognition engine 140 for further processing.

Feature extractor 136 may utilize any suitable dimensionality reduction techniques to process the audio data and generate feature vectors 142. Example techniques include using mel-frequency cepstral coefficients (MFCCs), linear discriminant analysis, deep neural network techniques, etc.

The speech recognition engine 140 may compare the feature vectors 142 generated by feature extractor 136 with acoustic models for speech sounds (e.g., speech components). Examples of speech components may include phonemes, phones, diphones, triphones, etc. In some examples, the speech recognition engine 140 may comprise an acoustic representation generator 144 (e.g., acoustic modeler) that evaluates the similarity of a spoken utterance represented by one or more feature vectors 142 to acoustic models of language sounds. The acoustic models may comprise data that matches pronunciations of speech components, such as phonemes, to particular words and/or phrases.

The speech recognition engine 140 also may compare the feature vectors and other audio data with sequences of sounds to identify words and/or phrases that match the spoken sounds of the audio data. The speech recognition program 120 may comprise a language representation generator 146 (e.g., language modeler) that may utilize language models to evaluate the likelihood that a particular word would be included in a phrase (which in some cases may comprise a sentence) at a particular location. For purposes of the present disclosure, a phrase may include two or more words that may or may not be considered a complete sentence.

In some examples, the speech recognition engine 140 may utilize Hidden Markov models (HMMs) to match feature vectors 142 with phonemes and/or other speech components. An HMM outputs sequences of n-dimensional vectors, where n is an integer such as 10. Sequences may be generated at a given frequency, such as one sequence every 10 milliseconds.

Each state of an HMM may comprise a statistical distribution that is a mixture of diagonal covariance Gaussians, which may indicate a likelihood for each observed vector. Each phoneme or word may have a different output distribution. Individual HMMs for separate phonemes and words may be combined to create an HMM for a sequence of phonemes or words.

Context dependency for phonemes may be provided by different states of an HMM. Such context-dependent HMM states may be associated with a model, such as a Gaussian mixture model (GMM). In some examples, transitions between states may be assigned probabilities that correspond to a likelihood that a current state may be reached from a previous state. Different paths between states of the HMM may represent inputted sounds, with the different paths representing multiple possible text matches for the same sound.

Using the feature extractor 136 and speech recognition engine 140, the speech recognition program 120 may process feature vectors 142 and other speech recognition data 148 to generate recognized text 66. In other examples, any suitable techniques for matching feature vectors 142 to phonemes and/or other speech components may be utilized.

In some examples, the speech recognition program 120 may determine estimated confidence values 152 for one or more portions of the speech recognition data 148, such as individual speech components, words and phrases. An estimated confidence value 152 may define a statistical likelihood that the corresponding recognized text is accurate. As described in more detail below, the parser 40 of intelligent digital assistant system 20 may utilize such confidence values 152 in processing recognized text and determining a user's intent.

In different examples, confidence values 152 may be determined by utilizing one or more statistical analysis methods, machine learning techniques, empirically-derived data, and combinations of the foregoing. In some examples, the speech recognition program 120 may utilize one or more probabilistic models to analyze portions of the speech recognition data 148, one or more results extracted from the speech recognition analysis pipeline, and/or estimated confidence values 152 associated with such portions. For example, GMMs may be utilized to analyze portions of the speech recognition data 148 and corresponding results. It will be appreciated that any other suitable machine learning techniques, such as various supervised learning and unsupervised learning approaches, may be utilized to analyze the speech recognition data 148.

It will be appreciated that the foregoing descriptions of speech recognition techniques are merely examples, and that any suitable speech recognition technologies and processes may be utilized and are contemplated within the scope of the present disclosure.

With reference again to FIG. 2, in some examples the voice listener 30 may receive context information including associated confidence values from entity tracker 100. As described in more detail below, entity tracker 100 may determine an identity, position, and/or current status of one or more entities within range of one or more sensors, and may output such information to one or more other modules, such as voice listener 30, commitment engine 60, etc. In some examples, entity tracker 100 may interpret and evaluate sensor data received from one or more sensors, and may output context information based on the sensor data. Context information may include the entity tracker's guesses/predictions as to the identity, position, and/or status of one or more detected entities based on received sensor data. In some examples, the guesses/predictions may additionally include a confidence value defining the statistical likelihood that the information is accurate.

Additional details regarding components and computing aspects that may be used to implement voice listener 30 are described in more detail below with respect to FIG. 27.

With continued reference to FIG. 2, the voice listener 30 may send recognized text and corresponding confidence values to the parser 40. As described in more detail below, the parser 40 analyzes the text and confidence values to determine an intent of the user in speaking the received utterance. The parser 40 may translate the natural language text received from the voice listener 30 into a machine-executable language that represents a user's intention underlying the natural language.

In some examples, a user's intention may correspond to a command to be executed immediately, such as the utterance "Play song A by artist B" (a "Play music" intent). In some examples, an intent may be characterized as a commitment to execute an action upon the occurrence of a trigger, hereinafter referred to as an "add commitment" intent. For example, the utterance "When Bob gets home remind him to take out the trash" is an add commitment intent. In this example, the trigger is Bob arriving home, and the action is to remind him to take out the trash. Another example of an add commitment intent may be the utterance "When Keith is near the oven, alert me." In this example, the commitment of this add commitment intent comprises a trigger (Keith is near the oven) and an action (alert me) to be executed when the trigger is detected. Additional descriptions and examples of commitments are provided below.

In some examples the parser 40 may utilize a plurality of intent templates that each contain a plurality of slots that may be filled with words or terms received from the voice listener 30, or with words or terms that are based on other words received from the voice listener. In some examples where one or more slots are not filled, the parser 40 may fill these slots by examining a semantic meaning of one or more other words. For example, the intelligent digital assistant system 20 may tell a user, "You have 15 emails." The user may respond with an utterance, "OK, I'll go through them when I'm in the car." In response to the user's utterance, the parser 40 may fill a "commitment type" slot with the type "reminder", even though the word "reminder" itself was not in the user's utterance.

Taken together, the plurality of slots of an intent template define or otherwise characterize the intent of the user in speaking an utterance. In various different examples, the slots may comprise an action slot, a trigger slot, a commitment slot, a subject slot, a content slot, an identity slot, and various other types of slots. In some examples, each slot may embody one of three states: (1) missing information, (2) information present with unresolved ambiguity, and (3) information present with any ambiguity resolved.

In some examples, one or more slots may be optional slots that need not be filled. For example, in one scenario two slots may represent optional information, while in another scenario the same two slots may represent required information. For example, the utterance "Play music" may be understood as a command that music should be played out of the device being used for this conversation. In this manner, the system infers information regarding the user's intention (to play music via the device being used for the conversation) without requiring the user to explicitly state this information. In a different example, the utterance "Whenever it's Eve's birthday, play Happy Birthday" will require the user to specify the device to use, since the play music action is scheduled to be performed some time in the future whenever the specified condition is met.

Figure 4:
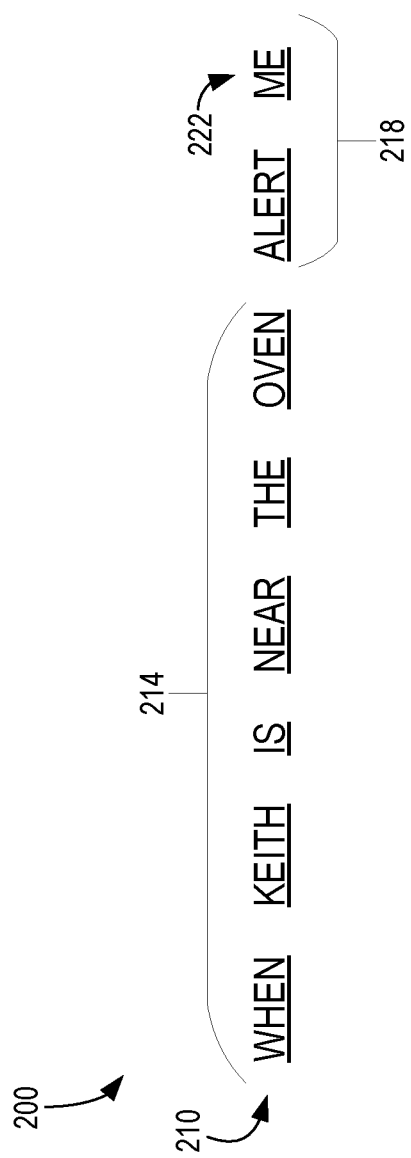
FIG. 4 shows of an intent template according to an example of the present disclosure.

One example of an intent template is a commitment intent template that corresponds to an add commitment intent. With reference now to FIG. 4, one example of a commitment intent template 200 is illustrated. In this example, the parser 40 may receive text phrase 210 from the voice listener 30 that reads "When Keith is near the oven alert me." The phrase "When Keith is near the oven" may be identified as a trigger 214. The phrase "alert me" may be identified as an action 218 that is to be carried out when the trigger is detected. As described in more detail below, in some examples the parser 40 may translate this text phrase 210 into machine-executable language that is passed to the intent handler 30 for further processing.

As noted above, the parser 40 may receive accuracy confidence values from the voice listener 30 that denote a likelihood that corresponding text is accurate. In some examples and as described in more detail below, the intent handler 50 also may receive entity confidence values that are associated with entity information. In some examples, such entity confidence values and other context information may be received via the entity tracker 100.

In the present example, the word "me" in phrase 210 fills a subject slot 222. In this example, the subject slot 222 corresponds to the person or other entity to be alerted when the trigger is detected. The word "me" may be received by the parser 40 with context information that associates this word to a particular person named Joe, and with an entity confidence value, such as 90%, that denotes a level of certainty that "me" is the person "Joe."

In some examples, the intended meaning of one or more words in an intent template may not be readily apparent. For example, in phrase 210 the meaning of the word "near" may be ambiguous, as "near" is a relative term. A variety of contextual factors may influence the intended meaning of "near" and the corresponding distance contemplated in this phrase. For example, where "Keith" is an infant, the intended meaning of "near" may be based on important safety concerns of the user speaking the phrase. Where "Keith" is the husband of the user, the intended meaning of "near" may be influenced less by safety concerns and more by convenience factors, which may lead to an associated distance that is different from the case where "Keith" is an infant. In another example, the distance intended to be conveyed in the phrase "near the oven" is likely different from the distance intended to be conveyed in the phrase "near the Statue of Liberty."

Accordingly, one or more words in an intent template may be ambiguous as passed to the intent handler 50. As described in more detail below, the intent handler 50 may utilize a plurality of techniques to resolve ambiguities and to fill in slots with missing information in an intent template.

In another example, the parser 40 may receive the text phrase "Play music with Fred" from the voice listener 30. In some examples, the phrase "Play music" is often interpreted to mean that a user wants to play digital music files via a media player. However, the use of the phrase "with Fred" following "Play music" is unusual, as people typically would not use this phrasing when their intent is to play music via a media player. The parser 40 may recognize this ambiguity and may generate a list of N-best intent templates that it determines are the statistically most probable intent templates corresponding to the user's actual intent. In some examples, the intent handler 50 may use additional context information to select an intent template from the list of N-best intent templates.

In another example, the text phrase received from the voice listener 30 may be the single word "Play." For example, the word or words spoken by the user after "Play" may have been unintelligible to the voice listener for one or more reasons (such as loud noises in the background). In this example, the parser 40 may predict that the user's intent is to play digital music, but in the corresponding intent template the content slot representing what music to play is empty. In this example, the parser 40 may send a "Play music" intent template to the intent handler 50 for further processing and resolution of this ambiguity, as described in more detail below.

In some examples, the parser 40 may analyze received text to form a decision tree of the user's intent. In some examples, the parser 40 may generate If-Then statements (or rules) from the received text. Each If-Then statement may comprise a corresponding trigger and an action. Whenever the conditions of the trigger are satisfied, the action is performed. The resulting If-Then statements can perform a wide variety of tasks, such as home security ("text me if the motion detector in the back yard is activated"), home automation ("turn on the fireplace when I arrive home"), personal organization ("collect my email receipts for charitable donations into a spreadsheet"), health-related tasks ("remind me to eat protein if I run more than 7 miles"), and many others.

In some examples, triggers and actions may be drawn from a range of channels that may be activated by a user. These channels may represent different entities and services, including devices (such as smart phone operating systems, connected home components such as smart light switches, etc.), knowledge sources (such as entertainment websites, email providers, etc.), and the like. Each channel may expose a set of functions for both the trigger and the action.

For example, If-Then statements may take the form of "IF [Input(s)] are recognized, THEN perform [Action(s)]". For example, the received phrase "When Oz is in the kitchen, tell him to take out the garbage" may be translated to the following If-Then statement: "IF the person Oz is determined to be in the kitchen, THEN broadcast a message to the person Oz to take out the garbage." In some examples, the parser 40 may determine that a user intends to establish a recurring a message or action based on parsing a received utterance. For example, in the phrase "When Oz is in the kitchen, tell him to take out the garbage," the word "when" may be interpreted by the parser 40 to designate that the corresponding action should be performed each time the condition is met (i.e., each time Oz is in the kitchen, tell him to take out the garbage). In another example, in the phrase "If Oz is in the kitchen, tell him to take out the garbage," the word "if" may be interpreted to designate that the corresponding action should be performed one time only (i.e., the next time Oz is in the kitchen, tell him to take out the garbage).

In some examples and as noted above, these If-Then statements may be generated probabilistically. In this manner and for a given string of text, the parser 40 may generate a plurality of N-best candidates of If-Then statements that may correspond to the user's utterance.

In some examples of parsing If-Then rules, the parser 40 may utilize a meaning representation that comprises an abstract syntax tree (AST) in a very simple language. For example, each root node may expand into a "trigger" and "action" pair. These nodes in turn expand into a set of supported triggers and actions. These trees may be modeled as a nearly context-free grammar that generates If-Then tasks. Additional description of semantic parsers for If-Then statements is provided in the following publications: "Language to Code: Learning Semantic Parsers for If-This-Then-That Recipes", authored by Chris Quirk, Raymond Mooney, and Michel Galley, *Proceedings of the 53$^{rd}$ Annual Meeting of the Association for Computational Linguistics*, pages 878-888, Beijing, China, Jul. 26-31, 2015, the entirety of which is incorporated herein by reference; and "Improved Semantic Parsers For If-Then Statements" authored by I. Belagy and Chris Quirk, *Proceedings of the 54$^{th}$ Annual Meeting of the Association for Computational Linguistics*, pages 726-736, Berlin, Germany, Aug. 7-12, 2016, the entirety of which is incorporated herein by reference. Additional descriptions of techniques for modeling relation paths in embedding models for knowledge bases and text are provided in "Compositional Learning of Embeddings for Relation Paths in Knowledge Bases and Text", authored by Kristina Toutanova, Xi Victoria Lin, Wen-tau Yih, Hoifung Poon, and Chris Quirk, available at https://www.microsoft.com/en-us/research/wp-content/uploads/2016/06/acl2016relationpaths-1.pdf, Jun. 19, 2016, the entirety of which is incorporated herein by reference.

In some examples, the parser 40 may use an ensemble of two techniques to generate If-Then statements and/or derive an intent from the text received from the voice listener 30: (1) a recurrent neural network (RNN) architecture in the form of a long short-term memory (LSTM) network, and (2) a logistic regression model. In some examples, a graph long short term memory (graph LSTM) neural network may be utilized to extract from received text semantic meanings and relationships between words that are inherent to natural language. For example, text may be parsed using a graph LSTM neural network to extract cross-sentence n-ary relationships using several graph LSTM units arranged according to the syntactic relations of terms in the segment of text. These syntactic relationships between words may be tracked in the graph LSTM neural network to allow artificial intelligence and machine learning techniques to identify entities and their context within the text and from the grammatical structure in which they exist.

For example, context that identifies the nouns to which pronouns refer, the adverbs that modify given verbs, the prepositional phrases that affect a given word, etc., may be incorporated into the various words to enable more accurate searches of the contents of natural language documents. Additional descriptions of and examples of using graph LSTM neural networks to extract semantic meanings and relationships between words are provided in U.S. patent application Ser. No. 15/395,961, entitled GRAPH LONG SHORT TERM MEMORY FOR SYNTACTIC RELATIONSHIP DISCOVERY, filed on Dec. 30, 2016, the entire contents of which are incorporated herein by reference.

In some examples, the parser 40 may receive and process text to graph nodes (e.g., words, phrases, characters, etc.) and edges (e.g., dependency links between nodes) in individual phrases and across boundaries of phrases. In various examples, the graphing may include identifying one or more links (e.g., syntactic, semantic, co-reference, discourse, etc.) between nodes in the text. The links can include intra-phrase and inter-phrase links between nodes. For example, a link can represent a relationship between the root of one phrase and the root of an adjacent phrase. For another example, a link can represent a relationship between two words in a phrase, such as the modifier "Annie's" to the word "lunch." Additional details regarding graphing nodes and edges in phrases and across boundaries of phrases is disclosed in U.S. patent application Ser. No. 15/173,349, entitled RELATION EXTRACTION ACROSS SENTENCE BOUNDARIES, filed on Jun. 3, 2016, the entire contents of which are incorporated herein by reference.

Additional details regarding components and computing aspects that may be used to implement parser 40 are described in more detail below with respect to FIG. 27.

As described above, in some examples the parser 40 passes an intent template to the intent handler 50 for further processing. The intent handler 50 comprises a multi-step pipeline that may resolve ambiguous information and/or information that is missing from an intent template. As described in more detail below, the intent handler 50 may utilize a plurality of techniques to resolve ambiguities and fill in missing information slots with respect to an intent template. In some examples, the intent handler 50 may utilize domain-specific information and domain-specific reasoning to resolve ambiguities, complete missing information, and otherwise clarify an intent template to more closely correspond to the actual intent of the user.

In some examples, the intent handler 50 may glean knowledge regarding the user's intent by analyzing prior utterances of the user in a conversation history, and may utilize such insights to resolve ambiguities and add missing information to an intent template. Once the intent handler 50 has sufficiently clarified ambiguities and completed missing information, a corresponding commitment may be generated and passed to the commitment engine 60 for execution.

The intent handler 50 may be configured to process multiple intent templates that may comprise a conversation. For purposes of the present disclosure and as described in more detail below, a conversation may comprise a plurality of information and other data related to one or more exchanges between the user and the intelligent digital assistant system 20. In different examples, such information and data may comprise words and/or phrases spoken by a user, queries presented to the user by the intelligent digital assistant system 20, sensor data received from one or more sensors, context information such as person and/or identity information, etc.

As described in the use case examples provided below, the intent handler 50 may comprise a plurality of resolvers that translate intent templates and their associated data received from the parser 40 into internal data references. To address slots that comprise missing and/or unresolved information in an intent template, the intent handler 50 may utilize the plurality or resolvers in a multi-stage process. In some examples, each of the resolvers may be specifically programmed to handle issues associated with a particular intent template that may be received from the parser 40.

Examples of resolvers may include lookup resolvers that translate proper names, aliases, and other identifiers into internal representation data (for example, "Bob" is translated to an internal representation of the person "Bob", such as Bob's contact information). Examples of resolvers may include anaphoric resolvers that address expressions having an interpretation that depends upon an antecedent or postcedent expression in context (for example, "she" is translated to a slot representing "a personal identity of the pronoun 'she'"), and deixis resolvers that address words and phrases, such as "here" or "there", that cannot be fully understood without additional contextual information (for example, "there" may translated to a slot representing "where is there?"). In other examples, many other forms and types of resolvers may be utilized.

Figure 5:
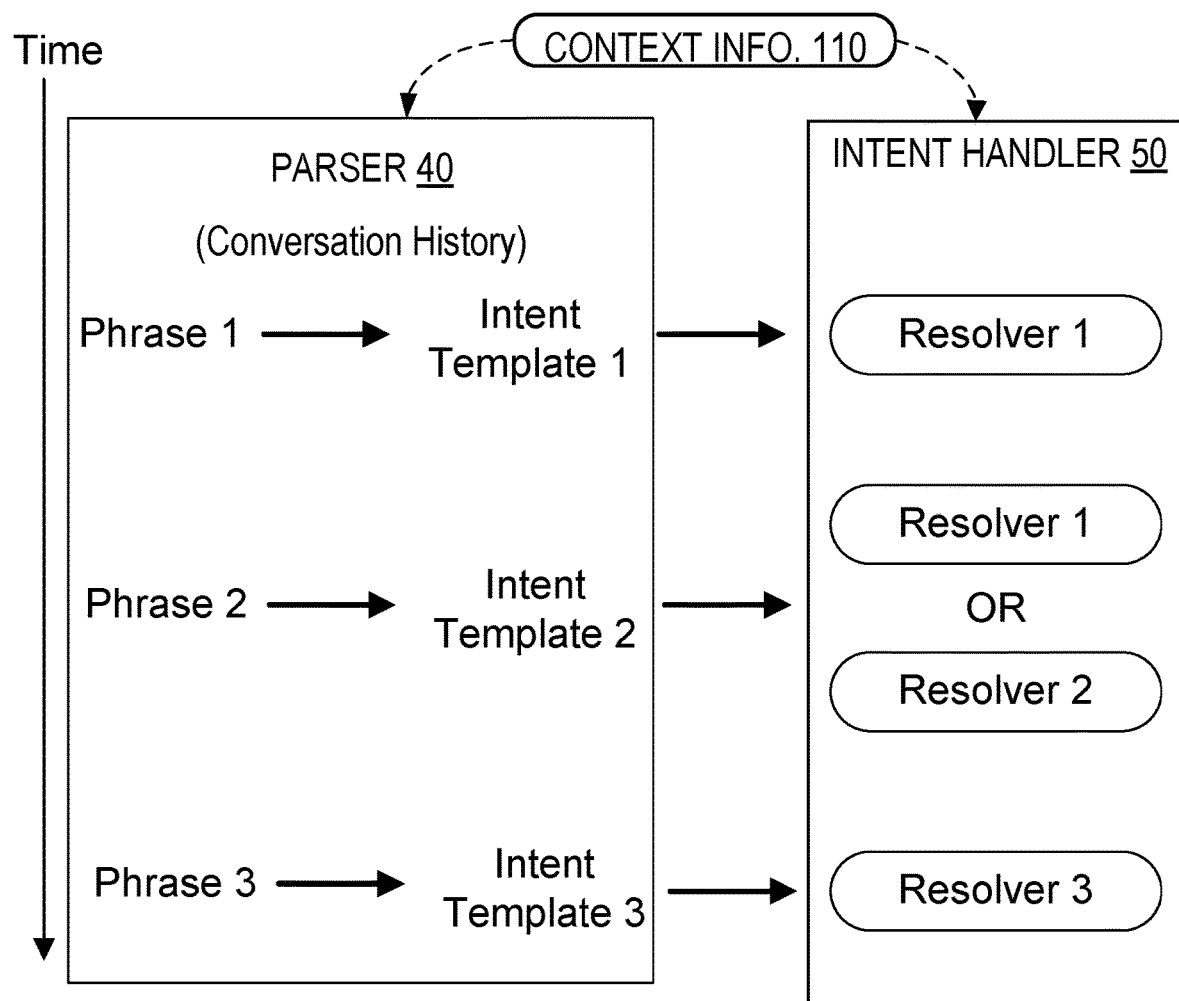
FIG. 5 schematically shows a parser and an intent handler processing a portion of a conversation according to an example of the present disclosure.

With reference now to FIG. 5, one example of the parser 40 and intent handler 50 processing a portion of a conversation is schematically illustrated. In this example, a first phrase 1 is parsed by the parser 40 into an intent template 1. The parser 40 provides intent template 1 to the intent handler 50, which utilizes a first resolver 1 to resolve ambiguities and/or missing information in this intent template. A second intent template 2 corresponding to a second phrase 2 is received from the parser 40. As described in more detail below, the intent handler 50 may analyze the intent template 2 along with context information 110 to determine whether to utilize first resolver 1 or second resolver 2 to resolve the intent template 2. A third intent template 3 based on a third parsed phrase 3 may then be received by the intent handler 50. The intent handler 50 may utilize a third resolver 3 to resolve intent template 3. Additional details and use case examples of analyzing intent templates with resolvers are provided below.

In some examples the intent handler 50 may determine whether two or more intent templates should be fused or merged together to continue with an existing conversation path. If the intent handler 50 determines that the two or more intent templates should be fused together, then the intent handler may fuse the data associated with the two or more intent templates and continue following the existing conversation path with the fused data. If the intent handler 50 determines that the two or more intent templates should not be fused together, then a new topic may be started using the most recently received intent template.

As described in more detail below, where a slot of an intent template has missing information, the intent handler 50 may perform data gathering operations (such as to ask the user to clarify or provide information, or try to gather the information in another way) in order to populate information in the slot. Once each slot contains information, the intent handler 50 may determine if the information in each slot is unambiguous. For information identified as ambiguous, the intent handler 50 may apply one or more of a variety of techniques to resolve the ambiguity.

With reference again to FIG. 2, in some examples the intent handler 50 may comprise a mapper 52 that maps one or more system goals to a corresponding user intent(s). Examples of system goals may include clarifying ambiguities, acquiring additional information from a user, etc. In some examples, mapper 52 may internally rephrase system goals as user intents or goals. For example, mapper 52 may map information the system needs, such as information to resolve an ambiguous intent, to a user intent that the user would have triggered in providing that information. In other words, mapper 52 may map information to the intent that would have been resolved from an utterance that a user would have spoken in order to generate the intent. In some examples, mapper 52 may map a system goal to a word or phrase the user would have said to generate the same outcome.

In some examples, where the system needs information from a user to resolve a user intent, the system may internally cue a state that is equivalent to the state the system would have been in if the user had provided input (such as an utterance) containing all the components of the intent except for the needed information. In other words and in some examples, the system may assume that the user has already provided more input, with that input missing only one or more specific slot(s) corresponding to the needed information. In this manner, the intent handler 50 may continually utilize whatever user input is provided. In some examples, this allows the system to reuse components, such as intent templates. Accordingly and in these examples, by causing the intent handler 50 to assume that user intents (versus system goals) are driving its operation, the system may internally reuse corresponding logic and may understand such user intents with greater depth and richness.

In some examples, the system may have a goal of acquiring information from a user to proceed with deriving a user intent. In a first example, a user may speak two utterances: "Book me a flight to California tomorrow; The flight needs to be to San Francisco." In the first utterance, the user indicates an intent to book a flight, and in the second utterance the user narrows the intent to a flight to San Francisco. In both utterances, a user intent is specified.

In another example, the user speaks a first utterance "Book me a flight tomorrow." The system may respond with a query "Where do you want to fly to?" The user may then respond, "To San Francisco." Upon generating the system query, the mapper 52 may map the intent handler's goal (acquiring information of the user's destination) to a user intent. For example, the mapper 52 may presume that the user is about to provide this information as if it were the user's intent.

In some examples, by configuring the mapper 52 to presume that a user intent is driving its operation, the system may minimize the code to perform these operations and reuse corresponding logic. In this manner, the system may understand such user intents with greater depth and richness. Accordingly, in these examples the system may utilize code for the intent handler 50 and mapper 52 that comprises a user-intent only system, as opposed to utilizing multiple specialized pieces of code to manage all ambiguities and otherwise handle multiple corresponding tasks and discrete situations.

Additional details regarding components and computing aspects that may be used to implement intent handler 50 are described in more detail below with respect to FIG. 27.

Figure 6A:
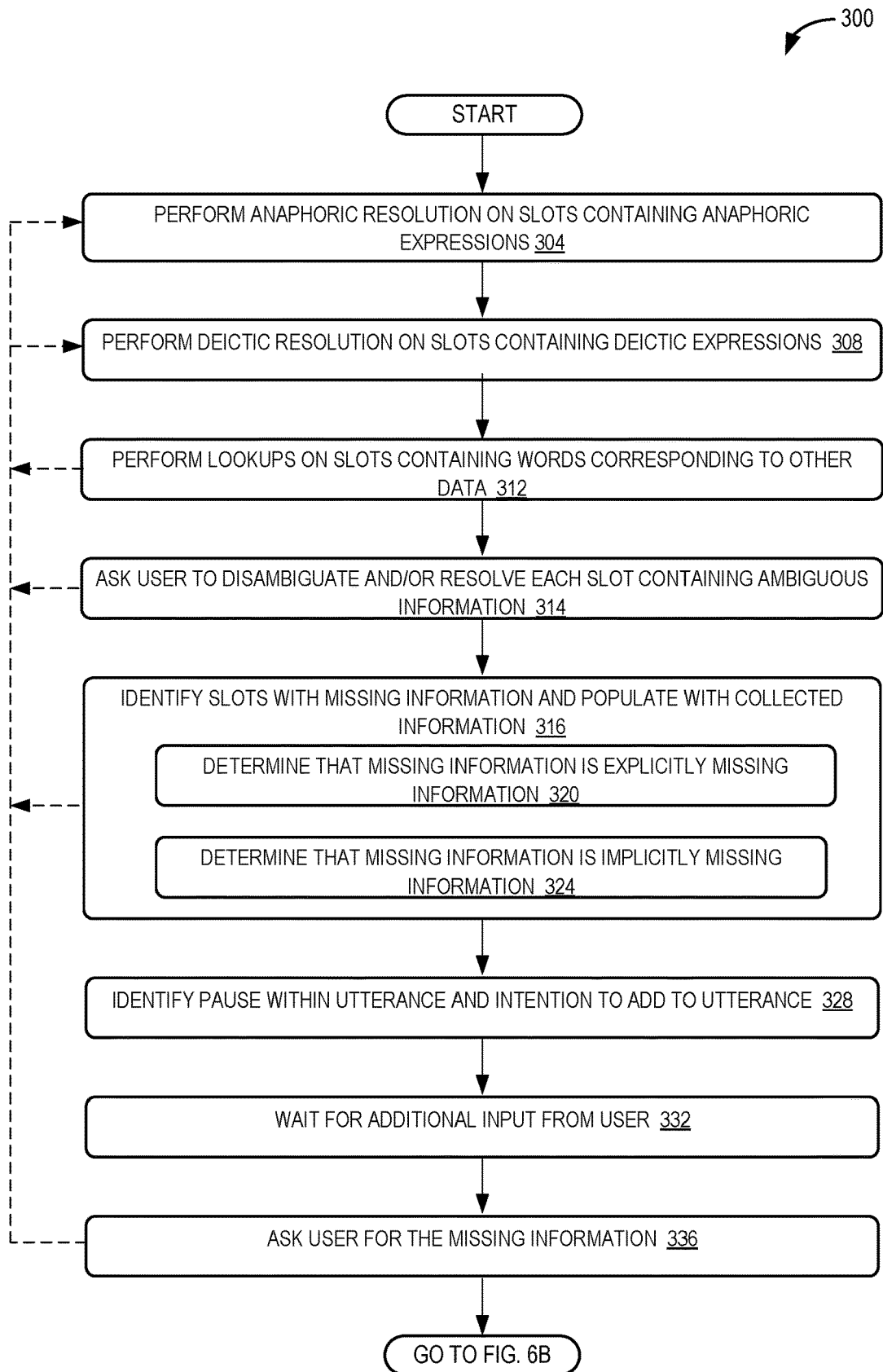
FIGS. 6A and 6B show a method for addressing missing and/or unresolved information in an intent template according to examples of the present disclosure.
Figure 6B:
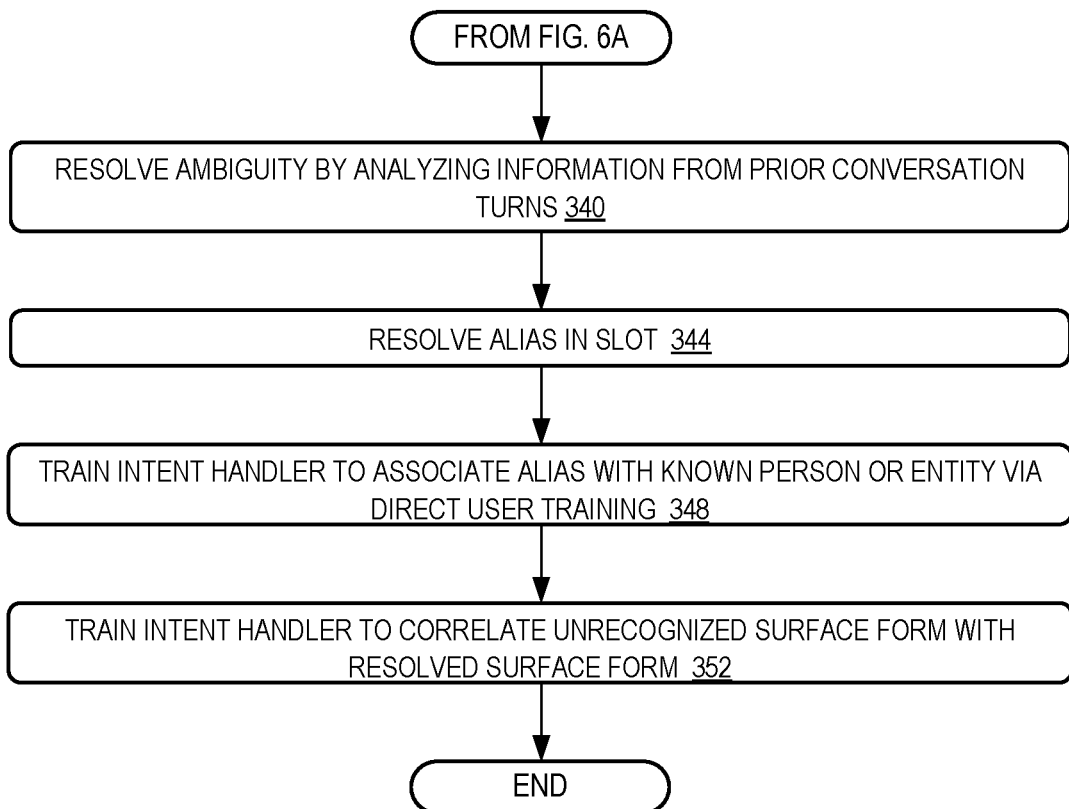

With reference now to FIGS. 6A and 6B, a flow chart of a method 300 for addressing missing and/or unresolved information in an intent template according to examples of the present disclosure is provided. The following description of method 300 is provided with reference to the software and hardware components described herein. It will be appreciated that method 300 also may be performed in other contexts using other suitable hardware and software components.

Additionally, while the blocks of method 300 are described and illustrated in a particular sequence, in different examples the order of execution may vary. In some examples one or more of the blocks may not be performed. In some examples, context information 110 from the entity tracker 100 may be utilized to determine an order of execution and/or which block to execute next.

With reference to FIG. 6A, at 304 the method 300 may include performing anaphoric resolution on slots that contain an anaphor or a cataphor. For example, in the phrase "When he is near the oven alert me", the word "he" is an anaphoric expression that refers to a person who was referenced earlier in the conversation. Additionally and as described in more detail below, by understanding and resolving the intent of the user via intent template(s) received from the parser 40, the intent handler 50 may augment this anaphoric resolution process with one or more other techniques, such as grounding and repair techniques described in more detail below, to more accurately determine the person who corresponds to an anaphoric expression.

At 308 the method 300 may include performing deictic resolution on slots that contain words that cannot be fully understood without additional contextual information. Examples of deictic expressions include words having a fixed semantic meaning and a denotational meaning that varies depending on time and/or place. For example, in the phrase "When he is near the oven alert me", the word "near" is a deictic expression whose meaning depends on contextual information. Additionally and as with anaphoric expressions, the intent handler 50 may augment its deictic resolution process with one or more other techniques, such as grounding and repair techniques, to clarify the intended meaning of the deictic expression.

In some examples, deictic resolution may be performed using data from one or more sensors, such as captured image data, audio data, position information, etc. For example, when a user points at an oven, image data showing the user's finger pointing at the oven may utilized by the entity tracker 100 to identify the oven and to determine that the user is pointing at the oven. While pointing the user may speak the utterance "Let me know when this gets hot." Using this information, the intent handler 50 may resolve the word "this" into "oven", and more particularly into the oven at which the user is pointing.

In another example, a user may speak "If my child comes in here let me know." The system may use location data of the user to resolve the word "here" into the current location of the user. In another example, two people walk into the room, and one person asks the system: "Do we have any messages?" Using sensory information, such as image data and/or audio data to identify both people, the system may perform deictic resolution to resolve "we" to the identities of the two people in the room.

At 312 the method 300 may include performing lookups for slots containing words that correspond to other data available to the intent handler 50. Examples of other data that may be available to the intent handler 50 include contact information, social graph data, calendar information, email data, photo metadata, and the like. Information accessed in performing such lookups may be populated in a slot to replace the word(s) presently occupying the slot. For example, in the phrase "Tomorrow remind me to drop the car at autodealer1", the word "autodealer1" may correspond to the auto repair shop where the user regularly has her car repaired. "Autodealer1" may be represented by a contact entry in the user's contact database. Accordingly, the intent handler 50 may locate such contact entry and may utilize the "Autodealer1" contact data for the word "autodealer1" in the intent template.

At this point, the method 300 may return to 304 and/or 308 to perform anaphoric resolution and/or deictic resolution, as needed, on information populated in a slot. Additionally, the intent handler 50 may augment its lookup process with one or more other techniques, such as grounding and repair techniques, to clarify the intended person or entity that corresponds to the information currently present in the slot.

At 314 the method 300 may include asking the user to disambiguate and/or resolve one or more slots containing ambiguous information. For example, where a user asks the system to "Call Patrick", and the user's contacts database includes a Patrick Doe and a Patrick Smith, the system may ask the user, "Which Patrick would you like to call, Patrick Smith or Patrick Doe?"

At 316 the method 300 may include identifying slots with missing information and populating these slots with collected information. Various techniques may be utilized to generate and/or retrieve such information. For example and as described in more detail below, slots with missing information may be treated differently depending upon whether the information is determined to be explicitly missing or implicitly missing.

For example, at 320 the method 300 may include determining that the missing information is explicitly missing information. In one example, by analyzing a text phrase the intent handler 50 may determine that the user's utterance suggests that information for a particular slot should be provided in the utterance. Where such information is missing, the information may be determined to be explicitly missing information. For example, consider the phrase "When Bob comes into the room with the others introduce." The intent handler 50 may determine that this phrase comprises a content slot corresponding to the subject of the verb "introduce", and that this content slot is missing information. In this example, the context of the phrase comprises the words that precede "introduce", these words' order and meaning, the factor that the phrase ends with the word "introduce" without naming the subject of the introduction, and the factor that the phrase constitutes a grammatically incomplete sentence.

The intent handler 50 may determine that this context does not resolve the ambiguity associated with this missing information. For example, while the user may be intending to introduce Bob to the others, other intentions are also possible (such as introducing one of the others to Bob). Accordingly, the intent handler 50 determines that the ambiguity associated with this missing information cannot be presently resolved. Given this ambiguity and as described in more detail below, the intent handler 50 may use one or more other techniques (such as querying the user, "Whom do you want to introduce?") to collect the missing information. In some examples as described in more detail below, the intent handler 50 may wait for the receipt of additional user input before querying the user. In some examples, additional information from the entity tracker 100 may be utilized to resolve the ambiguity and collect the missing information.

In some examples, where information for a trigger slot or an action slot of a commitment is missing, and based at least in part on context information 110 generated by the entity tracker 100, the intent handler 50 may proactively propose an action to the user. In one example, a user may speak the utterance "Alice." The intent handler 50 may receive an intent template with an empty action slot and a trigger slot partially completed with the name "Alice." The context information 110 may include an identity prediction with 85% confidence that "Alice" corresponds to the "Alice Jones" in the user's contact database. The context information 110 also may include a location prediction with 95% confidence that Alice Jones is located in the basement laundry room of the user's house. Based at least in part on this context information 110, the intent handler 50 may proactively ask if the user would like to communicate with Alice Jones, such as via an in-home intercom system.

At 324 the method 300 may include determining that the missing information is implicitly missing information. In one example, the intent handler 50 may determine that a user did not intend to provide information that is missing from a particular slot. Such missing information may be determined to be implicitly missing information. For example, consider the phrase "When Bob walks into the kitchen say Hello." The intent handler 50 may determine that the command "say Hello" corresponds to the user saying Hello to another person. Accordingly, the intent template corresponding to this phrase may comprise a content slot that follows the words "say Hello" and which normally contains the name or other identifier of the person the user intends to say Hello to (e.g., "Say Hello to Suzanne").

In this example, because the phrase ended with the word "Hello", such content slot is missing information that identifies the person intended. The context of this phrase comprises the words that precede "Hello", these words' order and meaning, and the factor that the phrase constitutes a grammatically complete sentence. Given this context, the intent handler 50 infers that the user intends for the command "say Hello" to apply to Bob. In other words, the context associated with this phrase indicates that the content slot following the words "say Hello" should be filled with "Bob." In this manner, the intent handler 50 may resolve this particular ambiguity associated with the missing information without querying the user for additional input. After populating a slot with missing information as described above, the method 300 may return to 304 and 308 to perform anaphoric resolution and/or deictic resolution, as needed, on the information populated in the slot.

In some examples and as noted above, the intent handler 50 may query the user for information that is missing from a slot. For example, the intent handler 50 may broadcast a spoken word query to the user via a speaker of a mobile phone. In some examples, however, information missing from a slot may be the result of an intended or unintended pause by the user that interrupts the user before the user completes her utterance. Accordingly and at 328, in some examples the method 300 may include identifying a pause within an utterance from a user along with an intent of the user to continue speaking and add to the utterance.

For example, a user may pause mid-utterance to think about what she should say next. In other examples, a user may be interrupted mid-utterance by an external event, such as another person speaking, distracting activity from the user's environment such as a loud noise or bright light, or a variety of other external activities.

In one example and with reference to the description above for identifying explicitly missing information, the phrase "When Bob comes into the room with the others introduce" may be determined to comprise a content slot that corresponds to the subject of the verb "introduce" and is missing information. Based on the empty content slot, other aspects of the phrase, and/or the context in which it is spoken, the intent handler 50 may identify a pause at the end of this phrase along with a predicted intent of the user to continue speaking and to add a subject to the verb "introduce."

At 332 and in response to identifying the pause, the method 300 may include waiting for additional input from the user before asking the user for more information. In some examples, the intent handler 50 may wait for a predetermined period of time, such as 1 second, 2 seconds, or other length of time that does not create a negative user experience for the user. In this manner, the system may avoid interrupting the user mid-utterance where the user intends to begin speaking again and to add to the utterance.

In some examples, an engagement timer may be started whenever a user starts speaking. The engagement timer may run for a predetermined period of time during which the user may be designated as "engaged." The predetermined period of time may be 1 second, 2 seconds, or other duration. If the system needs to ask for input or otherwise audibly converse with the user before the predetermined period of time expires, the system may use interruption language constructs that may provide for a more gentle interruption of the user's current potential engagement. Examples of interruption language constructs include "by the way" and "additionally". In some examples, such language constructs may be used even where the user has stopped speaking and/or the current conversation has "timed out," and the system is not presently listening to the user.

At 336 the method 300 may include querying the user for information missing from a slot. In some examples, the intent handler 50 may ask the user for information missing from one or more slots of an intent template. For example, regarding the phrase "When Bob comes into the room with the others introduce" and its explicitly missing information in the content slot following the word "introduce," the intent handler 50 may broadcast a spoken word query to the user asking "Whom do you want to introduce?" In other examples, the intent handler 50 may query the user via other interfaces, such as by displaying a query on a display device.

When the intent handler 50 receives a response to its query from the user (via the voice listener 30 and parser 40), the intent handler may populate the slot with the response. At this point, the method 300 may return to 304 and the steps following to analyze this newly-added information for any ambiguities as described above.

With reference now to FIG. 6B, at 340 the method 300 may include resolving an ambiguity by analyzing information from a prior conversation turn. In different examples, the method may analyze both utterances as a single or combined utterance, and/or may use one or more elements from a prior utterance to generate one or more slots in an intent template for a current utterance.

In some examples, the intent handler 50 may analyze content from a previous intent template and/or one or more slots of the template. In some examples, the intent handle 50 may determine that a current utterance is additive to a previous utterance. For example, consider the phrase "When Justin is near the oven, alert Erich." Justin may be a toddler, Erich the toddler's father, and the user speaking the phrase may be Justin's mother. The intent handler 50 may receive a first intent template for this phrase. A first resolver may resolve the template and establish a commitment that broadcasts a warning to Erich via Erich's mobile phone when Justin is within 1 meter of the oven in Erich's kitchen.

After speaking this first phrase, Justin's mother may pause for a brief period of time, such as 3 or 4 seconds. After this pause, she may speak a second phrase "and me" which is received by the parser 40. As this phrase contains no action component, the parser 40 may generate a second intent template that has an unknown or unresolved intent. In this example, and because the intent associated with this second phrase is presently unknown, the intent handler 50 may select a second, different resolver to address this second intent template.

Based at least in part on this second phrase beginning with the conjunction "and" followed by the pronoun "me", the second resolver may determine that Justin's mother intends to refer to a prior utterance. The second resolver may utilize an anaphoric resolution technique to associate the word "me" to Justin's mother. By using this data and analyzing the previously-established commitment, the second resolver may determine that the intent associated with the second phrase "and me" is related to the intent associated with the prior phrase "When Justin is near the oven, alert Erich." Accordingly, the second resolver may modify the previously-established commitment to broadcast a warning to both Erich and Justin's mother when Justin is within 1 meter of the oven in the kitchen.

As another example, consider again the phrase "When Justin is near the oven, alert Erich." After speaking this first phrase, Justin's mother may pause for a few seconds and then speak a second phrase "and also if he's close to the pool." As this phrase contains a trigger ("if he's close to the pool") and no action component, the parser 40 may generate a second intent template that has an unknown or unresolved intent. Also, in this example the anaphoric expression "he's" could refer to either of the two names in the preceding phrase (Justin or Erich).

A resolver may determine that it is most probable that the reference to "he" in the trigger of the second phrase is intended to refer to a male person mentioned in another, prior trigger. Based at least in part on this second phrase beginning with the conjunction "and" followed by the words "also" and "if", the second resolver may determine that Justin's mother intends to refer to a prior utterance and to modify a trigger or add another trigger to an action of the previously-established commitment. By using this data and analyzing the previously-established commitment, the second resolver may determine that the intent associated with the second phrase "And also if he's close to the pool" is related to the intent associated with the prior phrase "When Justin is near the oven, alert Erich." Accordingly, the second resolver may modify the previously-established commitment to broadcast a warning to Erich when Justin is either within 1 meter of the oven in the kitchen or within 3 meters of the pool.

In some examples, the intent handle 50 may determine that a current utterance is intended to amend one or more previous utterances. For example, consider the phrase "Please remind me to call Jeff at six o'clock." After speaking this first phrase, the user may pause for a brief moment and then speak a second phrase "I mean Mike." As this phrase contains an ambiguous phrase without a clear trigger or action component, the parser 40 may generate another intent template that has an unresolved intent.

By analyzing the immediately preceding commitment associated with the prior utterance "Please remind me to call Jeff at six o'clock," a resolver may determine that the intent associated with the second phrase "I mean Mike" is most likely related to the intent associated with the prior phrase "Please remind me to call Jeff at six o'clock." Accordingly, this resolver may modify the previously-established commitment to replace the reference to "Jeff" in the action component of this phrase with "Mike."

In another example, consider the phrase "Please remind me to call Jeff and Mike at six o'clock." After speaking this first phrase, the user may pause for a brief moment and then speak a second phrase "not Mike." As this phrase contains an ambiguous phrase without a clear trigger or action component, the parser 40 may generate another intent template that has an unresolved intent.

By analyzing the immediately preceding commitment associated with the utterance "Please remind me to call Jeff and Mike at six o'clock," a resolver may determine that the intent associated with the second phrase "not Mike" is most likely related to the intent associated with the prior phrase "Please remind me to call Jeff and Mike at six o'clock." Accordingly, this resolver may modify the previously-established commitment to remove the reference to "and Mike" from the action component of this phrase.

In some examples and as described in more detail below, where two or more people are having a conversation, the system may follow the conversation and determine when the active participant (i.e., the person currently speaking) changes in the conversation. In these examples, when the system determines that the current speaker has changed, the system may determine whether the information contained in the new speaker's speech is a continuation of the existing conversation topic/session, or whether a new topic/session has been introduced. Where the new speaker's information is a continuation of the existing conversation topic/session, this determination may be used by the intent handler 50 to resolve ambiguities, complete missing information and/or otherwise clarify the intent of each speaker. For example, such conversation and topic/session tracking may enable the system to assist a team that is working and speaking collaboratively to complete a task. In some examples, the system may track multiple conversations that are occurring simultaneously or otherwise overlapping, and may interact with participants in each conversation as appropriate for each conversation.

In some examples, the intent handler 50 may determine that an intent associated with a newly received phrase is not related to the intent of an immediately preceding commitment. For example, an intent template corresponding to the utterance "Call Justin" may be received and processed by a first resolver into a first commitment. The first resolver may determine that the content slot ("Justin") of the action "Call Justin" is ambiguous because the user has both a Justin Smith and a Justin Doe in the user's contacts database. Accordingly, the first resolver may respond with a query to the user of "Which Justin—Justin Doe or Justin Smith?" In this example, the user responds with an unrelated response, "Please record TV Show A tonight."

The first resolver may analyze this response and its corresponding new intent template by referring to the immediately preceding intent template and its missing content slot. Because the user's response is completely unrelated to the query just presented to the user, the first resolver determines that the new intent template represents a new intent of the user, and thus the new intent template should not be fused with the preceding intent template. Accordingly, the first resolver is replaced by a second resolver that proceeds to analyze the new intent template and establish a new conversation.

At 344 the method 300 may include resolving an alias that refers to a known person or entity by a different name or representation. In one example, a user may refer to "Mimi" in an utterance. The user's contacts database may not contain a contact with the name "Mimi." However, in prior conversations tracked by the intent handler 50, the user's sister may have referred to herself as "Mimi" when speaking with her grandson. A data store accessible to the intent handler 50 may have created an association between the user's sister and the alias "Mimi." By searching the data store for instances of "Mimi" and finding the association between the user's sister and the alias "Mimi", the intent handler 50 may resolve the name "Mimi" in the user's utterance to the user's sister.

At 348 the method 300 may include training the intent handler 50 to associate an alias with a known person or other entity via direct user training input. For example, the user may speak a command, "When I say Mimi I'm referring to my sister Suzanne." The intent handler 50 may create a link between "Mimi" and the user's sister Suzanne, such as by modifying a contacts database file containing information identifying Suzanne.

In a similar manner, at 352 the method 300 may include training the intent handler 50 in a real-time or batch-mode manner to correlate an unrecognized surface form with a newly resolved surface form. For example, the intent handler 50 may be unable to recognize a particular surface form it receives. The intent handler 50 may clarify this surface form via one or more grounding and repairing techniques. In this manner and going forward, the unrecognized surface form subsequently may be correlated with the clarified surface form, whereby the intent handler 50 now may recognize the previously-unrecognized surface form.

In another example, a user may be traveling across New York City in a car for hire. The user may speak a first request to his smartphone, with a middle portion of the phrase unintelligible: "When I get to [unintelligible] call her mobile phone." By analyzing this phrase along with context information, such as motion data indicating the user is traveling in a car, the intent handler 50 may infer that the unintelligible portion of the phrase corresponds to a location slot.

The intent handler 50 may query the user, "Where do you want to do this?" The user may reply with a second response, "Madison." The parser 40 may receive the text "Madison" from the voice listener 30, and may generate a list of the statistically most probable meanings for this word that correspond to the user's actual intent. In this example, the user may have a close friend named Madison, and may have used her name in many spoken requests to the intelligent digital assistant system 20. Accordingly, the parser 40 may determine that the user's close friend "Madison" is the most probable intention underlying the user's utterance.

However, based its analysis of the user's first request and other context information, such as the motion data, the intent handler 50 determines that the expected user response to the query "Where do you want to do this?" most likely will be location information. The intent handler also may analyze mapping data that indicates the user will arrive at a Madison Avenue address in five minutes. Accordingly and based at least in part on this context information, the intent handler 50 may not select the user's close friend "Madison", despite the parser's prediction that this is the statistically most probable meaning for this word. Instead, the intent handler may use this context information to resolve this ambiguity by selecting Madison Avenue as the intention of the user.

In some examples where the intent handler is unable to resolve an intent from an utterance, the system may still offer to take one or more actions. For example, if a user makes the declarative statement "Silver looks nice", the system may not understand the user's intent underlying this utterance. Instead of ignoring the user because the system doesn't understand what it should do with the utterance, the system may offer to display photos of silver jewelry, play music, or take some other action.

It will be appreciated that method 300 is provided by way of example and is not meant to be limiting. Therefore, it is to be understood that method 300 may include additional and/or alternative steps relative to those illustrated in FIGS. 6A and 6B. Further, it is to be understood that method 300 may be performed in any suitable order. Further still, it is to be understood that one or more steps may be omitted from method 300 without departing from the scope of this disclosure.

As described above, when the intent handler 50 has sufficiently clarified and resolved the user's intent, a corresponding commitment may be generated and passed to the commitment engine 60 for execution. As described in more detail below, the commitment engine 60 may utilize one or more cost functions to determine one or more costs associated with executing or not executing a commitment and, in some examples, with outputting or not outputting a message to the user.

Where the commitment engine 60 receives multiple commitments, the commitment engine may prioritize the commitments for presentation to a user. In one use case example, the commitment engine 60 may be storing seven commitments for user Eddie, with each commitment set to convey a different message to Eddie. Each message also may be staged to be audibly broadcast to Eddie when he arrives home from work today. The commitments and corresponding messages may include task reminders to take out the garbage, fix the leaky faucet and put the roast in the oven, and informational reminders that property taxes are due tomorrow and that he needs to buy eggs. If each of these messages is broadcasted to Eddie when he walks in the door, he may be less likely to effectively manage and/or prioritize the corresponding tasks.

Additionally, in some examples Eddie's current context may make it more difficult for him to comprehend and effectively manage these messages. For example, if Eddie is talking on his phone when he walks in the door, and seven messages are audibly broadcast to him at that time, he may have difficulty hearing or even comprehending the messages.

Accordingly and in some examples, factors related to the receptivity of the user to receiving input, the importance of a commitment to a particular user, and/or the user's current context may be determined. Machine learning techniques may be applied to such factors and other data to learn from such information and make related predictions in the future. As described in more detail below, one or more cost functions may be used to determine costs associated with executing or not executing a commitment. Using these techniques, the commitment engine 60 may intelligently manage the execution of commitments and corresponding messages to align with a particular user's preferences and current context.

In some examples, and in response to changing contexts and/or new data inputs, the commitment engine 60 may modify priorities, timings, and other aspects of commitments, messages and their execution. For example and as described in more detail below, the commitment engine 60 may receive context information 110, such as entity identity, entity position, and entity status information, from the entity tracker 100. Such context information 100 may be used by commitment engine 60 to determine whether a particular message, notification, or commitment should be presented to a user or otherwise executed.

In some examples, one or more previously defined components of a commitment may be updated based on new input received by the commitment engine 60. For example, the intent handler 50 may generate and pass a commitment including a trigger component that refers to a separately-defined term. In one example, a user may speak the utterance: "Please notify my kids to come home 60 minutes before curfew." The term "curfew" may be associated with the user's profile that is stored in a data store, and may currently have a value of 11:00 pm. By accessing the user's profile stored in a data store, the intent handler 50 may resolve the term "curfew" to 11:00 pm, and may pass to the commitment engine 60 a corresponding commitment to send a text message at 10:00 pm (60 minutes before 11:00 pm) to the user's children with instructions to come home.

Subsequently to this utterance, the user may update her kids' curfew time to one hour later, such as by speaking: "Update the kids' curfew to Midnight." The commitment engine 60 may identify this update its modification to the value of "curfew," and may determine that it affects the previously-received commitment. Accordingly, the commitment engine may correspondingly modify the trigger of the previously-received commitment by updating the value of "curfew" to Midnight, which results in the commitment sending the text message at 11:00 pm instead of 10:00 pm. The commitment engine 60 also may modify the value of "curfew" in the user's profile stored in the data store.

Additional details regarding components and computing aspects that may be used to implement commitment engine 60 are described in more detail below with respect to FIG. 27.

Figure 7:
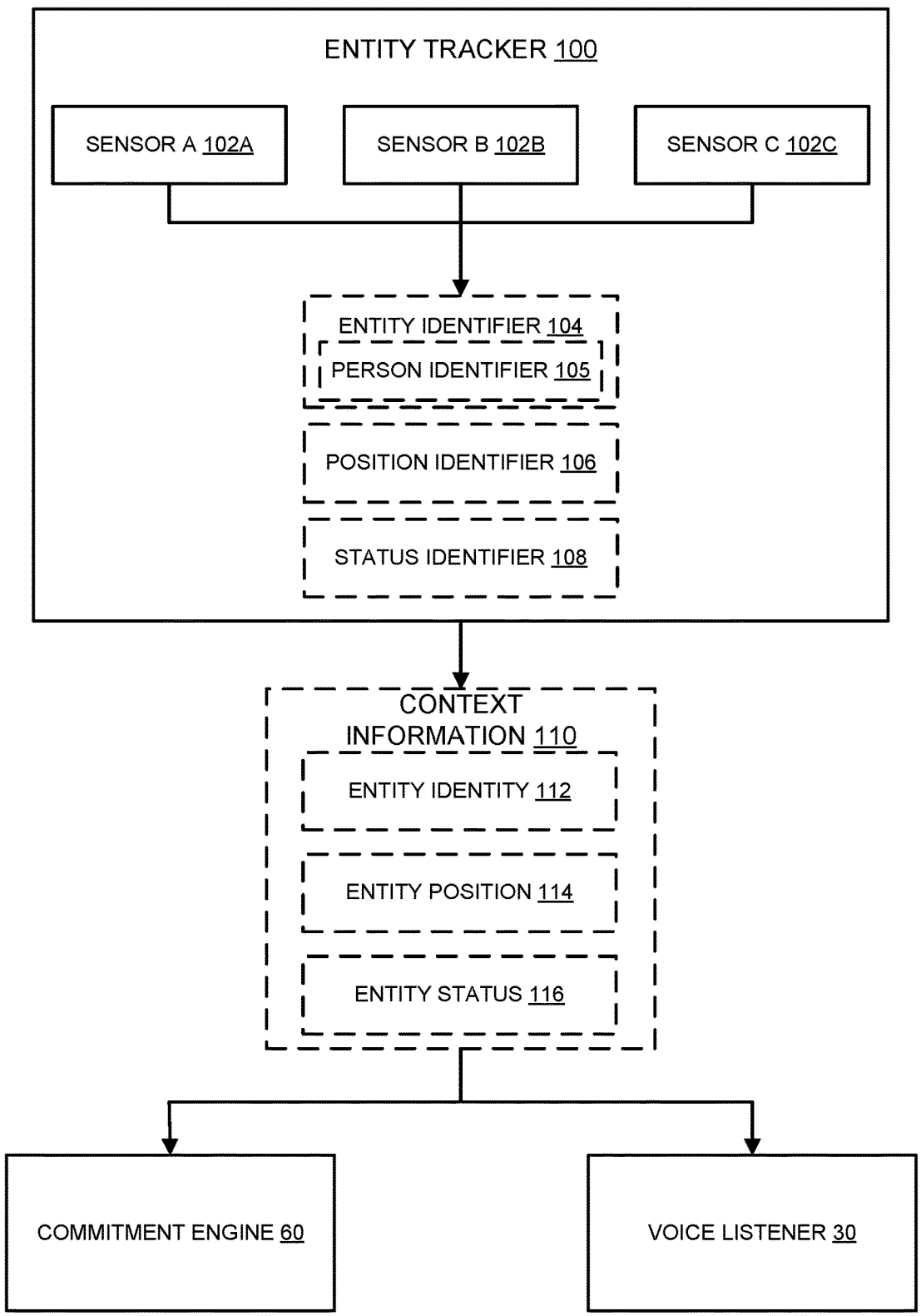
FIG. 7 schematically shows an entity tracker that may determine an identity, position, and/or current status of one or more entities according to examples of the present disclosure.

FIG. 7 schematically illustrates an example entity tracker 100 that may comprise a component of the intelligent digital assistant system 20. Entity tracker 100 may be used to determine an identity, position, and/or current status of one or more entities within range of one or more sensors. Entity tracker 100 may output such information to one or more other modules of intelligent digital assistant system 20, such as the commitment engine 60, voice listener 30, etc.

The word "entity" as used in the context of the entity tracker 100 may refer to people, animals, or other living things, as well as non-living objects. For example, the entity tracker may be configured to identify furniture, appliances, structures, landscape features, vehicles, and/or any other physical object, and determine the position/location and current status of such physical objects. In some cases, the entity tracker 100 may be configured to only identify people and not other living or non-living things. In such cases, the word "entity" may be synonymous with the word "person."

Entity tracker 100 receives sensor data from one or more sensors 102, such as sensor A 102A, sensor B 102B, and sensor C 102C, though it will be understood that an entity tracker may be used with any number and variety of suitable sensors. As examples, sensors usable with an entity tracker may include cameras (e.g., visible light cameras, UV cameras, IR cameras, depth cameras, thermal cameras), microphones, pressure sensors, thermometers, motion detectors, proximity sensors, accelerometers, global positioning satellite (GPS) receivers, magnetometers, radar systems, lidar systems, environmental monitoring devices (e.g., smoke detectors, carbon monoxide detectors), barometers, health monitoring devices (e.g., electrocardiographs, sphygmomanometers, electroencephalograms), automotive sensors (e.g., speedometers, odometers, tachometers, fuel sensors), and/or any other sensors or devices that collect and/or store information pertaining to the identity, position, and/or current status of one or more people or other entities. In some examples, the entity tracker 100 may occupy a common device housing with one or more of the plurality of sensors 102, and/or the entity tracker and its associated sensors may be distributed across multiple devices configured to communicate via one or more network communications interfaces (e.g., Wi-Fi adapters, Bluetooth interfaces).

As shown in the example of FIG. 7, entity tracker 100 may include an entity identifier 104, a person identifier 105, a position (location) identifier 106, and a status identifier 108. In some examples, the person identifier 105 may be a specialized component of the entity identifier 100 that is particularly optimized for recognizing people, as opposed to other creatures and non-living things. In other cases, the person identifier 105 may operate separately from the entity identifier 104, or the entity tracker 100 may not include a dedicated person identifier.

Depending on the specific implementation, any or all of the functions associated with the entity identifier, person identifier, position identifier, and status identifier may be performed by the individual sensors 102A-102C. Though the present description generally describes the entity tracker 100 as receiving data from sensors, this does not require that the entity identifier 104, as well as other modules of the entity tracker, must be implemented on a single computing device that is separate and distinct from the plurality of sensors associated with the entity tracker. Rather, functions of the entity tracker 100 may be distributed amongst the plurality of sensors. For example, rather than sending raw sensor data to the entity tracker, individual sensors may be configured to attempt to identify entities that they detect, and report this identification to the entity tracker 100, and/or other modules of intelligent digital assistant system 20. In some cases, this identification may include a confidence value.

Each of the entity identifier 104, person identifier 105, position identifier 106, and status identifier 108 is configured to interpret and evaluate sensor data received from the plurality of sensors 102, and to output context information 110 based on the sensor data. Context information 110 may include the entity tracker's guesses/predictions as to an identity, position, and/or status of one or more detected entities based on received sensor data. As will be described in more detail below, each of the entity identifier 104, person identifier 105, position identifier 106, and status identifier 108 may output their predictions/identifications along with a confidence value.

The entity identifier 104 may output an entity identity 112 of a detected entity, and such entity identity may have any suitable degree of specificity. In other words, based on received sensor data, the entity tracker 100 may predict the identity of a given entity, and output such information as entity identity 112. For example, the entity identifier 104 may report that a particular entity is a piece of furniture, a dog, a human male, etc. Additionally, or alternatively, the entity identifier 104 may report that a particular entity is an oven with a particular model number; a pet dog with a specific name and breed; an owner or user of intelligent digital assistant system 20, with the owner/user having a particular name and profile; etc. In some examples, the degree of specificity with which the entity identifier 104 identifies/classifies detected entities may depend on one or more of user preferences and sensor limitations.

When applied to people, the entity tracker 100 may in some cases collect information about individuals whom it is unable to identify by name. For example, the entity identifier 104 may record images of a person's face, and associate these images with recorded audio of the person's voice. Should the person subsequently speak to or otherwise address the intelligent digital assistant system 20, the entity tracker 100 will then have at least some information regarding with whom the intelligent digital assistant system is interacting. In some examples, the intelligent digital assistant system 20 could also prompt the person to state their name, so as to more easily identify the person in the future.

In some examples, the intelligent digital assistant system 20 may utilize a person's identity to customize a user interface for the person. In one example, a user may be identified who has limited visual capabilities. In this example and based on this identification, a display of the intelligent digital assistant system 20 (or other device with which the user is interacting) may be modified to display larger text, or to provide a voice-only interface.

The position identifier 106 may be configured to output an entity position (i.e., location) 114 of a detected entity. In other words, the position identifier 106 may predict the current position of a given entity based on collected sensor data, and output such information as entity position 114. As with the entity identity 112, the entity position 114 may have any suitable level of detail, and this level of detail may vary with user preferences and/or sensor limitations. For example, the position identifier 106 may report that a detected entity has a two-dimensional position defined on a plane such as a floor or wall. Additionally, or alternatively, the reported entity position 114 may comprise a three-dimensional position of a detected entity within a real world, three-dimensional environment. In some examples an entity position 114 may comprise a GPS position, a location within a mapping system, etc.

The reported entity position 114 for a detected entity may correspond to the entity's geometric center, a particular part of the entity that is classified as being important (e.g., the head of a human), a series of boundaries defining the borders of the entity in three-dimensional space, etc. The position identifier 106 may further calculate one or more additional parameters describing the position and/or orientation of a detected entity, such as a pitch, roll, and/or yaw parameter. In other words, the reported position of a detected entity may have any number of degrees-of-freedom, and may include any number of coordinates defining the position of the entity in an environment. In some examples, an entity position 114 of a detected entity may be reported even if the entity tracker 100 is unable to identify the entity, and/or determine the current status of the entity.

Status identifier 108 may be configured to output an entity status 116 of a detected entity. In other words, the entity tracker 100 may be configured to predict the current status of a given entity based on received sensor data, and output such information as entity status 116. "Entity status" can refer to virtually any measurable or classifiable property, activity, or behavior of a given entity. For example, when applied to a person, the entity status of the person can indicate a posture of the person (e.g., standing, sitting, laying down), a speed at which the person is walking/running, a current activity of the person (e.g., sleeping, watching TV, working, playing a game, swimming, talking on the phone), a current mood of the person (e.g., by evaluating the person's facial expression or tone of voice), biological/physiological parameters of the person (e.g., the person's heart rate, respiration rate, oxygen saturation, body temperature, neurological activity), whether the person has any current or upcoming calendar events/appointments, etc. "Entity status" can refer to additional/alternative properties or behaviors when applied to other creatures or non-living objects, such as a current temperature of an oven or kitchen sink, whether a device (e.g., television, lamp, microwave) is powered on, whether a door is open, etc.

In some examples, the status identifier 108 may use sensor data to calculate a variety of different biological/physiological parameters of a human. This may be done in a variety of suitable ways. For example, the entity tracker 100 may be configured to interface with an optical heart rate sensor, a pulse oximeter, a sphygmomanometer, electrocardiograph, etc. Additionally or alternatively, the status identifier 108 may be configured to interpret data from one or more cameras and/or other sensors in an environment, and process the data in order to calculate a human's heart rate, respiration rate, oxygen saturation, etc. For example, the status identifier 108 may be configured to utilize Eulerian magnification and/or similar techniques to amplify miniscule movements or changes captured by the cameras, thereby allowing the status identifier to visualize the flow of blood through a human's circulatory system and calculate associated physiological parameters+. Such information can be used, for example, to determine when the person is asleep, working out, in distress, experiencing health problems, etc.

Upon determining one or more of the entity identity 112, entity position 114, and entity status 116, such information may be sent as context information 110 to any of a variety of external modules or devices, where it may be used in a variety of ways. For example, context information 110 may be used by commitment engine 60 to manage commitments and associated messages and notifications. In some examples and as described in more detail below, context information 110 may be used by commitment engine 60 to determine whether a particular message, notification, or commitment should be executed and/or presented to a user. Similarly, context information 110 may be utilized by voice listener 30 when interpreting human speech or activating functions in response to a keyword trigger.

As noted above, in some examples the entity tracker 100 may be implemented in a single computing device. In other examples, one or more functions of the entity tracker 100 may be distributed across multiple computing devices working cooperatively. For example, one or more of the entity identifier 104, person identifier 105, position identifier 106, and status identifier 108 may be implemented on different computing devices, while still collectively comprising an entity tracker configured to perform the functions described herein. As indicated above, any or all of the functions of the entity tracker may be performed by individual sensors 102. Further, in some examples entity tracker 100 may omit one or more of the entity identifier 104, person identifier 105, position identifier 106, and status identifier 108, and/or include one or more additional components not described herein, while still providing context information 110. Additional details regarding components and computing aspects that may be used to implement entity tracker 100 are described in more detail below with respect to FIG. 27.

Each of entity identity 112, entity position 114, and entity status 116 may take any suitable form. For example, each of the entity identity 112, position 114, and status 116 may take the form of a discrete data packet including a series of values and/or labels describing the information gathered by the entity tracker. Each of the entity identity 112, position 114, and status 116 may additionally include a confidence value defining a statistical likelihood that the information is accurate. For example, if the entity identifier 104 receives sensor data that strongly indicates that a particular entity is a human male named "John Smith," then entity identity 112 may include this information along with a corresponding relatively high confidence value, such as 90% confidence. If the sensor data is more ambiguous, then the confidence value included in entity identity 112 correspondingly may be relatively lower, such as 62%. In some examples, separate predictions may be assigned separate confidence values. For example, the entity identity 112 may indicate with 95% confidence that a particular entity is a human male, and indicate with a 70% confidence that the entity is John Smith. As described in more detail below, such confidence values (or probabilities) may be utilized by a cost function in generating cost calculations for providing messages or other notifications to a user and/or performing action(s).

In some implementations, the entity tracker 100 may be configured to combine or fuse data from multiple sensors in order to output more accurate predictions. As an example, a camera may locate a person in a particular room. Based on the camera data, the entity tracker 100 may identify the person with a confidence value of 70%. However, the entity tracker 100 may additionally receive recorded speech from a microphone. Based on the recorded speech alone, the entity tracker 100 may identify the person with a 60% confidence value. By combining the data from the camera with the data from the microphone, the entity tracker 100 may identify the person with a higher confidence value than would be possible using the data from either sensor alone. For example, the entity tracker may determine that the recorded speech received from the microphone corresponds to lip movements of the person visible to the camera when the speech was received, and thereby conclude with relatively high confidence, such as 92%, that the person visible to the camera is the person speaking. In this manner the entity tracker 100 may combine the confidence values of two or more predictions to identify a person with a combined, higher confidence value.

In some examples, data received from various sensors may be weighted differently depending upon a reliability of the sensor data. This can be especially relevant in situations where multiple sensors are outputting seemingly inconsistent data. In some examples, the reliability of a sensor's data may be based at least in part on the type of data generated by the sensor. For example, in some implementations a reliability of video data may be weighted higher than a reliability of audio data, as the presence of an entity on camera may be a better indicator of its identity, position, and/or status than recorded sounds that are presumed to originate from the entity. It will be appreciated that a reliability of sensor data is a different factor than a confidence value associated with a predicted accuracy of an instance of data. For example, several instances of video data may have different confidence values based on different contextual factors present at each instance. Each of these instances of video data, however, may be associated with a single reliability value for video data in general.

In one example, data from a camera may suggest that a particular person is in a kitchen with a 70% confidence value, such as via face recognition analysis. Data from a microphone may suggest with a 75% confidence value that the same person is in a nearby hallway, such as via voice recognition analysis. Even though the instance of microphone data carries a higher confidence value, the entity tracker 100 may output a prediction that the person is in the kitchen based on a higher reliability of the camera data as compared to a lower reliability of the microphone data. In this manner and in some examples, different reliability values for different sensor data may be used along with confidence values to reconcile conflicting sensor data and determine an identity, position, and/or status of an entity.

Additionally or alternatively, more weight may be given to sensors that have higher precision, more processing power or otherwise greater capabilities. For example, a professional-grade video camera may have a significantly improved lens, image sensor, and digital image processing capabilities as compared to a basic webcam found in a laptop. Accordingly, a higher weight/reliability value may be given to video data received from the professional-grade camera as compared to the webcam, as such data is likely to be more accurate.

Figure 8:
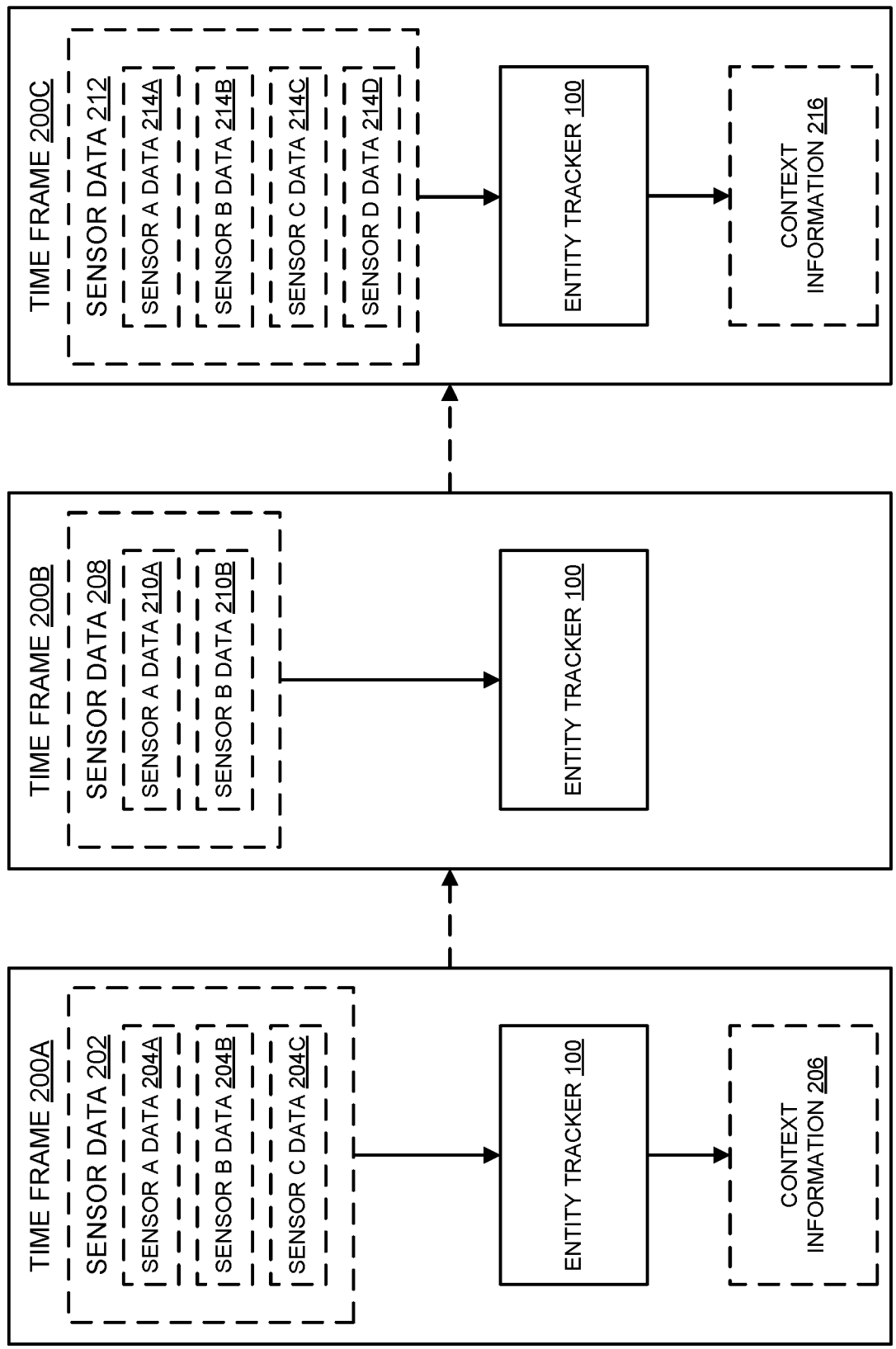
FIG. 8 schematically shows an entity tracker receiving and interpreting sensor data over multiple time frames according to examples of the present disclosure.

With reference now to FIG. 8, in some examples, individual sensors used with the entity tracker 100 may output data with a different frequency than other sensors used with the entity tracker. Similarly, sensors used with the entity tracker 100 may output data with a different frequency than the frequency with which the entity tracker evaluates the data and outputs context information. In the example of FIG. 8, entity tracker 100 may receive and interpret sensor data over multiple time frames 200A, 200B, and 200C. A single time frame may represent any suitable length of time, such as $1/30^{th}$ sec., $1/60^{th}$ sec., etc.

In this example, during time frame 200A entity tracker 100 receives a set of sensor data 202 including sensor A data 204A, sensor B data 204B, and sensor C data 204C. Such sensor data is interpreted by entity tracker 100 and transformed into context information 206, which may be used to determine an identity, position, and/or status of one or more detected entities as described above. During time frame 200B, entity tracker 100 receives sensor data 208, including sensor A data 210A and sensor B data 210B. Entity tracker 100 does not receive data from sensor C during time frame 200B, as sensor C outputs data at a different frequency than sensors A and B. Similarly, entity tracker 100 does not output context information during time frame 200B, as the entity tracker outputs context information at a different frequency than sensors A and B.

During time frame 200C, entity tracker 100 receives sensor data 212, including sensor A data 214A, sensor B data 214B, sensor C data 214C, and sensor D data 214D. Entity tracker 100 also outputs context information 216 during time frame 200C, which may be based on any or all of the sensor data received by the entity tracker since context information was last output in time frame 200A. In other words, context information 216 may be based at least in part on sensor data 208 as well as sensor data 212. In some examples, context information 216 may be based at least in part on sensor data 202 and sensor data 208, as well as sensor data 212.

As shown in FIG. 8, after the entity tracker 100 receives data from a particular sensor, multiple time frames may pass before the entity tracker receives more data from the same sensor. During these multiple time frames, entity tracker 100 may output context information. Similarly, the usefulness of data received from a particular sensor may vary from time frame to time frame. For example, at a first time frame the entity tracker 100 may receive audio data of a particular person speaking via a microphone, and accordingly identify an entity position 114 of the person with a relatively high confidence value. In subsequent time frames, the person may remain at the identified position, but also may have stopped speaking since the first time frame. In this case, the absence of useful data from the microphone may not be a reliable indicator of the absence of the person. Similar issues can arise with other types of sensors. For example, a camera may lose track of a person if he covers his face, or is occluded by an obstacle, such as another person or a moving object. In this case, though current camera data may not suggest the presence of the person, prior instances of camera data may suggest that the person is still located at the previously identified position. In general, while sensor data may reliably indicate the presence of an entity, such data may be less reliable in suggesting the absence of an entity.

Accordingly, the entity tracker 100 may utilize one or more confidence decay functions, which in different examples may be defined by the entity tracker and/or by the sensors themselves. A confidence decay function may be applied to sensor data to reduce the entity tracker's confidence in the data from a particular sensor as time passes since that sensor last positively detected an entity. As an example, after a sensor detects an entity at a particular location, the entity tracker 100 may report context information 110 indicating that the entity is at the location with relatively high confidence. If after one or more time frames the sensor no longer detects the entity at the location, and unless it subsequently gathers contradictory evidence, the entity tracker 100 still may report that the entity is at the location, though with a somewhat lower confidence. As time continues to pass since the sensor last detected the entity at the location, it becomes progressively less likely that the entity is still at the location. Accordingly, the entity tracker 100 may utilize the confidence decay function to progressively decrease the confidence value of its reported context information 110, eventually reaching 0% confidence if no additional sensors detect the entity.

In some cases, different confidence decay functions may be utilized with different sensors and sensor types. A selection of a particular decay function may depend at least in part on particular properties of a sensor. For example, confidence values associated with data from a video camera may decay more rapidly than confidence values associated with data from a microphone, as absence of an entity in a video frame is a more reliable indicator of the entity's absence than silence recorded by a microphone.

Figure 9:
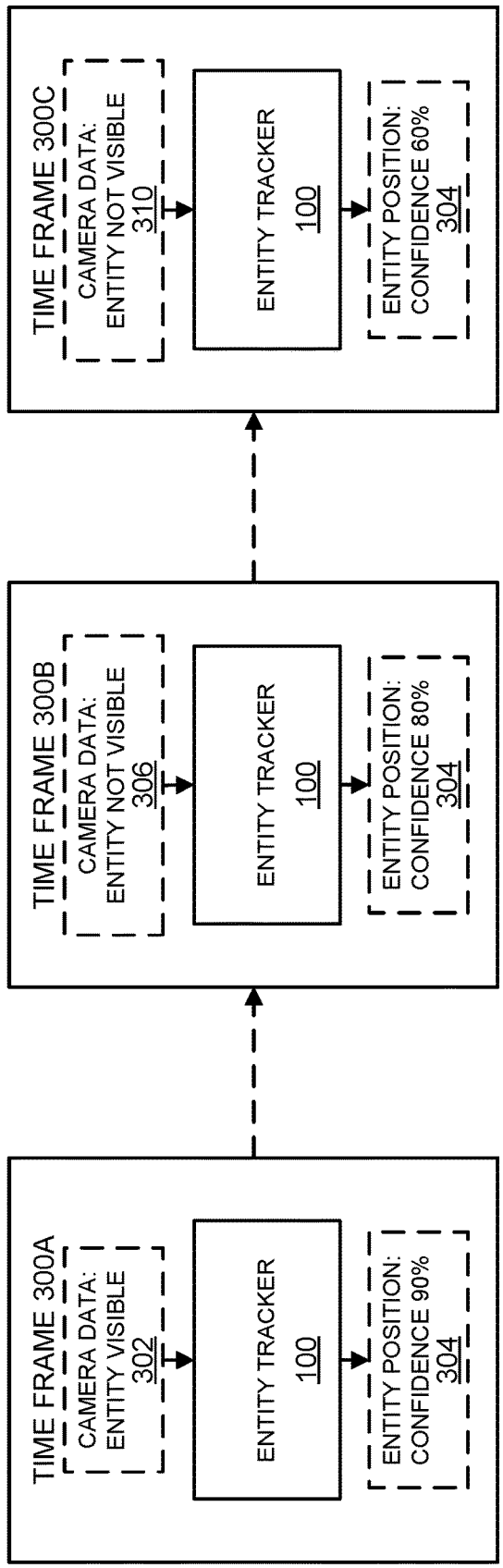
FIG. 9 schematically shows an example of sensor confidence decay over time via an entity tracker according to an example of the present disclosure.

One example of sensor confidence decay is schematically illustrated in FIG. 9, which shows entity tracker 100 receiving sensor data during three different time frames 300A, 300B, and 300C. During time frame 300A, entity tracker 100 receives camera data 302 in which an entity is visible in the frame. Based on this data, the entity tracker 100 reports the entity position 304 with a 90% confidence value. In time frame 300B, entity tracker 100 receives camera data 306 in which the entity is no longer visible in the frame. However, it is possible that the entity has not moved, and has merely become occluded, or otherwise undetectable to the camera. Accordingly, entity tracker 100 reports the same entity position 304, but with a lower confidence value of 80%.

Finally, in time frame 300C entity tracker 100 receives camera data 310 indicating that the entity is still not visible in the frame. As time has passed, it has grown less likely that the entity is still in the same position. Accordingly, the entity tracker 100 reports the same entity position 304 with a still lower confidence value of 60%.

In some examples, variable reliability of sensor data may be at least partially addressed by making use of data filtering techniques. In some examples, a Kalman filter may be utilized to filter sensor data. A Kalman filter is a mathematical function that may combine multiple uncertain measurements and output a prediction with more confidence than would be possible using any individual measurement. Each measurement input to the Kalman filter is given a weight based on the measurement's perceived reliability. Kalman filters operate in a two-step process, including a prediction step and an update step. During the prediction step, the filter outputs a prediction based on recent weighted measurements. During the update step, the filter compares its prediction to an actual observed value or state, and dynamically adjusts the weighting applied to each measurement so as to output more accurate predictions.

In some examples, entity tracker 100 may comprise a Kalman filter that combines data from a variety of sensors to compensate for lower sensor reliability, such as when sensor confidence values have decayed over time since the last positive detection. In some examples, entity tracker 100 may apply a Kalman filter to sensor data when one or more sensor confidence values are below a predetermined threshold. In an example scenario, image data from a camera may be analyzed using face detection techniques to reliably detect a person in a particular room. In response, the entity tracker 100 may report with high confidence that the person is located in the room.

In subsequent time frames, the camera may no longer be able to capture and/or positively recognize the person's face in the room. For example, the person's face may become occluded, or the camera may transmit data with a much lower frequency than the entity tracker 100 outputs context information 110. If the entity tracker 100 relied exclusively on data from the camera, then the confidence value of its reported position of the person would gradually decrease until the next positive detection. However and in some examples, data from the camera may be supplemented with data from other sensors. For example, during the subsequent time frames a microphone may report that it hears the person's voice in the room, or another sensor may report that it can detect the presence of the person's mobile device in the room. In such cases, this data may be assigned weights by the Kalman filter, and may be used to predict the person's current location with more confidence than would be possible if only the camera data were used.

In some cases, detection of people and/or other entities in an environment can become more complicated when sensor data is contaminated by background information. Such background information may compromise the confidence with which the entity tracker 100 reports entity identity 112, position 114, and/or status 116. For example, the intelligent digital assistant system 20 may need to determine the identity of a person who is speaking in order to appropriately respond to a query or command. Such a determination can be difficult when multiple people are speaking at the same time, a television is playing, loud machinery is operating, etc.

Accordingly, the entity tracker 100 may use a variety of audio processing techniques to more confidently identify a particular active participant who is engaged in a conversation with other people and/or with the intelligent digital assistant system 20. As an example, the entity tracker 100 may implement a voice activity detection (VAD) engine that may distinguish human voices from environmental noise, and identify the presence or absence of human speech.

General-purpose VAD engines may be used for the purpose of classifying a particular segment of audio as including either speech or non-speech, with a corresponding confidence value. An entity tracker 100 also may utilize a speaker recognition engine to match a particular audio segment with a particular person. As more speech is received, the speaker recognition engine may be progressively tailored to classify the audio as including speech from a particular conversation participant, or not including speech from the particular conversation participant. In this manner, the entity tracker 100 may recognize speech from one or more particular persons/conversation participants.

Training of a speaker recognition engine may occur any time the entity tracker 100 has confidently identified a particular person and recorded audio that can be confidently attributed to that person. For example, using camera data, the entity tracker 100 may identify a particular person and determine that the person's lips are moving. The entity tracker 100 may simultaneously receive audio from a microphone that can be safely assumed to include speech from the identified person. Accordingly, the received audio can be used to retrain the speaker recognition engine to more specifically recognize the identified person's voice.

In some cases, such retraining may occur only when the person has been identified with a high confidence value (e.g., via accurate facial recognition or any other method), such as a confidence value exceeding a predetermined threshold, and when the entity tracker 100 has received an audio recording of the person's voice having high volume/amplitude and a high signal-to-noise ratio (S/N). Using this technique, the entity tracker 100 may accumulate a variety of person-specific voice models, allowing the entity tracker to more consistently identify speech from particular people and ignore background noise.

Figure 10:
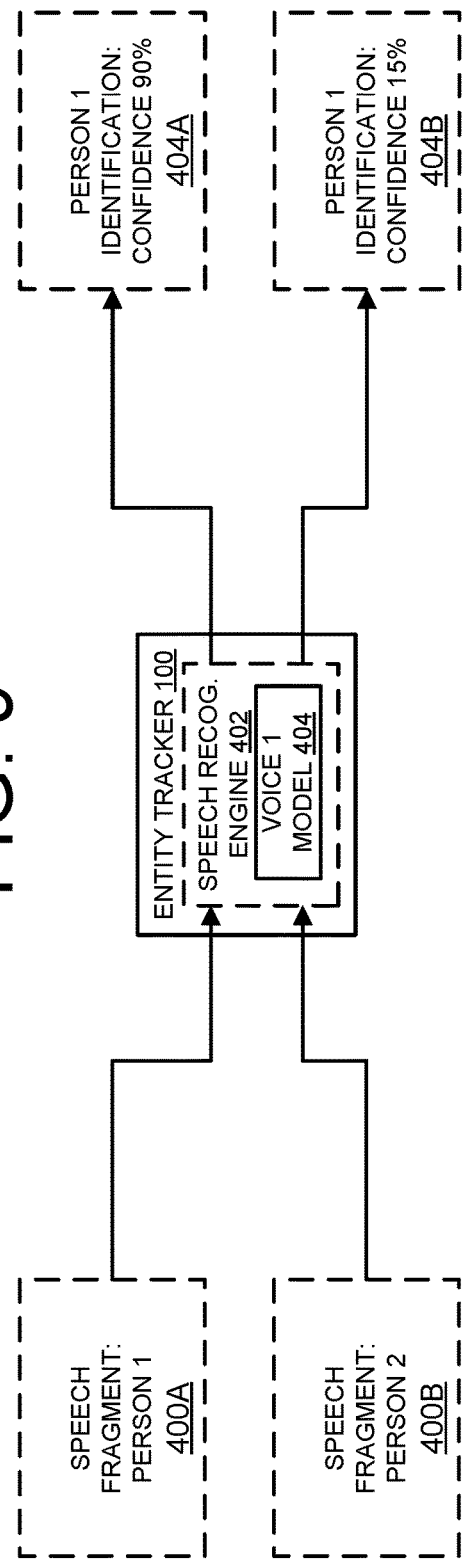
FIG. 10 schematically shows an example of using a trained voice recognition engine to recognize a person's speech according to examples of the present disclosure.

With reference now to FIG. 10, an example of using a trained speech recognition engine to recognize speech from a particular person is schematically illustrated. In this example, entity tracker 100 receives two speech fragments 400A and 400B. Speech fragment 400A includes recorded speech of a person 1, and speech fragment 400B includes recorded speech of a person 2. Entity tracker 100 includes a speech recognition engine 402 that has been specifically trained to recognize speech from person 1 using a voice 1 model 404, as described above. Voice 1 model 404 may be applied to each of speech fragment 400A and speech fragment 400B as they are received by the entity tracker 100.

Upon processing the speech fragments, the entity tracker 100 outputs a prediction of the likelihood that each speech fragment corresponds to person 1. As shown, for speech fragment 400A, the entity tracker outputs a person 1 identification 404A with a 90% confidence value, indicating that the speech fragment likely includes speech from person 1. For speech fragment 400B, the entity tracker outputs a person 1 identification 404B with a 15% confidence value, indicating that speech fragment 400B likely does not include speech from person 1.

In some examples, an entity tracker 100 may be configured to identify background noise present in an environment, and use audio processing techniques to subtract such background noise from received audio data. For example, a particular device in a person's home may be playing background audio, such as music or television/movie dialogue. Various microphone-equipped devices in the person's home may record such audio. Where such microphone-equipped devices include the intelligent digital assistant system 20 and/or provide audio data to the entity tracker 100, such background audio may compromise the ability of the system to identify, interpret and/or respond to human questions or commands.

Accordingly and in some examples, the device playing the background audio and/or another microphone-equipped device recording the background audio may send the captured audio signal to the entity tracker 100. In this manner, the entity tracker 100 may subtract the background audio from the audio signal received from the microphone-equipped devices. In some examples, the subtraction of the background audio signal from the recorded audio data may be performed by the device(s) that capture the audio data, or by associated audio-processing components, prior to sending the audio data to the entity tracker 100.

Additionally or alternatively, devices and/or the entity tracker 100 may be trained to recognize particular sources of background noise (e.g., from an air vent or refrigerator), and automatically ignore waveforms corresponding to such noise in recorded audio. In some examples, an entity tracker 100 may include one or more audio-recognition models trained specifically to recognize background noise. For example, audio from various noise databases may be run through unsupervised learning algorithms in order to more consistently recognize such noise. By allowing the entity tracker 100 to recognize irrelevant background noise, the ability of the entity tracker to recognize relevant human speech and other sounds may be improved.

Figure 11:
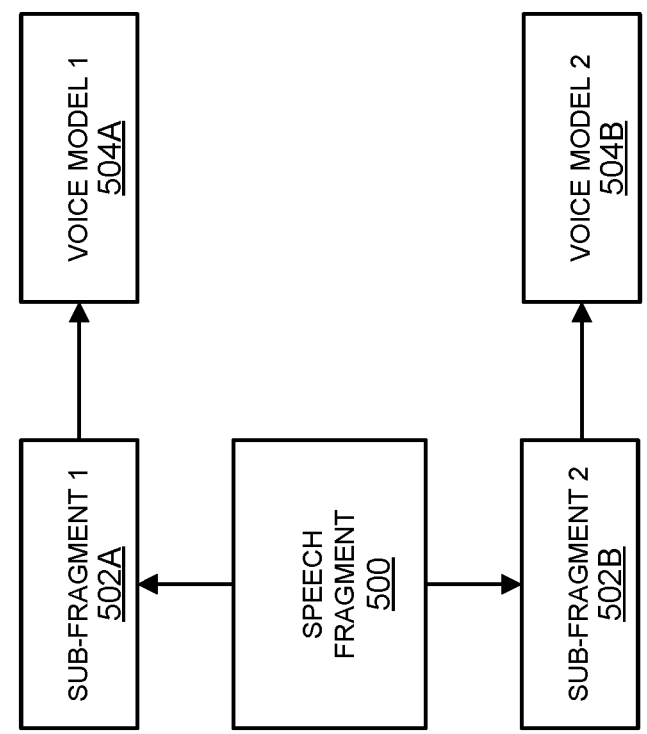
FIG. 11 schematically shows an example of using sub-fragments of audio data to train voice models according to examples of the present disclosure.

With reference now to FIG. 11, in some cases the entity tracker 100 may determine that a change has occurred in the active participant (i.e., the person currently speaking) in a conversation between two or more people. The entity tracker 100 also may determine at what point in time such a change occurred. This may be done in a variety of ways. In one example, a segment of recorded audio containing a speech fragment may be time-divided into two or more subframes, with each subframe containing a different sub-fragment of the recorded speech fragment. In the example of FIG. 11, speech fragment 500 may be time-divided into two or more sub-fragments, such as sub-fragment 1 502A and sub-fragment 2 502B. Each sub-fragment of speech may be used to train a separate voice model, such that the trained voice model may be used to specifically recognize speech from whichever person was speaking during that subframe. In FIG. 11, sub-fragment 502A is used to train voice model 1 504A, while sub-fragment 502B is used to train voice model 2 504B.

Figure 12:
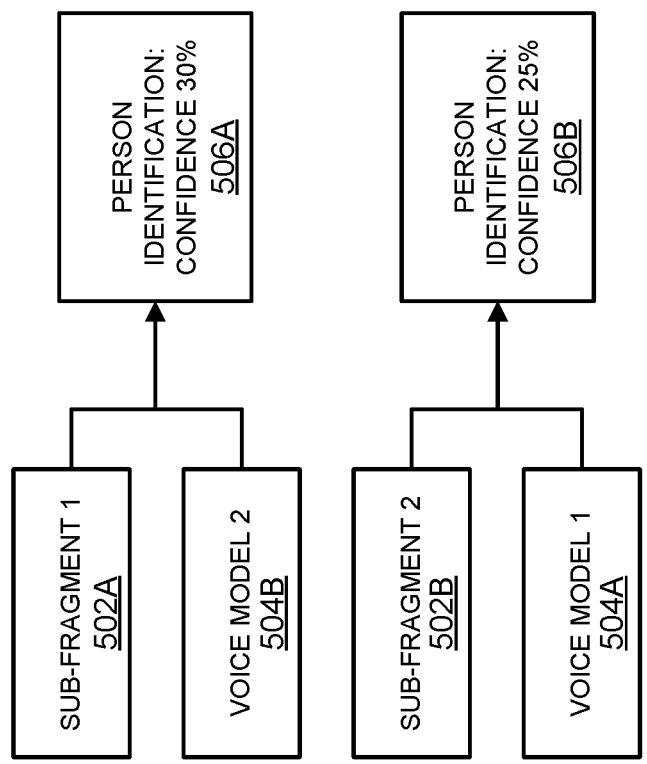
FIG. 12 schematically shows an example of cross-evaluating sub-fragments of audio data to determine whether the active speaker has changed according to examples of the present disclosure.

Once the sub-fragments have been used to train voice models, the sub-fragments may be cross-evaluated with different voice models. This is schematically shown in FIG. 12, in which voice model 2 504B, which was trained using sub-fragment 2 502B, is applied to sub-fragment 1 502A. Similarly, voice model 1 504A, which was trained using sub-fragment 1 502A, is applied to sub-fragment 2 502B.

During cross-evaluation, a prediction with a high confidence value will be generated if the person speaking during the tested sub-fragment is the same as the person speaking during the sub-fragment with which the voice model was trained. Accordingly, if both voice models result in predictions of the speaker identity with relatively high confidence values, then it is likely that the same person was speaking during both sub-fragments, and the active participant in the conversation did not change during the speech fragment. If both voice models result in predictions of the speaker identity with relatively low confidence, then it is likely that the active conversation participant changed at some point during the speech fragment. This possibility is illustrated in FIG. 12, in which voice model 2 504B outputs person identification 506A with a confidence value of 30%, and voice model 1 504A outputs person identification 506B with a confidence value of 25%. As both voice models have relatively low confidence in their predictions, it is likely that different people were speaking in each of sub-fragment 502A and sub-fragment 502B. It follows that it is likely that the active conversation participant changed at some point between sub-fragment 1 502A and sub-fragment 2 502B.

In some examples, and depending on the sensors and processing methods used by the entity tracker 100, tracking and identification of entities in an environment can be time-consuming and resource-intensive. Accordingly, the entity tracker 100 may use a variety of techniques to selectively choose when resource-intensive processing should be utilized. In this manner, the efficiency of the entity tracker 100 may be improved without compromising its corresponding functionality.

As an example, a variety of image processing techniques may be used to account for variable lighting conditions in an environment. In some examples, and depending on the brightness/darkness levels in a room, an entity tracker 100 can perform contrast adjustment and/or other image processing techniques in order to more clearly track and identify entities in the room. Such techniques, however, may require significant processing and computer resources. Accordingly and to conserve such resources, additional context information 110 may be evaluated to determine whether to utilize such techniques.

For example, where a room is dark and context information 110 with high confidence values indicates the room is empty, the entity tracker 100 may forego computationally-intensive image processing techniques in favor of conserving resources. In another example, where another sensor in the room detects that a person is likely present (e.g., a microphone records the person's voice), the entity tracker 100 may authorize the use of computationally-intensive image processing in an attempt to obtain an image that can be used to identify the person's face. In another example, an entity tracker 100 may reduce the sampling frequency of any sensors monitoring an environment in which no entities of interest are currently present. Thereafter, the entity tracker 100 may increase the sampling frequency of one or more sensors as needed, such as when the presence of an entity of interest is indicated with a confidence value exceeding a predetermined threshold.

Another process which can require significant computer resources is facial recognition using high-resolution images. In some examples, upon establishing a positive identification of a person using facial-recognition techniques, the entity tracker 100 may switch to less resource-intensive identification methods in order to continue tracking the person. As an example, upon detecting that a new person has entered a room, the entity tracker 100 may capture a high-resolution image of the person's face. The entity tracker 100 may utilize this image to perform relatively resource-intensive facial recognition in order to definitively identify the person.

After initial identification of the person, the entity tracker 100 may use less resource-intensive techniques in order to continue tracking the person while conserving computing resources. For example, the entity tracker 100 may use lower-resolution cameras to track the person based on the general shape of their body, their gait (e.g., by evaluating angles formed between different joints as the person walks), their clothing (e.g., tracking patches of color known to correspond to the person's clothing), etc. In some examples, and to periodically confirm its initial identification of the person is still accurate, the entity tracker 100 may perform facial recognition intermittently after the initial identification. In general and depending on the particular context, the entity tracker 100 may use any of a variety of identification techniques in order to intelligently manage both conservation of computing resources and identification and tracking of entities.

As noted above, the commitment engine 60 stores commitments received from the intent handler 50. Also as described above, the commitment engine 60 may utilize one or more cost functions to determine one or more costs associated with executing or not executing a commitment and, in some examples, with outputting or not outputting a message to the user. As described in more detail below, in some examples one or more messages may be added to a message queue.

Figure 13:
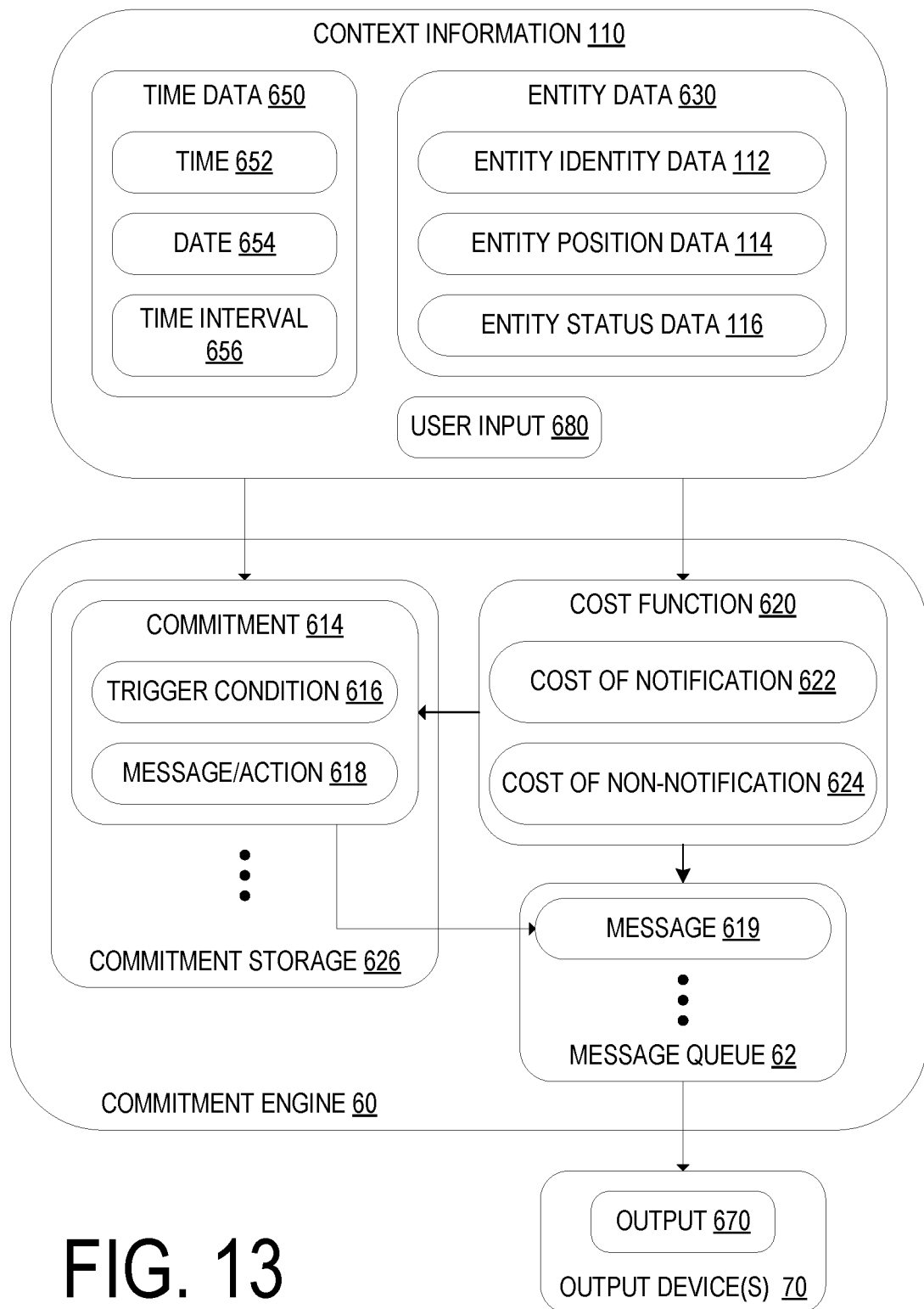
FIG. 13 shows a schematic illustration of a cost function according to examples of the present disclosure.

With reference now to FIG. 13, a schematic illustration of an example cost function 620 usable with commitment engine 60 is provided. The commitment engine 60 includes commitment storage 626 configured to store one or more commitments 614. The commitment 614 shown in FIG. 13 includes a trigger condition 616 and a message/action 618. In some examples, a commitment may comprise a set of 0 or more triggers and a set of 1 or more messages/actions (such as convey a message to a user, turn on the lights, play music, etc.). In some examples, the message/action 618 may comprise conveying a message 619 stored in a message queue 62 as output 670 via one or more output devices 70. In some examples, the message/action 618 may comprise executing one or more additional instructions that may include interfacing with one or more other devices or programs.

The commitment engine 60 is configured to receive context information 110 via entity tracker 100 and/or directly from one or more sensors 22. In various examples, the context information 110 may or may not satisfy a trigger condition, such as trigger condition 616. The context information 110 may include entity data 630 from the entity tracker 100. The context information 110 may further include time data 650 and/or a user input 680. The entity data 630, time data 650, and user input 680 are described in greater detail below.

When the commitment engine 60 receives context information 110 that satisfies the trigger condition 616 of the commitment 614, the commitment engine 60 may apply a cost function 620 to the message/action 618. Where the message/action 618 comprises a message, the cost function 620 is configured to determine whether to output the message associated with the commitment 614 to one or more users. Similarly, where the message/action 618 comprises an action, the cost function 620 is configured to determine whether to perform the action based at least in part on the context information 110. When the cost function 620 determines that the commitment 614 is of high enough importance, the commitment engine 60 may output the message and/or perform the action of message/action 618 as an output 670. The output 670 may be conveyed to one or more output devices 70. For example, the output 670 may comprise a verbal message that is broadcast by a speaker of a user's smartphone and/or one or more other speakers in the user's environment, such as a standalone speaker device, a television speaker, etc. In some examples, the output 670 may comprise controlling one or more other devices, such as turning on lights, playing music via a media program, etc.

The cost function 620 may determine whether to output a message 619 by calculating a cost of notification 622 and a cost of non-notification 624. If the cost of non-notification 624 is determined to be higher than the cost of notification 622, the commitment engine 60 may output the message 619. In some examples, the cost of notification 622 and the cost of non-notification 624 may be determined at least in part using one or more machine learning algorithms.

In some examples, the cost function 620 may determine the cost of notification 622 and the cost of non-notification 624 based at least in part on entity data 630 received from the entity tracker 100 and included in the context information 110. As explained above, the entity data 630 may include entity identity data 112, entity position data 114, and entity status data 116. The entity identity data 112, entity position data 114, and entity status data 116 may each include at least one list of users, locations, and activities respectively. Each user, location, and activity included in the entity identity data 112, entity position data 114, and entity status data 116 may have an associated estimate of a probability that that user, location, or activity was correctly identified. Such probability estimates may be utilized by the cost function 620 in determining corresponding costs of notification 622 and costs of non-notification 624. In some examples, the context information 110 may include entity identity data 112, entity position data 114, and entity status data 116 for one or more users or other entities detected simultaneously.

The commitment engine 60 also may be configured to receive time data 650. The time data 650 may include a time 652 and/or date 654. The time data 650 also may include at least one time interval 656 elapsed since a computing device performed some task. For example, the time data 650 may include at least one time interval 656 elapsed since a computing device produced a particular output or received a particular input. For example, a user may set a time interval 656 on an oven timer while baking bread, and the commitment engine 60 may receive context information 110 that satisfies the trigger condition 616 when the time interval 656 elapses and the oven timer buzzes. In response, the cost function 620 may be applied to a related commitment 614 to determine whether to output a message 619 that the bread should be removed from the oven, and/or perform an action to turn off the oven.

As another example, the time data 650 may include data indicating when a computing device most recently produced an output 670 notifying a user that the user should do laundry. The message queue 62 may store a related message 619 reminding the user to do his laundry. As the amount of time increases since the message was last given, as indicated by the time data 650, the cost function 620 may gradually increase the cost of non-notification 624. When the laundry notice is given, the cost function 620 may decrease the cost of non-notification 624 of the message 619. In some examples, the cost function 620 may determine the cost of notification 622 and the cost of non-notification 624 based at least in part on the time data 650.

The cost function 620 may determine the cost of notification 622 and the cost of non-notification 624 based at least in part on one or more user inputs 680. For example, a user may provide a user input 680 that increases the cost of non-notification 624 for a notification the user considers particularly important. The user may, in one example, provide a user input 680 to increase the cost of non-notification 624 for a job interview compared to a default cost of non-notification 624 for a lunch meeting with a friend.

The commitment engine 60 may determine an output type for the output 670. The determination of the output type may be made based on the entity data 630 and/or time data 650. For example, the commitment engine 60 may determine, based on user location data, that a user is not in a location at which the user would be able to view a display screen. The commitment engine 60 may therefore generate an output 670 that is conveyed to a speaker instead of the screen. In addition, some output types may have costs of notification 622 different from those of other output types. For example, a visual display may have a lower cost of notification 622 than a sound output, since a visual output may be less likely to interrupt a conversation.

In one example, the commitment engine 60 may receive context information 110 that satisfies the trigger condition 616 for a commitment 614 with the message "John has a meeting in 15 minutes." A cost function 620 then may be applied to the commitment 614. The cost function 620 may use entity data 630 to determine a cost of notification 622 and a cost of non-notification 624. The cost of notification 622 and the cost of non-notification 624 may be determined based at least in part on factors such as how important the message is to John, how receptive John is to receiving the message, and whether John is in a location that may be related to the message. For example, the entity data 630 may include entity identity data 112 and entity position data 114 that indicate that John is not currently in a location in which he could perceive an output 670 from the output device 672. As a result, the cost of non-notification 624 may be very small. In another example, based on entity data 630, the commitment engine 60 may determine that the cost of notification 622 is higher when John is making a telephone call than when John is reading a newspaper. In another example, where the message content includes medical information about John's newborn baby, the cost of non-notification 624 may be determined to be high.

In another example, the commitment engine 60 may receive context information 110 indicating that a baby is in a location near a user's swimming pool. This context information 110 may satisfy a trigger condition 616 for a commitment 614 corresponding to the situation in which a baby is near the user's pool. The commitment 614 may include a message/action 618 to broadcast an urgent message to a user that a baby is near the pool. A cost function 620 may be applied to a commitment 614. Based at least in part on the trigger condition 616 of the commitment 614 relating to a potentially serious safety situation involving a baby, the cost function 620 may determine that the commitment 614 has a very high cost of non-notification 624.

Continuing with this example, based on entity data 630 including user activity data, the commitment engine 60 may determine that the user is currently making a telephone call. The commitment engine 60 also may access profile data of the user indicating that the user strongly prefers to avoid interruptions when he is talking on the phone. As a result, the commitment engine 60 may determine that the cost of notification 622 is also high. In this example, given that the message relates to a safety situation involving a baby, the commitment engine 60 may determine that the cost of non-notification 624 is higher than the cost of notification 622. Accordingly, the commitment engine 60 conveys the urgent message 619 as an output 670 to be output by the output device 672 to the user.

In another example, commitment engine 60 may receive context information 110 that triggers the trigger condition 616 for a commitment 614 with the message "John has a meeting in 15 minutes." Using entity data 630, the commitment engine also may determine that John is currently making a telephone call. The commitment engine 60 may determine that since outputting a message notifying John of the commitment 614 on the output device 672 would interrupt John's telephone call, the cost of notification 622 is greater than the cost of non-notification 624. Thus, the commitment engine 60 may not convey the message to the output device 672 as output 670.

As the time of John's meeting approaches, the commitment engine 60 may increase the cost of non-notification 624 based on time data 650. For example, the commitment engine 60 may determine that John is five minutes away from the location of the meeting. When the time data 650 indicates that the meeting will begin in six minutes, the cost of non-notification 624 may be high enough that the commitment engine 60 conveys the message 619 to the output device 672 even though John is still making the telephone call.

Figure 14:
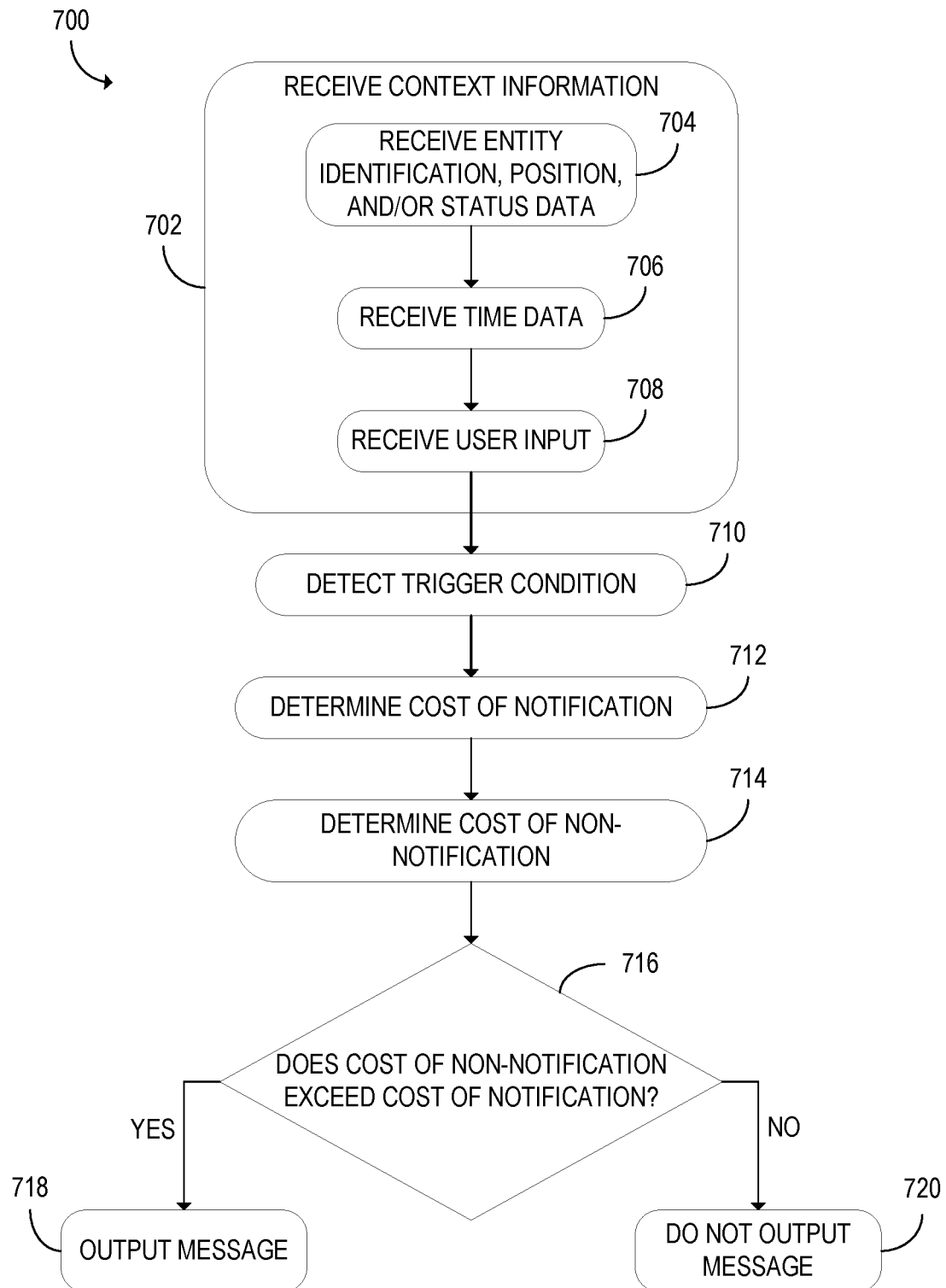
FIG. 14 shows a flowchart of a method for determining a cost of notification and a cost of non-notification according to examples of the present disclosure.

A flowchart of a method 700 for determining a cost of notification and a cost of non-notification of a message is shown in FIG. 14. The following description of method 700 is provided with reference to the software and hardware components described herein. It will be appreciated that method 700 also may be performed in other contexts using other suitable hardware and software components.

At 702 the method 700 may include receiving context information. Receiving the context information may include receiving entity data, time data, and/or a user input. At 704 the method 700 may include receiving entity data including entity identity, position, and/or status data. At 706 the method 700 may include receiving time data. The time data may include a time and/or date. The time data may further include at least one time interval. At 708 the method 700 may include receiving a user input.

At 710 the method 700 may include detecting that a trigger condition has occurred, based at least in part on the context information. The trigger condition may be associated with a commitment.

At 712 the method 700 may include determining a cost of notification that is associated with outputting the message on an output device. At 714 the method 700 may include determining a cost of non-notification that is associated with not outputting the message. In some examples, determining the cost of notification and the cost of non-notification may be based at least in part on the entity data, time data, and/or user input. In some examples, the cost of notification and cost of non-notification may be determined at least in part using a machine learning algorithm.

At 716 the method 700 may include comparing the cost of notification to the cost of non-notification. At 718 the method 700 may include, if the cost of non-notification exceeds the cost of notification, conveying the message to be output on the output device. At 720 the method 700 may include, if the cost of non-notification does not exceed the cost of notification, refraining from conveying the message to the output device.

It will be appreciated that method 700 is provided by way of example and is not meant to be limiting. Therefore, it is to be understood that method 700 may include additional and/or alternative steps relative to those illustrated in FIG. 14. Further, it is to be understood that method 700 may be performed in any suitable order. Further still, it is to be understood that one or more steps may be omitted from method 700 without departing from the scope of this disclosure.

In some examples, one or more cost functions may be used to determine and/or adjust a sampling rate of one or more sensors. In some use case scenarios, sampling and analyzing an environment with sensors may be a computationally intensive task. As explained above, a cost function may determine a cost of executing and/or not executing an action (such as communicating a message). Using such determinations, the system may increase or decrease the sample rate of one or more sensors that provide data related to the action. For example, where the action comprises notifying a user via outputting a message on an output device, a sensor rate may be increased or decreased based at least in part on the magnitude of the cost associated with refraining from outputting the message (e.g., non-notification).

In some examples, one or more cost functions may be used to customize a type and/or manner of delivery of a notification. In one example, a cost function may determine that a cost of non-notification of a message may be very high. For example, a user may establish a rule with the system that any messages containing the word "baby" are assigned a highest, critical importance status. Accordingly, where a message includes the word "baby", a cost function may determine that the cost of non-notification is very high, and correspondingly may broadcast the message at a high volume via all available speakers in a user's home.

Figure 15:
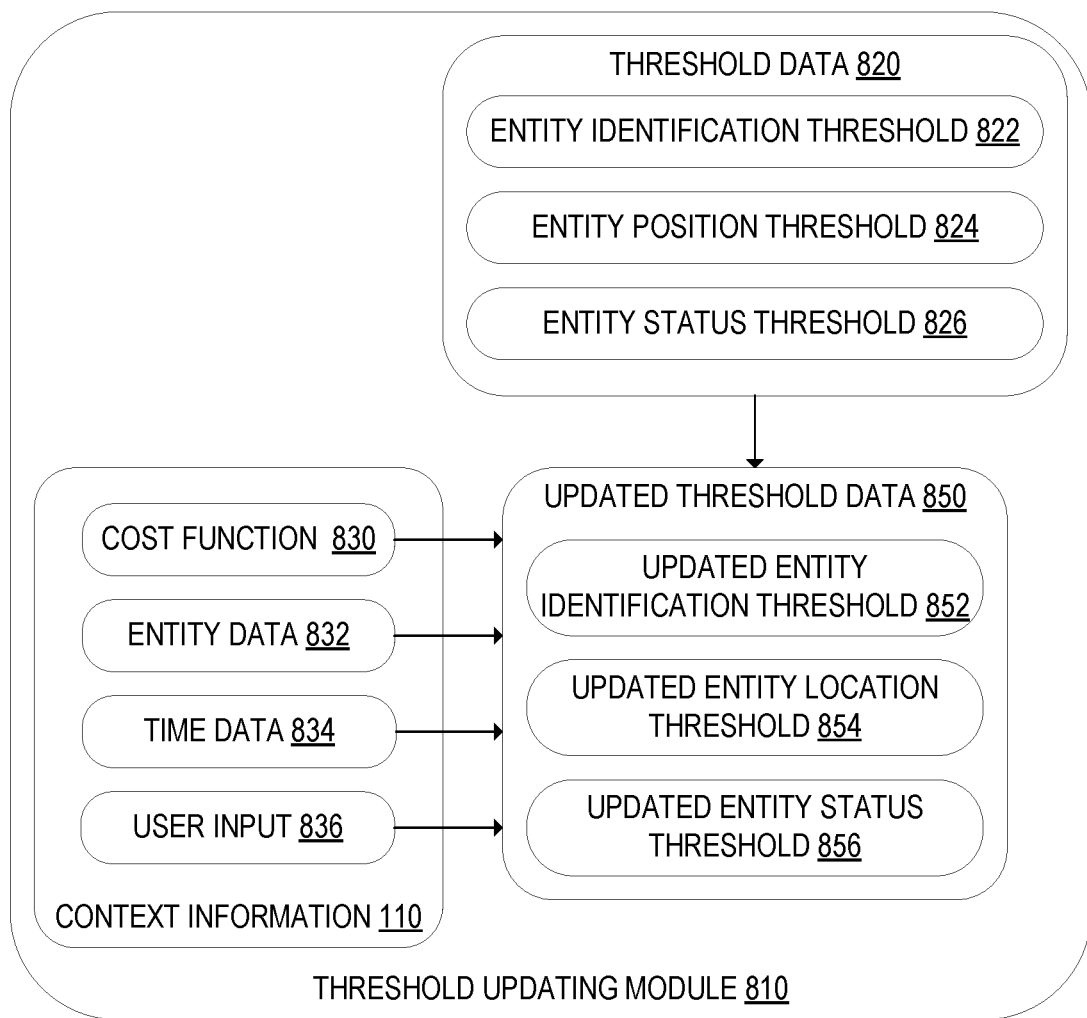
FIG. 15 shows a schematic representation of a threshold updating module according to examples of the present disclosure.

With reference now to FIG. 15, a schematic representation of a threshold updating module 810 according to examples of the present disclosure is provided. In different examples, threshold updating module 810 may be a standalone module in intelligent digital assistant system 20, or may be a component of the entity tracker 100, parser 40, or commitment engine 60. In some examples, the threshold updating module 810 may be configured to modify threshold data 820 that may be used to parse entity data 832. The threshold data 820 may include an entity identification threshold 822, an entity position/location threshold 824, and an entity status threshold 826. Each of these thresholds may be defined as a probability. When an entity identity, location, or status is determined to have a detection probability that exceeds the threshold probability for that entity identity, location, or status, a detection of that entity identity, location, or status may be indicated and/or recorded.

The threshold data 820 may be updated by the threshold updating module 810 to produce updated threshold data 850. The updated threshold data 850 may include an updated entity identification threshold 852, an updated entity location threshold 854, and an updated entity status threshold 856. The threshold updating module 810 may update the threshold data 820 based on a cost function 830, entity data 832, time data 834, and/or user input 836. In some examples, the cost function 830, entity data 832, and time data 834 may be the cost function 620, entity data 630, and time data 650 of FIG. 13.

In some examples, the threshold updating module 810 may update the threshold data 820 based on a modification of the cost function 830. As described above, the cost function 830 may be configured to determine a cost of notification and a cost of non-notification for messages that may be conveyed for output. In some examples, the modification to the cost function 830 may be made in response to a user input 836. For example, a sleep-deprived user may enter an input that increases the cost of notification when that user is determined to be sleeping. As a result, the threshold updating module 810 may decrease a user status threshold 826 for determining that the user is sleeping. In some examples, the user may enter an input 836 that directly updates the threshold data 820.

The threshold updating module 810 may also update the threshold data 820 based on entity data 832. As noted above, the entity data 832 may include entity identification data, entity location data, and/or entity status or activity data. In one example, threshold data 820 may include an entity identification threshold 822 and an entity location threshold 824 for detecting that both a child and an adult are simultaneously in proximity to a hot stove. The threshold updating module 810 may receive entity data 832 indicating that a child is alone in proximity to the hot stove. In response, the threshold updating module 810 may revise the corresponding entity identification threshold 822 and entity location threshold 824 to be lower.

In some examples, the threshold updating module 810 may also update the threshold data 820 based on time data 834. The time data may include a time, date, and/or at least one time interval that has elapsed since a particular input has been outputted, or since a particular input has been received. For example, the entity status threshold 826 for sleeping may be lowered when the time data 834 indicates that it is nighttime.

Figure 16:
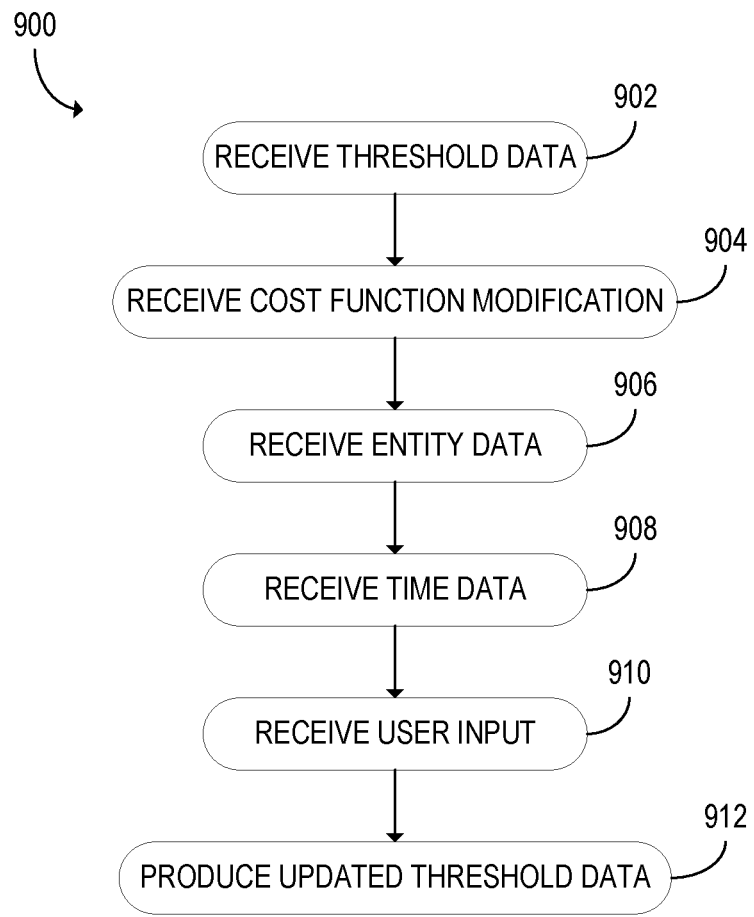
FIG. 16 shows a flowchart of a method for updating threshold data according to examples of the present disclosure.

A flowchart of a method 900 for updating threshold data is provided in FIG. 16. The following description of method 900 is provided with reference to the software and hardware components described herein. It will be appreciated that method 900 also may be performed in other contexts using other suitable hardware and software components.

At 902 the method 900 may include receiving a set of threshold data. The threshold data may include one or more probability thresholds above which a detection of a user, user location, or user activity may be registered. At 904 the method 900 may include receiving a modification to a cost function. At 906 the method 900 may include receiving entity data, which may include entity identification data, entity position/location data, and/or entity status data.

At 908 the method 900 may include receiving time data, which may include a time, a date, and/or at least one time interval elapsed since a particular output was produced or a particular input was received. At 910 the method 900 may include receiving a user input. At 912 the method 900 may include producing updated threshold data by modifying the received threshold data based at least in part on the cost function modification, entity data, time data, and/or user input.

It will be appreciated that method 900 is provided by way of example and is not meant to be limiting. Therefore, it is to be understood that method 900 may include additional and/or alternative steps relative to those illustrated in FIG. 16. Further, it is to be understood that method 900 may be performed in any suitable order. Further still, it is to be understood that one or more steps may be omitted from method 900 without departing from the scope of this disclosure.

In some examples, intelligent digital assistant system 20 may train users to interact with the system in ways that minimize ambiguities. For example, the system may customize responses, queries, and other interactions with a particular user in a manner that trains the user to speak to the system using words or phrases that more clearly convey a user's intent. In this manner, follow-up queries from the system to clarify ambiguities may be minimized. In one example, where a user has two contacts named Fred (Jones and Smith), and the user frequently tells the system, "Call Fred", the system may offer the suggestion, "When you'd like to call one of your contacts Fred, it would be helpful to use his last name too."

In some examples, intelligent digital assistant system 20 may customize a user interface to provide additional opportunities for collecting user data that may be used to enhance user experiences. In some examples, such data may be utilized with machine learning techniques to learn user preferences and make predictions from such information. In one example, where a user utilizes a calendar application that provides reminders, the system may provide a user interface, or may modify an existing user interface, to gather useful data about the user. For example, when providing a reminder, the calendar application may provide two default options of Dismiss and Snooze, with the Snooze period selectable in several 5-minute increments.

In some examples, intelligent digital assistant system 20 may modify the reminder user interface to display two different Snooze selectors with different labels—"Not now I'm busy" and "Not now, it's not important." Accordingly, when a user selects one of these more detailed selectors, the system may learn about the user; namely, what activities, persons, types of meetings, etc., the user considers "not important" or make the user "busy." In this manner, such information helps the system understand more about the user. As such data is gathered over time, machine learning techniques may be utilized to better understand user preferences and other attributes. In other examples, many other types of data (image, audio, physiological, etc.) may be gathered in conjunction with providing customized user interface experiences to learn more about a user.

With reference now to FIGS. 17-21, additional example implementations of intelligent digital assistant system 20 in a single computing device and across multiple computing devices are illustrated. Additional details regarding components and computing aspects of computing devices illustrated in FIGS. 17-26 are described below with reference to FIG. 27.

Figure 17:
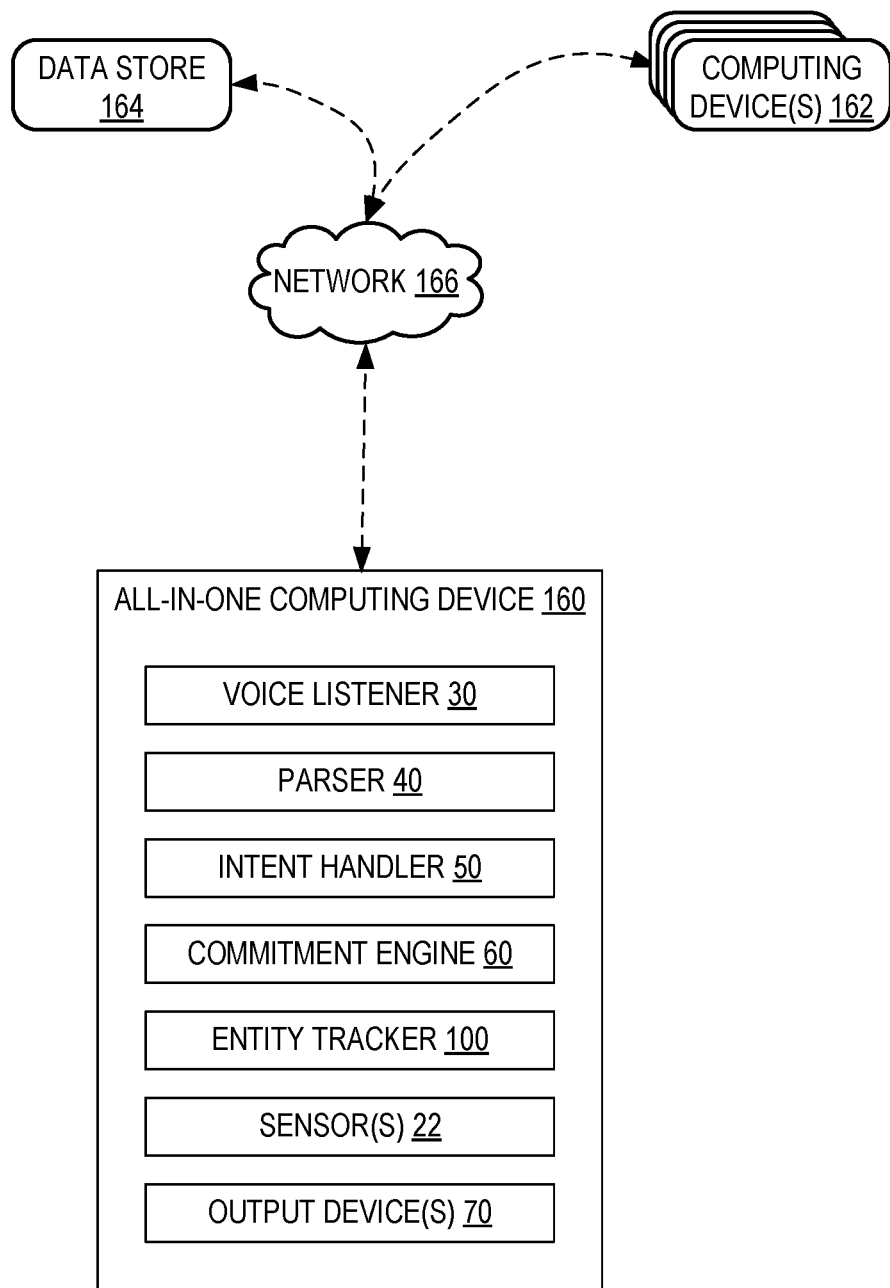
FIG. 17 schematically shows an all-in-one computing device that implements an intelligent digital assistant system according to examples of the present disclosure.

FIG. 17 shows an example of an all-in-one computing device 160 in which the components implementing intelligent digital assistant system 20 are arranged together in a standalone device. In some examples, all-in-one computing device 160 may be communicatively coupled to one or more other computing devices 162 via a network 166. In some examples, all-in-one computing device 160 may be communicatively coupled to a data store 164 that may store a variety of data, such as user profile data. All-in-one computing device 160 includes at least one sensor 22, voice listener 30, parser 40, intent handler 50, commitment engine 60, entity tracker 100, and at least one output device 70. Sensor(s) 22 include at least one microphone to receive natural language inputs from a user. In some examples one or more other types of sensor(s) 22 also may be included.

As described above, voice listener 30, parser 40, and intent handler 50 work in concert to convert natural language inputs into commitments that are executable by the all-in-one device 160. The commitment engine 60 stores such commitments in a commitment storage 626. The entity tracker 100 may provide context information to the commitment engine 60 and/or other modules. At a contextually appropriate time, the commitment engine 60 may execute a commitment and provide output, such as audio signals, to output device(s) 70.

Figure 18:
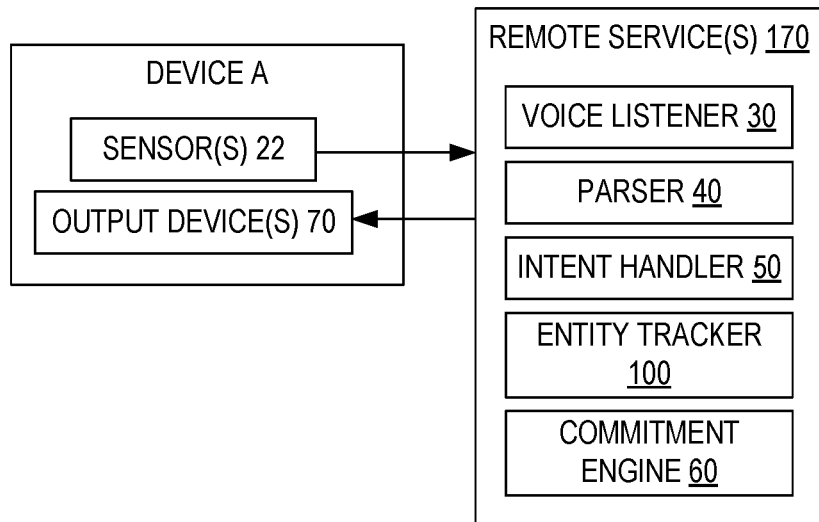
FIG. 18 schematically shows an example implementation in which one or more remote services perform functionality of the intelligent digital assistant system according to examples of the present disclosure.

FIG. 18 shows an example implementation in which one or more remote services 170 perform the natural language processing functionality of intelligent digital assistant system 20. In this example, voice listener 30, parser 40, intent handler 50, entity tracker 100 and commitment engine 60 reside on one or more computing devices, such as one or more servers, that are remotely located from a cloud-supported user device A. Sensor data from one or more sensors 22 of the user device A is provided to remote service(s) 170 via a network. For example, audio data of a user speaking may be captured by a microphone of user device A and provided to voice listener 30.

As described above, voice listener 30, parser 40, and intent handler 50 cooperate to convert the audio data into commitments that are stored in commitment engine 60. At a contextually appropriate time, the commitment engine 60 may execute a commitment and provide output, such as audio signals, to one or more output device(s) 70 of the user device A.

Figure 19:
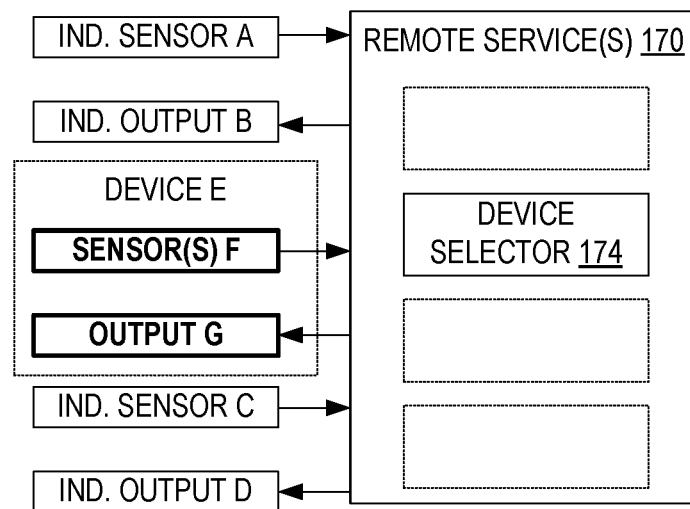
FIG. 19 schematically shows another example implementation in which one or more remote services perform functionality of intelligent digital assistant system according to examples of the present disclosure.

FIG. 19 shows another example implementation in which one or more remote services 170 perform the natural language processing functionality of intelligent digital assistant system 20. In this example, the one or more remote services 170 are communicatively coupled with a plurality of different sensors 22 and output devices 70. In this example, the sensors include individual standalone sensors A and C, such as microphones, cameras, etc. The output devices include individual standalone output devices B and D, such as loudspeakers.

The one or more remote services 170 are also communicatively coupled to a device E that includes one or more sensors F and an output device G. Device E may take the form of a simple standalone device comprising a microphone, speaker and network connectivity components. In other examples, device E may be a mobile phone, tablet computer, wall-mounted display, or other suitable computing device. In some examples, device E, sensors A and C, and output devices B and D may be part of the same cloud-supported client. In other examples, any number of individual sensors and devices may be utilized with the one or more remote services 170.

As described above, the one or more remote services 170 perform the natural language processing functionality of intelligent digital assistant system 20. In some examples, one or more of the remote services 170 may include all of the natural language processing modules of intelligent digital assistant system 20, as shown in the example of FIG. 18. In other examples, one or more remote services 170 may include less than all of the natural language processing modules, and may be communicatively coupled to the other modules located at one or more other service(s). In the present example, and as described in more detail below, one or more of the remote services 170 also may comprise a device selector 174 that may utilize sensor inputs to select output device B, D and/or G to receive output from the commitment engine 60.

Figure 20:
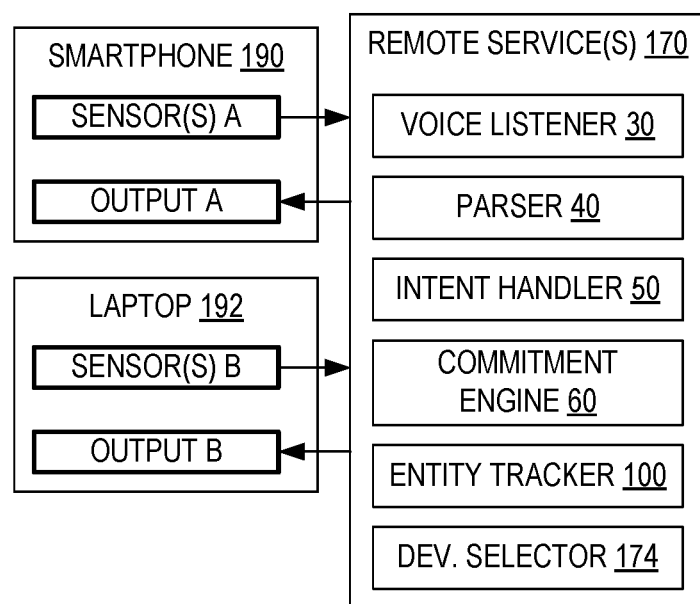
FIG. 20 schematically shows another example implementation in which one or more remote services utilizes a device selector according to examples of the present disclosure.

With reference now to FIG. 20, in some examples the intelligent digital assistant system 20 of the present disclosure may utilize device selector 174 to enable a user to communicate with another person whose location may be unknown to the user. In some examples, the system may use sensor data and/or corresponding context data to detect the presence and determine the location of the other person. Upon receiving a request from the user to speak to or locate the other person, the device selector 174 may select an appropriate output device for establishing communication between the user and the other person.

In the example use case of FIG. 20, one or more remote services 170 implementing intelligent digital assistant system 20 are communicatively coupled with a smartphone 190 and laptop 192. In one example, smartphone 190 comprises multiple sensors A including a microphone, and an output device A in the form of a speaker. The smartphone 190 may be located with a user in the user's basement media room of her home. The laptop computer 192 comprises multiple sensors B including a microphone and a webcam, and an output device B in the form of a speaker. The laptop 192 may be located in an upstairs bedroom of the home.

The user of the smartphone 190 may desire to communicate with her daughter, but may not know her current location within the home. The daughter may be in the upstairs bedroom with two other friends. The user may speak natural language inputs to indicate that she would like to communicate with her daughter. For example, the user may speak "Connect me to Sarah." The microphone in the user's smartphone 190 may receive the natural language input and send it to a remote service 170 for processing by the voice listener 30 and other components of intelligent digital assistant system 20 described above.

Upon determining the intent of the user, the commitment engine 60 may request context information 110 from the entity tracker 100 that includes the location of the user's daughter Sarah. In response, the entity tracker 100 may utilize video data from the webcam of the laptop 192 to identify Sarah in the field of view of the webcam. Entity tracker 100 may use other context information to determine that the laptop 192, and thus daughter Sarah, are located in the upstairs bedroom.

Using this information, the device selector 174 may communicatively couple the microphone and speaker of the user's smartphone 190 with microphone and speaker of laptop computer 192, and thereby allow the user to talk with her daughter.

In other examples and as discussed above, one or more other types of sensors and corresponding data may be used to locate a person or other entity. Examples include solely audio data, combinations of video and audio data, device log-in data, and other combinations of the foregoing and other sensor data.

Figure 21:
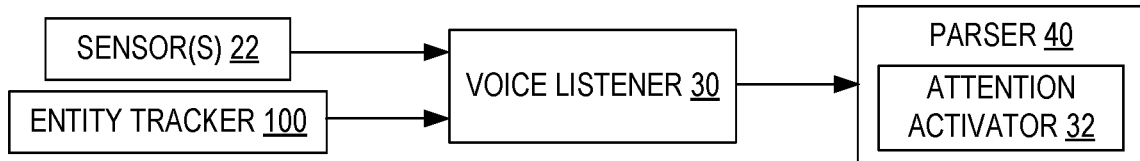
FIG. 21 schematically shows an example implementation in which one or more functions of the intelligent digital assistant system are activated upon detection of one or more spoken keywords.

In some examples, one or more functions of the intelligent digital assistant system 20 may be activated upon detection of one or more keywords that are spoken by a user. For example, the phrase "Hey Computer" may be used as a keyword phrase to activate one or more functions of the system. With reference now to FIG. 21, in one example one or more sensors 22 in the form of microphones may receive audio data of a user speaking "Hey computer, what time is the school board meeting tonight?" As described above, the voice listener 30 may process the audio data into text and confidence value(s), and pass this information to the parser 40. An attention activator 32 in parser 40 may identify the keyword phrase "Hey computer" in the text. In response, the parser 40 may activate or modify other components and functionality of the intelligent digital assistant system 20. For example, the parser 40 may increase a sampling rate of a speech recognition module to increase recognition accuracy of the user's speech that is likely to follow.

As noted above, upon processing audio data of a user's natural language input, a commitment engine may provide output to one or more output devices, such as a speaker and/or a video display. In some examples, a single device may include a microphone that captures a user's input, with such input provided to the intelligent digital assistant system 20, and a speaker that receives and broadcasts a message generated by the system in response to the input.

In some examples, a user may be in an environment with two or more microphones that may capture user speech and/or two or more speakers that may broadcast a message generated by the system in response to the speech. For example, a user may be in his media room with his mobile phone, laptop computer, tablet computer, and smart/connected television. Each of these devices may contain or be communicatively coupled with an intelligent digital assistant system 20.

A user may speak a keyword phrase that is captured by the microphones of each of the 4 devices. Accordingly, the corresponding message generated by the intelligent digital assistant system 20 may be broadcast by the speakers in all 4 devices, which may be annoying to the user. As described in more detail below, in some examples involving multiple sensors, output devices and/or other devices, the intelligent digital assistant system 20 may be configured to determine which of the multiple microphones to use for receiving user speech and/or which of the multiple speakers to use for broadcasting a corresponding message. In some examples and as described below, an aggregator may evaluate and weigh a plurality of metrics to determine which microphones and speakers to utilize.

Figure 22:
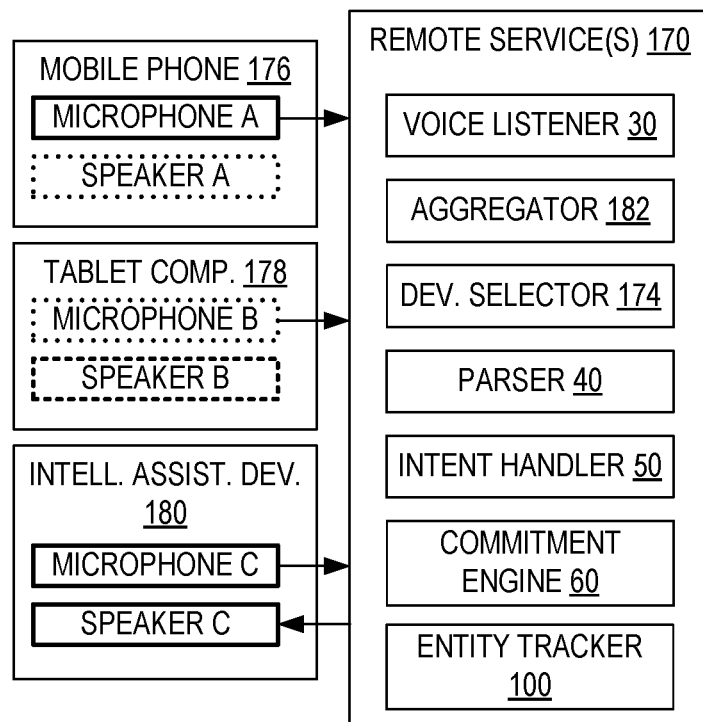
FIG. 22 schematically shows an example implementation of a multi-device environment in which sensor(s) and output device(s) are selected in response to voice activation according to examples of the present disclosure.

With reference now to FIG. 22, an example implementation of sensor and output device selection in response to voice activation in a multi-device environment is provided. In this example, one or more remote services 170 that implement the intelligent digital assistant system 20 may receive audio data from three different microphones A, B and C of three different devices, such as a mobile phone 176, tablet computer 178 and all-in-one intelligent assistant device 180.

A user in the vicinity of the three devices may speak a keyword phrase, such as "Hey Computer." Each of the microphones A, B and C may capture audio data of the user speaking this phrase and may send the audio data to voice listener 30. As described above, voice listener 30 may utilize speech recognition technologies to translate spoken utterances into text. Voice listener 30 also may assign confidence value(s) to the translated text. In some examples, the voice listener 30 may comprise a keyword detection algorithm configured to identify a keyword or keyword phrase in the translated text. The voice listener 30 may assign a confidence value to text that indicates a likelihood that the text is a keyword or keyword phrase.

In some examples, an aggregator 182 may evaluate a plurality of metrics related to a plurality of user audio data streams that are received from different individual microphones and/or from different microphone arrays. As described in more detail below, the aggregator 182 may utilize these metrics to select one of the audio data streams and its corresponding microphone(s) for use in interacting with the user. In some examples, the microphone(s) that is determined to be closest to the user may be selected. In some examples, the microphone(s) that is determined to provide the highest quality audio data may be selected. In some examples, the microphone(s) providing the highest quality audio data may be determined to be the closest microphone(s) to the user, and therefore may be selected.

When a microphone has been selected, the device selector 174 may select a speaker associated with this microphone to output a response to the user. For example, where the microphone is a component of a device that includes a speaker, this speaker may be selected. Where the microphone is a standalone microphone, the aggregator 182 may select another speaker in the vicinity of the user to output the response. In the example of FIG. 22, the aggregator 182 is located on one of the remote services 170 that implements at least a portion of the intelligent digital assistant system 20.

In other examples, the aggregator 182 may be located on another computing device, such as in another cloud-based service.

In one use case example, the aggregator 182 may utilize 4 metrics to evaluate a user audio data stream that is received: (1) an amplitude (volume) of the received audio signal; (2) a signal-to-noise (S/N) ratio of the audio signal; (3) a keyword confidence value indicating a likelihood that the data stream contains a keyword or keyword phrase; and (4) a user identification confidence value indicating a likelihood that the speaker is a particular person.

In some examples, the amplitude and/or S/N values may be received with the audio data stream. In other examples, amplitude and/or S/N values may be determined by the voice listener 30 or other components of the intelligent digital assistant system 20. As described above, the keyword confidence value may be determined by the voice listener 30. Also as described above, the user identification confidence value may be determined by entity tracker 100. In some examples, the user speaking the input may be identified by voice recognition as a known speaker or an unknown speaker, and assigned a corresponding level of confidence.

The S/N ratio may be calculated for the received audio input by comparing a signal level of a user's voice to a level of background noise. In some examples the amplitude of the input may be used to determine a proximity of the user to the corresponding microphone. It will be appreciated that the metrics discussed in the present implementations are provided as examples and are not meant to be limiting.

Each of the received audio data streams also may include a device ID that identifies the particular device or standalone sensor that is providing the data stream. In some examples, after receiving a first set of metrics from a first device or sensor, the aggregator 182 may pause for a predetermined period of time to determine if one or more other devices/sensors also received the keyword or keyword phrase from the same person as the user identified in the first set of metrics. For example, the aggregator 182 may pause for 0.5 seconds, 1.0 seconds, or any other period of time that does not create a negative user experience for the user.

In the present example and as shown in FIG. 22, the aggregator 182 evaluates metrics for audio data streams received from the mobile phone 176, tablet computer 178 and all-in-one intelligent assistant device 180. For each device, the aggregator 182 may combine the 4 metrics into a single selectability score, such as by averaging the 4 metrics. In some examples and prior to combining, each of the metrics may be weighted by empirically-determined weights that reflect the accuracy of a metric in predicting the device/microphone and corresponding audio data stream that will provide the best user experience. By comparing the selectability scores of each of the devices/microphones and their data streams, the aggregator 182 may identify and select the desired device/data stream.

In one example, for each of the 4 metrics, the aggregator 178 may compare the scores of each device/microphone and correspondingly rank the devices/microphone per metric. For example, the aggregator 178 may determine the following scores for the audio data stream received from microphone A of the mobile phone 176: 1) 90% (Amplitude); 2) 90% (S/N); 3) 30% (Keyword confidence); 4) 90% (Speaker ID). Scores for the audio data stream received from microphone B of the tablet computer 178 may be: 1) 80% (Amplitude); 2) 80% (S/N); 3) 80% (Keyword confidence); 4) 80% (Speaker ID). Scores for the audio data stream received from the microphone C of the intelligent assistant device 180 may be: 1) 92% (Amplitude); 2) 88% (S/N); 3) 90% (Keyword confidence); 4) 92% (Speaker ID).

In this example, the rankings of the 3 devices for each of the 4 metrics would be as follows:
- A. Amplitude—1. Intelligent assistant device; 2. Mobile phone; 3. Tablet computer.
- B. S/N Ratio—1. Mobile phone; 2. Intelligent assistant device; 3. Tablet computer.
- C. Keyword Confidence—1. Intelligent assistant device; 2. Tablet computer; 3. Mobile phone.
- D. Speaker ID—1. Intelligent assistant device; 2. Mobile phone; 3. Tablet computer.

Each device may be awarded points based on its ranking in each metric category. For example, a first place ranking=1 point, second place=2 points and third place=3 points. For each device, its points are totaled for the 4 metrics and averaged. The aggregator 182 selects the device (and corresponding data stream) with the lowest average point total. In the present example, the final point totals and rankings are: 1. Intelligent assistant device=>1.25; 2. Mobile phone=>2.0; 3. Tablet computer=>2.75. Thus, the aggregator 178 selects the data stream from the intelligent assistant device 180n for continued analysis by the intelligent digital assistant system 20. Additionally, and based on the above ranking, the device selector 174 may select the intelligent assistant device 180 to receive the message(s) generated by commitment engine 60 as a result of the analysis.

In some examples, upon selection by the aggregator 182 of the intelligent assistant device 180 as described above, the aggregator also may cause the other two devices to refrain from sending audio data streams that are associated with the same speaker ID (i.e., person) that is associated with the analyzed data stream. In this manner, where the same user provides more natural language input after the initial input, only the selected intelligent assistant device 180 will provide the corresponding audio data to the remote service(s) 170. In some examples, the other two devices may resume sending audio data streams when the same person speaks the keyword or keyword phrase. In these cases, the above-described selection process may be performed again to determine the selected device.

In some examples and as noted above, prior to averaging the awarded points, each point award may be multiplied by an empirically-determined weighted value that reflects the accuracy of a metric in predicting the device and corresponding audio data stream that will provide the best user experience. In some examples, one or more machine learning techniques may be utilized to build models for computing the different metrics.

In some example implementations, the signal amplitude may strongly correlate to a user's distance from the microphone receiving the user's speech. The S/N ratio also may provide a good indicator of the user's distance from the microphone, as a lower noise value may correlate to the user being closer to the microphone. Where the signal amplitude and S/N ratio of the signal are both relatively high, the speaker ID accuracy may correspondingly benefit from the strong signal.

It will be appreciated that the methods and use cases described above are merely examples, and many variations are possible. For example, a subset of the above 4 metrics may be utilized to evaluate a user audio data stream. In other examples, one or more additional metrics also may be utilized.

In some examples, a user who has previously established a conversation with the intelligent digital assistant system 20 via a selected device among multiple devices may have a brief pause before initiating a next conversation with the same device. The system may compare the duration of the pause to a predetermined time period, and may consider the comparison in selecting a device for the next conversation. For example, where the duration of the pause is less than the predetermined period, such as 5 seconds, the system may include the recently-established speaker ID and the existence of the previous conversation in the device determination analysis as a bias towards selecting the same device for the next conversation.

The examples described above include recognition of an audible keyword to activate one or more functions of the intelligent digital assistant system. In some examples, functions of the system may be activated by recognition of one or more other signals. Such signals may include, for example, a user gesture captured by a camera, a user eye-gaze, and a face direction of the user.

In some examples, one or more of the above-described techniques for device selection may be utilized to automatically update the selected device based on one or more factors. For example, where a user is communicating with the intelligent digital assistant system 20 via a first device, as the user changes her location and moves farther away from the first device, the system may correspondingly change the selected device to a second device closer to the user's new location.

In some implementations, imaging data in addition to audio data from one or more image sensors may be utilized to select a device. For example, context data 110 received from entity tracker 100 may include imaging data that may be used to select a device. Examples of imaging data may include video from an RGB camera, infrared images from an IR camera, depth images from a depth camera, thermal images from a thermal camera, etc. For example, an RGB camera may track a user's location within a room. Images from the camera may be used to select the appropriate device/microphone(s) to receive the user's natural language input, and/or to select the appropriate speaker(s) to broadcast a message to the user. In some examples and with reference to the device selection techniques described above, imaging data and related parameters may be included as a metric that is analyzed by the aggregator 182 to determine device selection.

In some examples, captured images of a user may be used to identify which device a user is facing when speaking. In some examples, indicators such as face detection may be used to identify a user. In some examples, captured video may indicate lip movement of a user that may be used to associate a spoken keyword with the user. In an environment with multiple users, such indicators also may identify the particular user who is addressing a device. As such, both voice and physical recognition may be used as parameters to distinguish a user from among the plurality of users.

Other examples of inputs that may be used in selecting a device/microphone and/or speaker include radar signals and lidar signals. In some examples, signals from connected devices may indicate that a user is interacting with the device. In one example, a user may activate a mobile phone via fingerprint recognition. Such an interaction may be a strong indicator that the user is present at the location of the phone.

Figure 23:
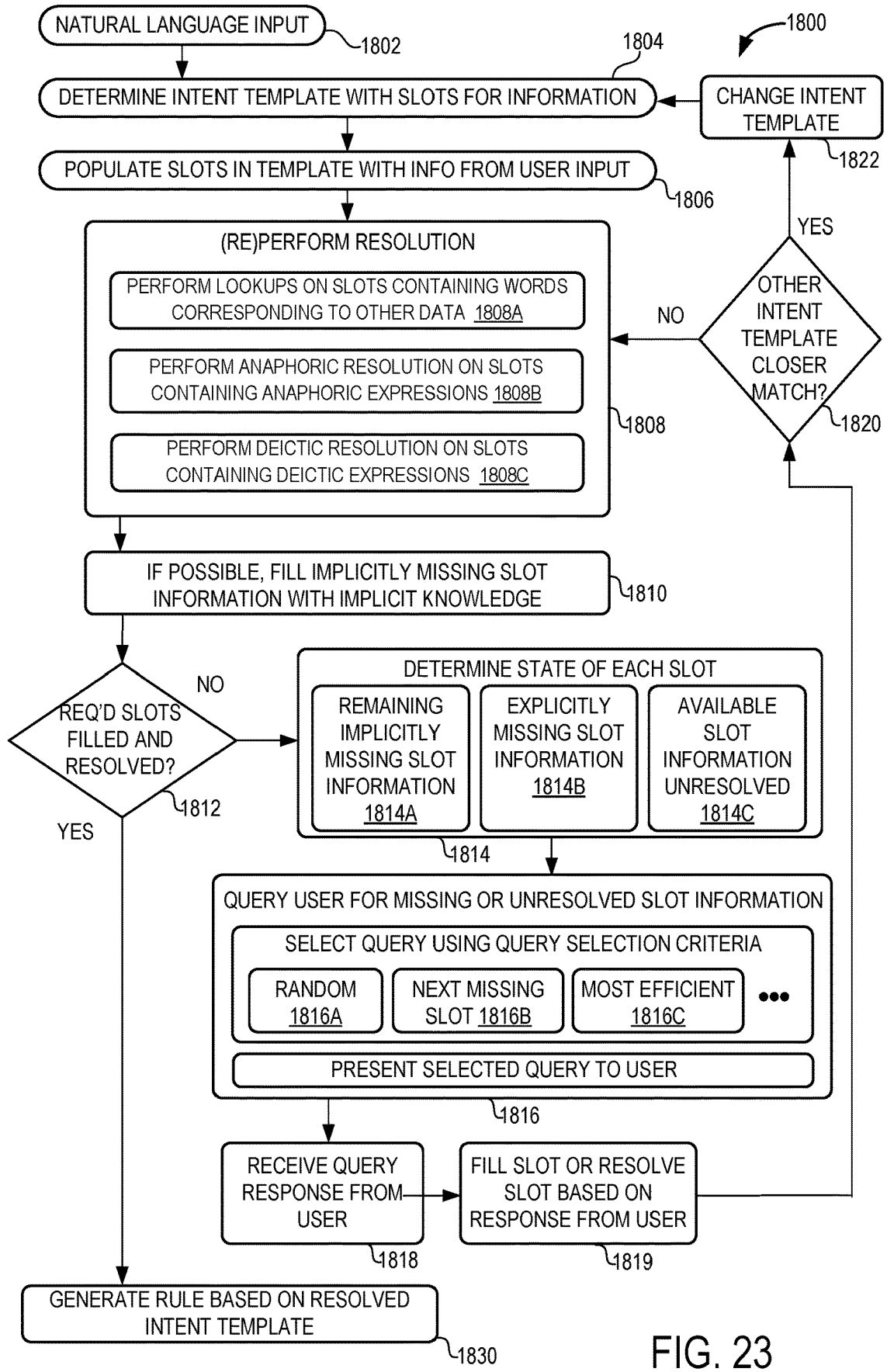
FIG. 23 shows a detailed flowchart of an implementation of a method for intent-based information resolution according to another example of the present disclosure.

FIG. 23 shows an alternative implementation by the intelligent digital assistant system 20 of intent-based information resolution, similar in some respects to the method illustrated above in FIGS. 6A and 6B. However, FIG. 23 emphasizes the looped nature of the method to determine an intent template that represents the intent of the user, fill in missing information required for the system to execute the intent, resolve ambiguous information, change information based on queries to the user and new user input, and generate a rule based on a resolved intent template. To implement the method illustrated in FIG. 23, a processor may execute one or more programs of the intelligent digital assistant system described herein to present a user interface to a user. The user interface may be an audio user interface, in which the user speaks utterances that are received via a microphone and the system responds with audio responses emitted via a speaker; a graphical user interface displaying visual (e.g., textual or graphical) representations of a dialog; or a combination thereof, and may also include two- or three-dimensional gesture recognition sensed via a touch screen or depth camera for example. Schematic representations of dialogs presented via the user interface are illustrated in FIG. 24-26B, described below. Executing the programs at the processor may cause the steps of method 1800 to be performed.

The intent template may be determined using various computing methods. In an example involving machine learning, a set of training examples for circumstances under which the action "close the window" may be executed are applied to the programs of the system 20 using machine learning techniques. The words or utterance "it's cold in here" may map to a number of different intents, from "turn up the heat" to "close the window." In a circumstance where the heat is up and the window is open, the words or utterance "it's cold in here" may result directly in the action of closing the window, whereas if the window is open but the heat is not up may result in an intent template being determined that requires additional information from the user. Similar examples may be used as training examples for the programs of the system 20 to map words or utterances to various intent templates. Once a template is determined, the programs of the system 20 may be executed using the techniques of method 1800 to then fill the missing information in the determined intent template or change the intent template based on subsequent new information from the user. It will be appreciated that as an alternative to machine learning, hard coding or other computing techniques may be employed in the programs of the system 20. These may be applied to the generation of intent templates, the application of semantic rules, and/or the resolution of information.

Method 1800, at 1802, includes receiving natural language user input from the user via the user interface. At 1804, the method includes parsing the user input at an intent handler of the system to determine an intent template with slots for information. The intent template is utilized in linking natural language to machine language, the intent of the natural language ultimately translated to a rule to be executed by the machine. A potential advantage of this method 1800 is that an intent may be encoded where no single word or utterance has something to do with the information filled in the intent template. For example, the natural language input from the user may be, "it's cold in here." The rule created by the machine based on the intent template may be "when the user inputs 'it's cold in here', close the window." The words or utterance of the user are mapped to an intent that will be executed by the system; mapping involves filling slots in the intent template to make the mapping between the natural language input and the machine-generated rule complete and correct.

The method 1800 may include coding for a machine to decipher the information required to execute an intent from the natural language of the user. As shown in the examples of FIGS. 24-26B, the intent template includes a trigger condition definition and an action definition, and one or more of the slots may be included in each of the trigger condition definition and the action definition. Each slot is configured to contain information to define the trigger condition or action, respectively. The slots may have an information type selected from the group consisting of not required, required and implicitly missing, required and explicitly missing, required and available but unresolved, or required and available and not requiring resolution.

At 1806, the method may include populating the slots in the intent template with collected information from the user input. It may be that more than one candidate intents corresponds to the source words or utterance from the user. In one implementation, the intent handler processes a plurality of candidate intent templates, mapping user input to potential slots until an intent matches the input of the user such that a rule may be generated as described below. At 1808, the method may include performing resolution on the intent template to partially resolve unresolved information, thereby resulting in a partially resolved intent template. This step is executed by the program once an intent template has been determined but not enough information has been collected to generate a rule or execute an action. It will be appreciated that slots in the intent template that are missing information may not all be required to generate a rule or execute an action. For example, the utterance, "Get me a taxi to the airport" requires the intent template to contain the information for the slot "me". However, since a taxi does not require a destination before it arrives, the slot for the destination (airport) is completely optional.

As shown at 1808A, performing resolution via the system may include executing lookup resolvers that translate identifiers in the user input into internal representation data. As described above, lookup resolvers may translate proper names, aliases, and other identifiers into internal representation data. Information such as "Bob" may be translated into the entity "Bob" and all of Bob's known contact information. As shown at 1808B, performing resolution via the system may include executing anaphoric resolvers that resolve information based on antecedent or postcedent expression in a context of user input, as also described above. Anaphoric resolvers may take pronouns as input and associate those pronouns with entities referenced in earlier conversations. As shown at 1808C, performing resolution via the system includes executing deixis resolvers that resolve information for words that cannot be interpreted without additional contextual information. For example, the phrase "I am going to the city" requires additional information to resolve the reference "the city". It may be that the system is aware of its location in a rural area located near the city of Kamloops; the deixis resolvers may determine that the speaker is going to Kamloops.

At 1810, the method may include filling implicitly missing slot information with implicit knowledge. This step is performed after the system 20 has filled and resolved as much slot information as possible based on direct user input at 1808. Following 1808, the system 20 determines any implicitly missing slot information if possible, as some implicitly missing slot information may be indeterminable at this step. Implicit knowledge may be derived from previously filled slots and other context information available to the system. Various heuristic techniques may be employed by the system 20 in attempting to fill the slots. Implicit knowledge may be derived by the system via the processor from data selected from the group consisting of user preferences, past usage of the user, identification of an entity, identification of an environment, placement of the entity in the environment, activities of the entity, placement of other entities in the environment, activities of the other entities, and crowd behavior. Any point in the method 1800 where the system 20 attempts to resolve information may involve the program accessing at least contextual information, stored information, databases, or other resources that include locations, times, entities and information about those variables. Resolution may originate or conclude from what is already known by the system, what is happening in the present, and/or what the system may know about what will happen in the near future.

At 1812, the method may include determining whether all required slots in the intent template are filled/available and resolved (YES at 1812). Should this condition be met, the system 20 proceeds to step 1830 that may include generating and possibly executing a rule based on a resolved intent template. However, if not all of the required slots are filled/available and resolved, the method may proceed to step 1814 where the system 20 determines the state of each slot (NO at 1812). Required slots may be in one of several conditions; at 1814A, the slot may have implicitly missing slot information that could not be filled at the step 1810; the slot may have explicitly missing slot information at 1814B; or the slot may have available slot information that is unresolved at 1814C. An example of the state 1814C may be represented by the user input, "Book my flight to BC." "BC" may be designated as information for a destination slot; however, this information is unresolvable because "BC" is not enough information to fully define the destination. It will be appreciated that the information is required to fulfill the user's request.

At step 1816 the method may include presenting a query to the user for required missing or unresolved slot information. The method at 1816 may include several possible approaches. For example, the query may be selected according to one or more selection criteria. At 1816A, the selection criteria may be defined as random selection of missing or unresolved slot information, and the system 20 may select missing or unresolved slot information at random on which to base a query to the user. It will be appreciated that this approach may be employed to present the intelligent digital assistant as appearing less rigidly systematic and to more closely simulate natural human response. At 1816B, the selection criteria may be an internal order of explicitly missing slot information that is required to be filled, and the system 20 may base the query to the user on an internal order of explicitly missing slot information that is required to be filled, moving from one slot to the next within the template according to an order of the slots within the template. At 1816C, the selection criteria may be a greatest potential to fill and resolve a highest number of slots, and the system 20 may employ an algorithm to select the most efficient query among a plurality of candidate queries, which has the greatest potential to fill and resolve the highest number of slots as calculated by the system 20. It will be appreciated that other selection criteria may be used in the selection of a query by the system 20. For example, an algorithm may be employed to present queries in a manner closely resembling a human approach to questioning, and the selection criteria may be an estimation of a user expected query computed with a highest probability among a plurality of candidate queries, according to the algorithm. Other selection criteria may be calculated by the programs executed by the system 20, whether utilizing machine learning techniques, natural language approaches, or other calculations and techniques. Once the query is selected based upon the query selection criteria, the query is presented to the user.

The step 1816 may be applied to the example described above where a user has requested a flight to be booked to BC. The system 20 may query the user at random, asking, "When are you planning to leave?" Alternatively, the system 20 may determine that that the most efficient approach to filling and resolving slot information is to ask the user, "Where will you be planning to arrive in BC?" It will be appreciated that these or other approaches may be utilized at step 1816 to determine a query to the user for the purpose of filling and resolving slot information.

The method 1800 may include step 1818, receiving a response from the user to the query at 1816. Once a response from the user is received, the method 1800 may include at 1819 filling slot information or resolving slot information based on the response from the user. Once these steps have concluded, the system 20 may repeat any or all of the steps described above. A potential advantage of the method 1800 is that the system 20 may loop through the steps every time new information is received from the user, filling slot information, changing slot information, and/or resolving slot information.

In the following steps, the intent template referred to above is referred to as a first intent template, and it will be appreciated that the first intent template was determined by selecting the first intent template from among a plurality of candidate intent templates stored or programmatically generated by the system. With this in mind, at 1820, the method may include determining that a second intent template is a closer match to the user input and the query response than the current intent template, and if so (YES at 1820), at 1822, the method may include changing the intent template to a second intent template, determining slots for information at a new execution of step 1804. On a successive time through step 1806, the method may include populating the second intent template based on the user input and the query response, and at a next time through step 1808, re-performing resolution on the populated second intent template. Even if a closer matching second intent template is not identified (NO at 1820), the method may include populating slots in the first intent template with information based on user input and the query response at a successive execution of 1806 before re-performing resolution (step 1808, subsequent time through first loop) based on the partially resolved intent template.

In this way the method loops through a subsequent execution, the system 20 attempting to fill slots with information based upon implicit knowledge derived from previously filled slots and other context information available to the system and/or if necessary querying the user for information. It will be appreciated that the second intent template may be an independent intent template, or a modified version of the first intent template. Typically, the entire intent template is re-resolved at 1808 each time missing information is added. It may be that new information collected by the system 20 allows the information in multiple slots to be filled or resolved at once. Eventually all missing information is gathered or provided, and thus the method may include exiting the loop (step 1812 at YES) upon determining that no slot exists with required missing or unresolved slot information.

It will be appreciated that slot information may be determined unresolved at subsequent passes through the loop and some slot information may be determined missing that the system 20 had previously, incorrectly filled. Ambiguous information may be recognized by the system in the form of incoming data conflicting with information in a filled slot, data that indicates the intent template is incorrect, or data that contradicts how information has been parsed into slots. During re-performing resolution, the method further may include, for example, determining that slot information occupies incorrect slots and moving slot information to correct slots based on information collected by the system. In addition, during re-performing resolution, the method 1800 may include extracting new information and replacing existing slot information with the new information based on information collected by the system 20.

It will be appreciated that the method 1800 as described here can be contrasted with directed dialogue, in which information is exchanged in a linear fashion. The method 1800 has potential advantages by looping through steps repeatedly at the reception of new information to collect missing information and resolve ambiguous information. At every state change on each pass through the illustrated looping of the method 1800, assumptions are reassessed by the system 20 during the re-performance of resolution. A potential advantage of this process is that demand on the user for information is minimized; additionally, the response of the system 1800 to the user may follow an interaction more natural to the user, and indeed may more accurately assess the user's intent, even with minimal user inputs.

Should the method 1800 further include determining that all required information is available and resolved in the intent template, the method may include, at 1830, generating a rule based upon the intent template with all required information being available and resolved. The rule that is generated is a rule to perform an action defined by the action definition upon the occurrence of a trigger defined by the trigger condition definition. Ultimately, the rule may be applied, and the system may monitor for the trigger condition, and once detected, may perform the steps of the action according to the action definition. Example use case scenarios illustrating the method 1800 of FIG. 23 will now be described with reference to FIGS. 24-26B.

Figure 24:
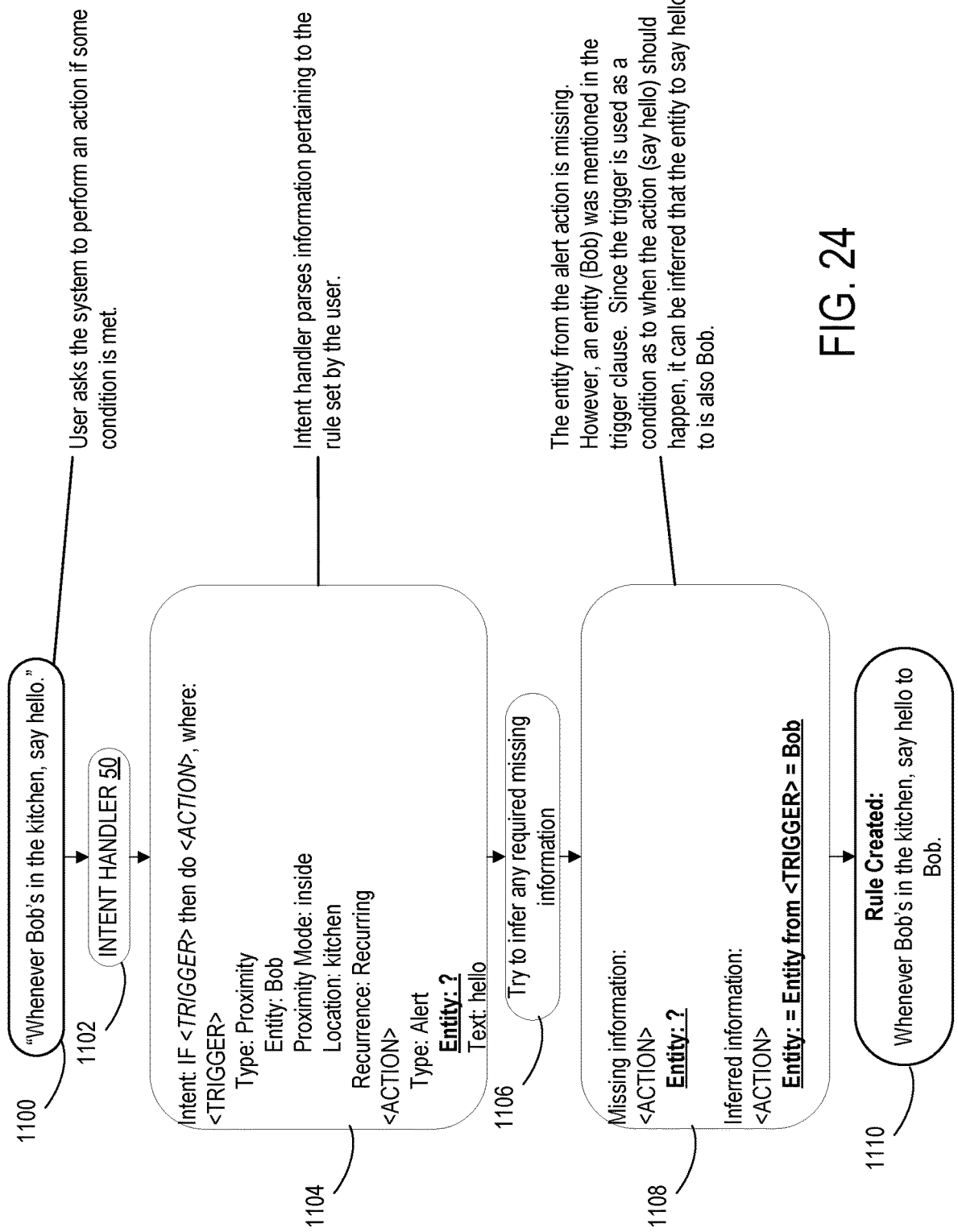
FIG. 24 schematically shows a first example of intent-based information resolution.

FIG. 24 shows a first example of intent-based information resolution. This first example has been described more broadly above within the context of FIGS. 6A-B but is repeated here for the sake of comparison with the more complex examples that follow. In this first example, the user initially directs the system 20 at 1100 to perform an action if some condition is met, saying, "Whenever Bob's in the kitchen, say 'hello'". The intent handler 50 directs the user input at 1102 into an intent template determined by the program at 1104. In this instance at 1106, the system 20 infers any implicitly missing information. At 1108, the system 20 determines that the entity to whom "hello" will be addressed is "Bob" based on the parsing of the user input 680 and the inference of the system 20. This process exemplifies anaphoric resolution, as the user input implies "say hello to him", where the system must resolve the pronoun "him". At 1110 the system 20 will then create and apply a rule to say "hello" to Bob whenever Bob is in the kitchen.

Figure 25:
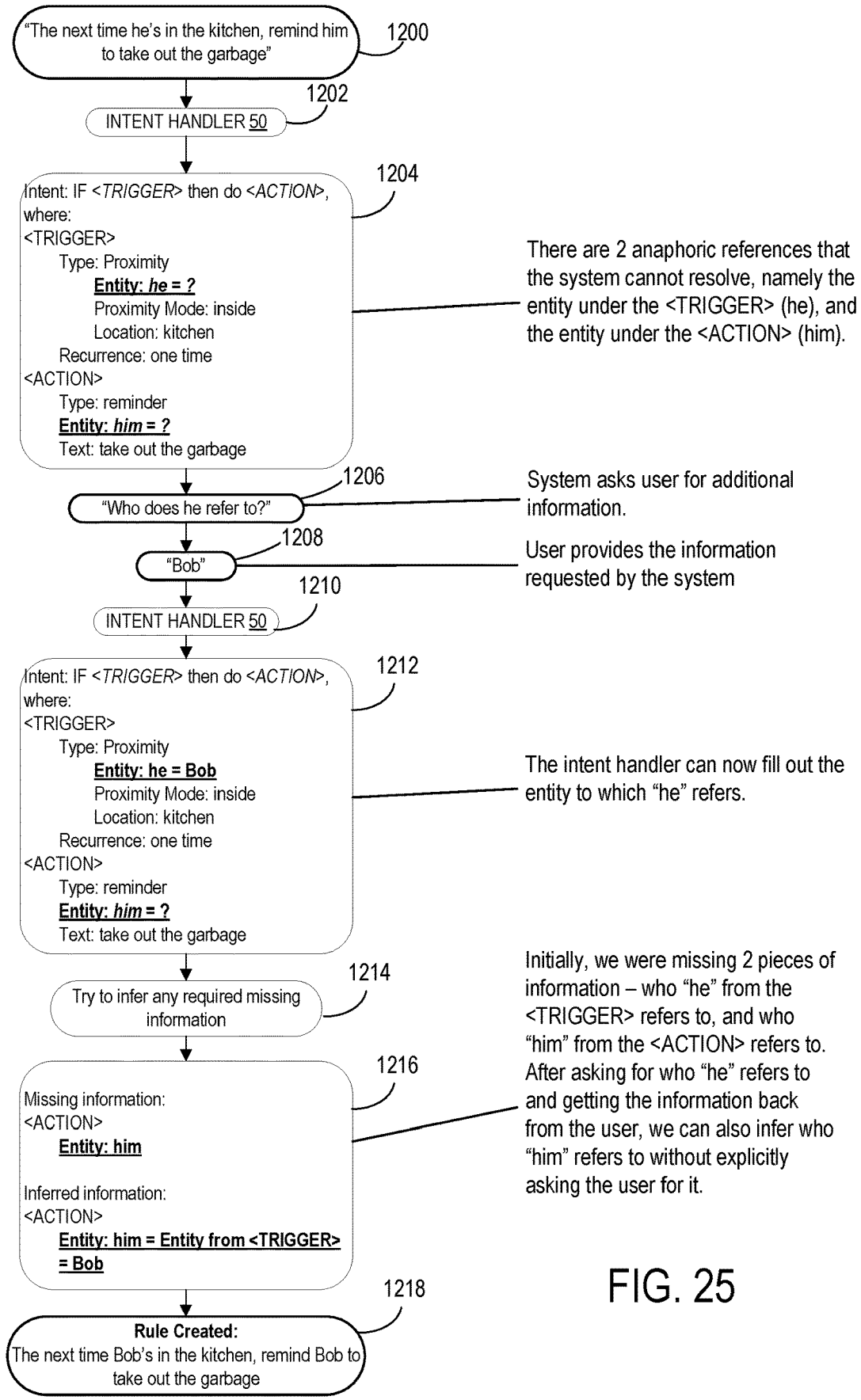
FIG. 25 schematically shows a second example of intent-based information resolution.

FIG. 25 shows a second example of intent-based information resolution. In this example, the user first directs the system 20 at 1200 to perform an action if some condition is met, saying, "The next time he's in the kitchen, remind him to take out the garbage". This example also includes anaphoric references in the pronouns "he" and "him"; however, in this case the system 20 is unable to resolve the unknown information implicitly. The intent handler 50 at 1202 parses the user input 680 into an intent template at 1204 determined by the system 20. In this example, two anaphoric references exist that the system 20 cannot resolve: the entity referred to by "he" and the entity who will undertake the action. The system 20 queries the user at 1206 for additional information, which is provided by the user at 1208 as "Bob". At 1210 the intent handler 50 assigns "Bob" from the information collected from the user. "Bob" is assigned by the intent handler 50 to "he" at 1212. The system 20 attempts to infer any required missing information at 1214. In this instance, at 1216 the system 20 determines that the entity who will undertake the action is also "Bob", and no further query is made of the user. The new information collected from the user at 1208 allow for two slots to be resolved on one new piece of information. This determination may be made by the techniques described above executed by the intent handler 50. At 1218 the system will then create and apply a rule to remind Bob to take out the garbage the next time Bob is in the kitchen.

Figure 26A:
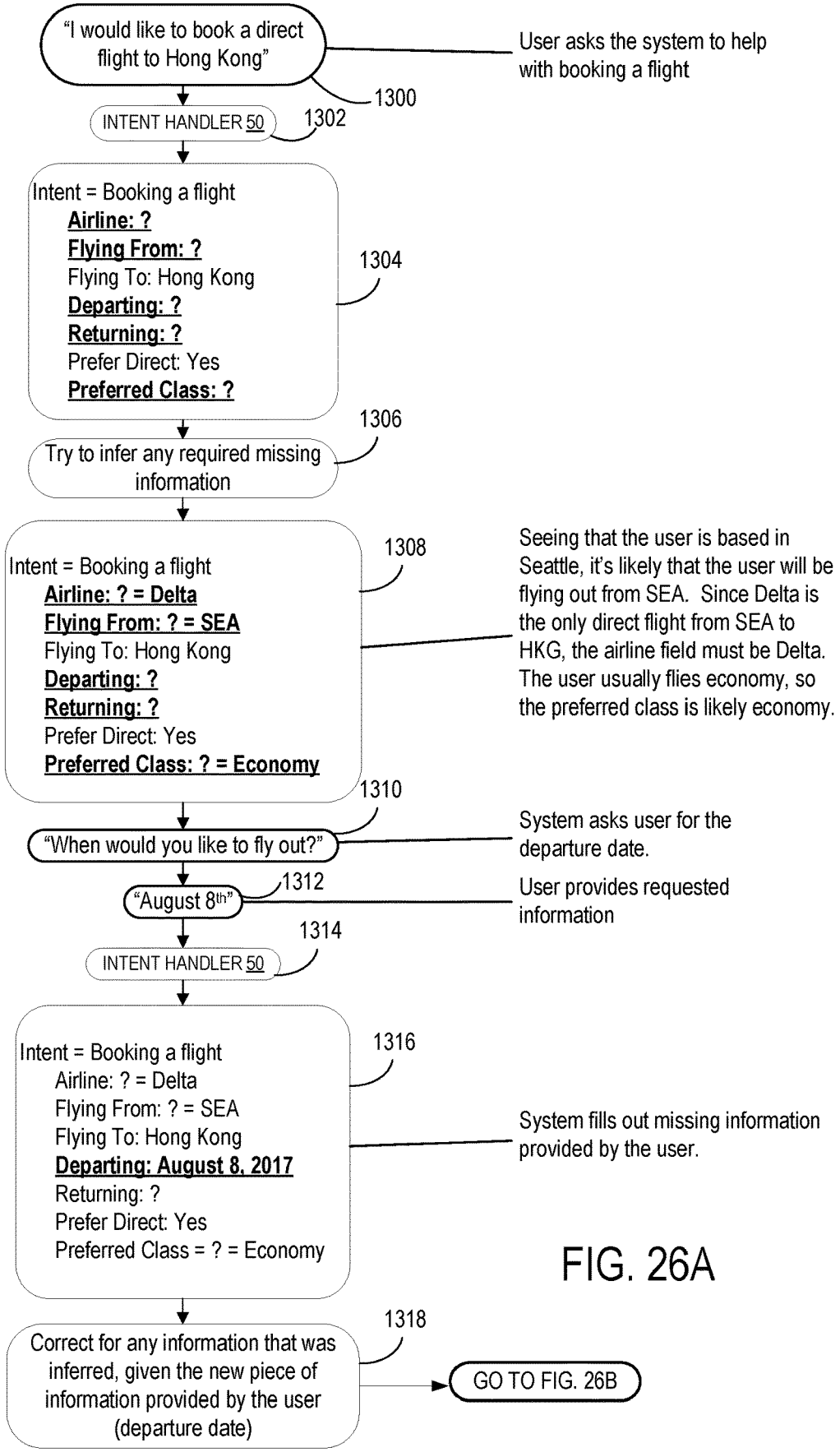
FIGS. 26A-B schematically show a third example of intent-based information resolution.
Figure 26B:
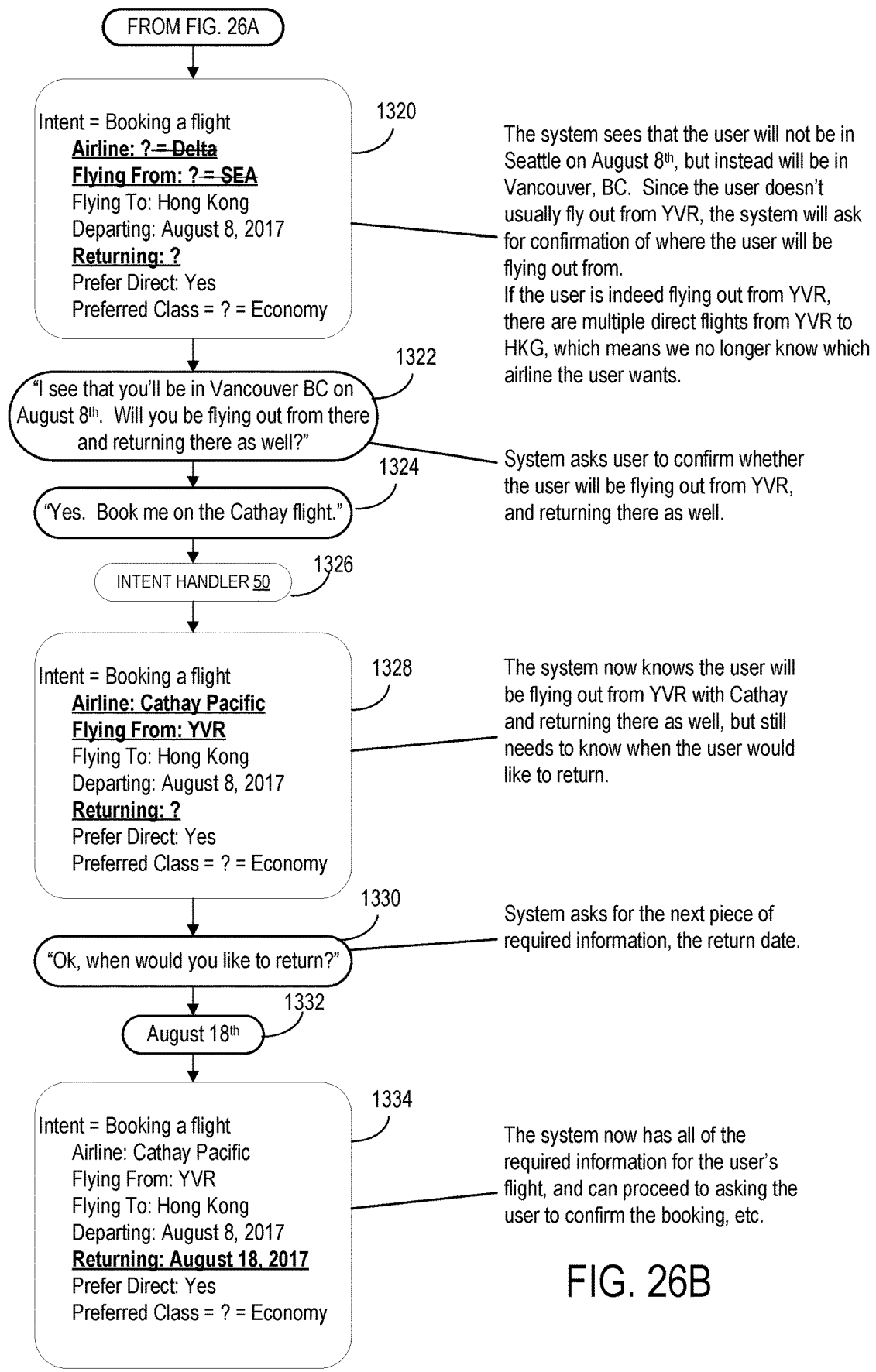

FIGS. 26A-B show a third example of intent-based information resolution. This example shows the increasing complexity with which the intent handler 50 may operate based on the analysis described herein. In this example, the user expresses a desire to book a flight to Hong Kong at 1300. The intent handler 50 directs the user input at 1302 into an intent template at 1304 determined by the system 20. In this instance, a number of slots are missing information. The system 20 attempts to infer any required information at 1306. At 1308, since the system 20 has the information that the user is based in Seattle, the system 20 implicitly determines that the user will be flying out of Seattle. This may be resolved by the application of deixis resolvers as described above if the system determines that "I would like to book a direct flight to Hong Kong" implies "I would like to book a direct flight to Hong Kong from here" where "here" is a deictic word. Alternatively or additionally, the system 20 may apply lookup resolvers as described above in the determination of the user's current location. Information available to the system 20 indicates that Delta is the only direct flight from SEA to HKG, and therefore the slot information for the airline must be Delta. Since the user generally flies economy, the system 20 assigns "economy" as the slot information in the preferred class slot. However, the system 20 cannot infer, in this case, the departure date; therefore, at 1310 the system 20 queries the user to provide that information, which is then directed by the intent handler 50 to fill in the missing slot information. "August 8th" is new information collected from the user at 1312, which is then analyzed by the intent handler 50 at 1314.

In the next step at 1316, the system 20 fills the departure slot with the missing information. Next, at 1318, the system 20 continues to correct for any information that was inferred given the information collected from the user. This is shown in FIG. 26B. The system 20 at 1320 has information showing that the user will not be in Seattle on August $8^{th}$, the given departure date. Since the user appears to be flying out from YVR, and there are multiple direct flights from YVR to HKG, the system 20 may have to change the inferred slot information that the airline is Delta. This is determined when the system 20 compares information in a filled slot with new information collected from the user. In terms of FIG. 23, the new information collected from the user triggers the repetition of a loop as an outcome of detecting unresolved, required information. Reperforming resolution follows. Since the information cannot be resolved implicitly, the system 20 must query the user at 1322 to confirm whether the user will be flying out from YVR and returning there as well. The user provides the information that a flight should be booked on Cathay at 1324. At this point, the system 20 has collected the information that the user will be flying out from YVR on Cathay and returning there as well; this information is directed at 1326 by the intent handler 50. However, it is still unknown when the user would like to return. Since this information cannot be inferred by the system 20 at 1328, the system 20 queries the user at 1330 to determine the return date. Once this information is given by the user at 1332, the system 20 has all of the information needed to execute the user's request at 1334.

In some embodiments, the methods and processes described herein may be tied to a computing system of one or more computing devices. In particular, such methods and processes may be implemented as a computer-application program or service, an application-programming interface (API), a library, and/or other computer-program product.

Figure 27:
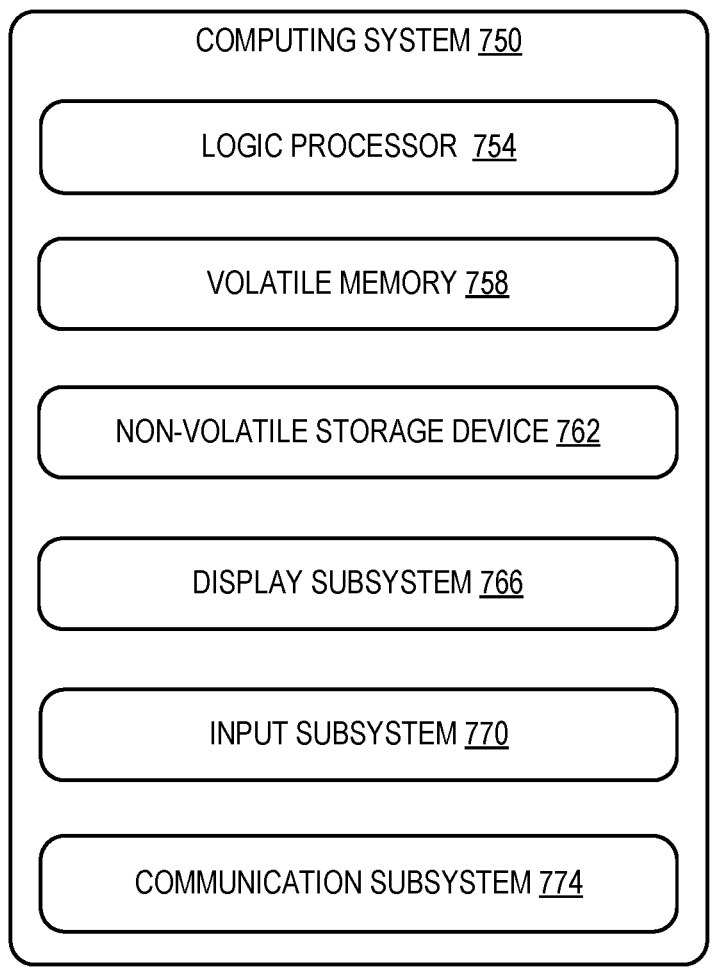
FIG. 27 schematically shows a computing system according to examples of the present disclosure.

FIG. 27 schematically shows a non-limiting embodiment of a computing system 750 that can enact one or more of the methods and processes described above. Computing system 750 is shown in simplified form. Computing system 750 may take the form of one or more personal computers, server computers, tablet computers, home-entertainment computers, network computing devices, gaming devices, mobile computing devices, mobile communication devices (e.g., smartphone), and/or other computing devices.

Computing system 750 includes a logic processor 754, volatile memory 758, and a non-volatile storage device 762. Computing system 700 may optionally include a display subsystem 766, input subsystem 770, communication subsystem 774, and/or other components not shown in FIG. 27.

Logic processor 754 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor 754 may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 754 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor 754 may be virtualized and executed by remotely accessible, networked computing devices configured in a cloud-computing configuration. In such a case, these virtualized aspects may be run on different physical logic processors of various different machines.

Volatile memory 758 may include physical devices that include random access memory. Volatile memory 758 is typically utilized by logic processor 754 to temporarily store information during processing of software instructions. It will be appreciated that volatile memory 758 typically does not continue to store instructions when power is cut to the volatile memory.

Non-volatile storage device 762 includes one or more physical devices configured to hold instructions executable by the logic processors to implement the methods and processes described herein. When such methods and processes are implemented, the state of non-volatile storage device 762 may be transformed—e.g., to hold different data.

Non-volatile storage device 762 may include physical devices that are removable and/or built-in. Non-volatile storage device 762 may include optical memory (CD, DVD, HD-DVD, Blu-Ray Disc, etc.), semiconductor memory (ROM, EPROM, EEPROM, FLASH memory, etc.), and/or magnetic memory (hard-disk drive, floppy-disk drive, tape drive, MRAM, etc.), or other mass storage device technology. Non-volatile storage device 762 may include nonvolatile, dynamic, static, read/write, read-only, sequential-access, location-addressable, file-addressable, and/or content-addressable devices. It will be appreciated that non-volatile storage device 762 is configured to hold instructions even when power is cut to the non-volatile storage device.

Aspects of logic processor 754, volatile memory 758, and non-volatile storage device 762 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module", "program" and "engine" may be used to describe an aspect of computing system 750 implemented to perform a particular function. In some cases, a module, program or engine may be instantiated via logic processor 754 executing instructions held by non-volatile storage device 762, using portions of volatile memory 758. It will be understood that different modules, programs or engines may be instantiated from the same application, service, code block, object, library, routine, API, function, etc. Likewise, the same module, program or engine may be instantiated by different applications, services, code blocks, objects, routines, APIs, functions, etc. The terms modules, programs and engines encompass individual or groups of executable files, data files, libraries, drivers, scripts, database records, etc.

It will be appreciated that a "service", as used herein, is an application program that may be executable across multiple user sessions. A service may be available to one or more system components, programs, and/or other services. In some implementations, a service may run on one or more server-computing devices.

When included, display subsystem 766 may be used to present a visual representation of data held by non-volatile storage device 762. As the herein described methods and processes change the data held by the non-volatile storage device, and thus transform the state of the non-volatile storage device, the state of display subsystem 766 may likewise be transformed to visually represent changes in the underlying data. Display subsystem 766 may include one or more display devices utilizing virtually any type of technology. Such display devices may be combined with logic processor 754, volatile memory 758, and/or non-volatile storage device 762 in a shared enclosure, or such display devices may be peripheral display devices.

When included, input subsystem 770 may comprise or interface with one or more user-input devices. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection, gaze detection, and/or intent recognition; electric-field sensing componentry for assessing brain activity; any of the sensors described with respect to the example use cases and environments discussed above; and/or any other suitable sensor.

When included, communication subsystem 774 may be configured to communicatively couple computing system 750 with one or more other computing devices. Communication subsystem 774 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 750 to send and receive data to and from other devices via a network such as the Internet.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A method executed by a computing system of one or more computing devices, the method comprising:
   receiving user input via an interface of the computing device, the user input including natural language user input;
   performing the following actions in a loop with respect to a first intent template defining a set of slots until the set of slots are both filled and resolved, wherein the first intent template is selected from among a plurality of candidate intent templates:
   populating one or more slots of the set of slots of the first intent template with information based on the user input,
   if the first intent template is partially resolved in which a subject slot of the set of slots is not both filled and resolved, performing the following additional actions as part of the loop:
   determining a state of the subject slot as at least one of unfilled or unresolved,
   presenting a query for a user to fill or resolve the subject slot based on query selection criteria,
   receiving a user response to the query,
   altering the state of the subject slot based on the user response to the query, and
   re-executing the loop with the user response to the query being incorporated into the user input, wherein an iteration of the loop during re-execution of the loop includes:
   determining that a second intent template of the plurality candidate intent templates is a closer match to the user input and the user response to the query, based on slots filled and resolved within the loop; and responsive to determining that the second intent
    template is the closer match, exiting the loop
    prior to the subject slot of the set of slots being
    both filled and resolved;
populating one or more slots defined by the second intent
    template based on the user input and the user response
    to the query; and
performing an action that is based on the second intent
    template following populating the one or more slots of
    the second intent template.

2. The method of claim 1, further comprising:
parsing the user input to determine the first intent template
    defining the set of slots; and
further performing in the loop:
    filling implicitly missing slot information of the subject
        slot with implicit knowledge derived from one or
        more previously filled slots of the set of slots.

3. The method of claim 2, wherein the implicit knowledge is further derived from data that includes at least one of: user preferences, past usage, identification of an entity, identification of an environment, placement of the entity in the environment, activities of the entity, placement of other entities in the environment, activities of the other entities, crowd behavior.

4. The method of claim 1, wherein the query selection criteria includes at least one of: random selection of missing or unresolved slot information, an internal order of explicitly missing slot information that is required to be filled, a greatest potential to fill and resolve a highest number of slots, an estimation of a user expected query, a programmatically calculated selection criteria.

5. The method of claim 1, wherein:
the second intent template includes a trigger condition
    definition and an action definition;
one or more slots of the set of slots are included in the
    trigger condition definition;
one or more slots of the set of slots are included in the
    action definition; and
each slot of the set of slots is configured to contain
    information to define a trigger condition defined by the
    trigger condition definition or the action defined by the
    action definition.

6. The method of claim 5, further comprising generating a rule based upon the set of slots of the second intent template being both filled and resolved, the rule being to perform the action defined by the action definition upon an occurrence of the trigger condition defined by the trigger condition definition.

7. The method of claim 1, wherein
the set of slots is a subset of a superset of slots defined by
    the first intent template;
each slot of the superset of slots initially has an information type that includes one of the following: not required, required and implicitly missing, required and explicitly missing, required and available but unresolved, required and available and not requiring resolution; and
wherein each slot of the set of slots initially has an
    information type that includes one of the following:
    required and implicitly missing, required and explicitly
    missing, required and available but unresolved.

8. The method of claim 1, further comprising:
based on the user response, moving information populating a slot of the set of slots to a different slot of the set of slots.

9. The method of claim 1, further comprising:
based on the user response, replacing information populating a slot of the set of slots with new information contained in the user response.

10. A computing system, comprising:
one or more processor devices;
a storage device having instructions stored thereon
    executable by the one or more processors devices to:
    receive user input via an interface of the computing
        system, the user input including natural language
        user input;
    perform the following actions in a loop with respect to
        a first intent template defining a set of slots until the
        set of slots are both filled and resolved, wherein the
        first intent template is selected from among a plurality of candidate intent templates:
        populate one or more slots of the set of slots of the
            first intent template with information based on the
            user input,
        if the first intent template is partially resolved in
            which a subject slot of the set of slots is not both
            filled and resolved, perform the following additional actions as part of the loop:
            determine a state of the subject slot as at least one
                of unfilled or unresolved,
            present a query for a user to fill or resolve the
                subject slot based on query selection criteria,
            receive a user response to the query,
            alter the state of the subject slot based on the user
                response to the query, and
        re-execute the loop with the user response to the
            query being incorporated into the user input,
            wherein an iteration of the loop during re-execution of the loop includes:
            determining that a second intent template of the
                plurality candidate intent templates is a closer
                match to the user input and the user response to
                the query, based on slots filled and resolved
                within the loop; and
            responsive to determining that the second intent
                template is the closer match, exiting the loop
                prior to the subject slot of the set of slots being
                both filled and resolved;
    populate one or more slots defined by the second intent
        template based on the user input and the user response
        to the query; and
    perform an action that is based on the second intent
        template following populating the one or more slots of
        the second intent template.

11. The computing system of claim 10, wherein the instructions are further executable by the one or more processor devices to:
parse the user input to determine the first intent template
    defining the set of slots; and
further perform in the loop:
    fill implicitly missing slot information of the subject
        slot with implicit knowledge derived from one or
        more previously filled slots of the set of slots.

12. The computing system of claim 10, wherein the implicit knowledge is further derived from data that includes at least one of: user preferences, past usage, identification of an entity, identification of an environment, placement of the entity in the environment, activities of the entity, placement of other entities in the environment, activities of the other entities, crowd behavior.

13. The computing system of claim 10, wherein the query selection criteria includes at least one of: random selection of missing or unresolved slot information, an internal order of explicitly missing slot information that is required to be filled, a greatest potential to fill and resolve a highest number of slots, an estimation of a user expected query, a programmatically calculated selection criteria.

14. The computing system of claim 10, wherein:
the second intent template includes a trigger condition definition and an action definition;
one or more slots of the set of slots are included in the trigger condition definition;
one or more slots of the set of slots are included in the action definition; and
each slot of the set of slots is configured to contain information to define a trigger condition defined by the trigger condition definition or the action defined by the action definition.

15. The computing system of claim 14, wherein the instructions are further executable by the one or more processor devices to:
generate a rule based upon the set of slots of the second intent template being both filled and resolved, the rule being to perform the action defined by the action definition upon an occurrence of the trigger condition defined by the trigger condition definition.

16. The computing system of claim 14, wherein:
the set of slots is a subset of a superset of slots defined by the first intent template;
each slot of the superset of slots initially has an information type that includes one of the following: not required, required and implicitly missing, required and explicitly missing, required and available but unresolved, required and available and not requiring resolution; and
wherein each slot of the set of slots initially has an information type that includes one of the following: required and implicitly missing, required and explicitly missing, required and available but unresolved.

17. The computing system of claim 10, wherein the instructions are further executable by the one or more processor devices to:
based on the user response, move information populating a slot of the set of slots to a different slot of the set of slots or replace information populating a slot of the set of slots with new information contained in the user response.

18. A method executed by a computing system of one or more computing devices, the method comprising:
receiving user input via an interface of the computing device, the user input including natural language user input;
performing the following actions in a loop with respect to a first intent template defining a set of slots until the set of slots are both filled and resolved, wherein the first intent template is selected from among a plurality of candidate intent templates:
populating one or more slots of the set of slots of the first intent template with information based on the user input,
if the first intent template is partially resolved in which a subject slot of the set of slots is not both filled and resolved, performing the following additional actions as part of the loop:
determining a state of the subject slot as at least one of unfilled or unresolved,
presenting a query for a user to fill or resolve the subject slot based on query selection criteria,
receiving a user response to the query,
altering the state of the subject slot based on the user response to the query, and
re-executing the loop with the user response to the query being incorporated into the user input, wherein an iteration of the loop during re-execution of the loop includes:
determining that a second intent template of the plurality candidate intent templates is a closer match to the user input and the user response to the query, based on slots filled and resolved within the loop; and
responsive to determining that the second intent template is the closer match, exiting the loop prior to the subject slot of the set of slots being both filled and resolved;
populating a set of one or more slots defined by the second intent template based on the user input and the user response to the query;
generating a rule based upon the set of slots of the second intent template being both filled and resolved, the rule being to perform an action defined by the second intent template upon an occurrence of a trigger condition defined by the intent template; and
performing the action that is based on the second intent template following populating the one or more slots of the second intent template,
wherein the set of one or more slots defined by the second intent template is a subset of a superset of slots defined by the second intent template in which one or more slots of the superset that are not included in the subset initially has an information type that includes: not required or not requiring resolution.

* * * * *